United States Patent
Collin-Kroepelin et al.

(10) Patent No.: US 11,298,367 B2
(45) Date of Patent: Apr. 12, 2022

(54) PRODRUGS OF SUBSTITUTED TRIAZOLE DERIVATIVES AND USES THEREOF

(71) Applicants: Bayer Aktiengesellschaft, Leverkusen (DE); Bayer Pharma Aktiengesellschaft, Berlin (DE)

(72) Inventors: Marie-Pierre Collin-Kroepelin, Wuppertal (DE); Peter Kolkhof, Wuppertal (DE); Thomas Neubauer, Wuppertal (DE); Chantal Fuerstner, Muelheim/Ruhr (DE); Elisabeth Pook, Wuppertal (DE); Matthias Beat Wittwer, Riehen (CH); Carsten Schmeck, Muelheim (DE); Pierre Wasnaire, Duesseldorf (DE); Heiko Schirmer, Solingen (DE); Hana Cernecka, Wuppertal (DE); Karoline Droebner, Velbert (DE); Hanna Tinel, Wuppertal (DE); Anja Buchmueller, Essen (DE); Thomas Mondritzki, Essen (DE); Axel Kretschmer, Wuppertal (DE); Klemens Lustig, Wuppertal (DE); Robert Fricke, Cologne (DE); Guillaume Levilain, Wuppertal (DE); Ursula Krenz, Leichlingen (DE); Norbert Witowski, Wolfenbuettel (DE)

(73) Assignee: Bayer Aktiengesellschaft, Leverkusen (DE)

( * ) Notice: Subject to any disclaimer, the term of this patent is extended or adjusted under 35 U.S.C. 154(b) by 169 days.

(21) Appl. No.: 16/758,742

(22) PCT Filed: Oct. 17, 2018

(86) PCT No.: PCT/EP2018/078364
§ 371 (c)(1),
(2) Date: Apr. 23, 2020

(87) PCT Pub. No.: WO2019/081292
PCT Pub. Date: May 2, 2019

(65) Prior Publication Data
US 2020/0338096 A1 Oct. 29, 2020

(30) Foreign Application Priority Data
Oct. 24, 2017 (EP) .................................... 17197935

(51) Int. Cl.
| | |
|---|---|
| *A61K 31/675* | (2006.01) |
| *A61P 13/12* | (2006.01) |
| *A61K 45/06* | (2006.01) |
| *C07F 9/6558* | (2006.01) |

(52) U.S. Cl.
CPC ............ *A61K 31/675* (2013.01); *A61K 45/06* (2013.01); *A61P 13/12* (2018.01); *C07F 9/65583* (2013.01)

(58) Field of Classification Search
None
See application file for complete search history.

(56) References Cited

U.S. PATENT DOCUMENTS

| | | | |
|---|---|---|---|
| 3,966,781 A | 6/1976 | Atkinson et al. | |
| 6,743,798 B1 | 6/2004 | Straub et al. | |
| 6,833,364 B1 | 12/2004 | Straub et al. | |
| 6,864,287 B1 | 3/2005 | Alonso-Alija et al. | |
| 2002/0173514 A1 | 11/2002 | Alonso-Alija et al. | |
| 2004/0082798 A1 | 4/2004 | Alonso-Alija et al. | |
| 2004/0176446 A1 | 9/2004 | Alonso-Alija et al. | |
| 2004/0224945 A1 | 11/2004 | Straub et al. | |
| 2006/0052397 A1 | 3/2006 | Alonso-Alija et al. | |
| 2007/0179139 A1 | 8/2007 | Alonso-Alija et al. | |
| 2008/0058314 A1 | 3/2008 | Alonso-Alija et al. | |
| 2009/0203906 A1 | 8/2009 | Alonso-Alija et al. | |
| 2010/0317854 A1 | 12/2010 | Alonso-Alija et al. | |
| 2012/0022084 A1 | 1/2012 | Follmann et al. | |
| 2013/0190330 A1 | 7/2013 | Furstner et al. | |
| 2013/0237551 A1 | 9/2013 | Follmann et al. | |
| 2013/0267548 A1 | 10/2013 | Follmann et al. | |
| 2014/0148433 A1 | 5/2014 | Follmann et al. | |

(Continued)

FOREIGN PATENT DOCUMENTS

| | | |
|---|---|---|
| WO | 200006568 A1 | 2/2000 |
| WO | 200006569 A1 | 2/2000 |

(Continued)

OTHER PUBLICATIONS

Leis, H. J., et al. "Stable isotope labeled target compounds: preparation and use as internal standards in quantitative mass spectrometry." Curr Org Chem, (1998), vol. 2, No. 2: 131-144.

(Continued)

*Primary Examiner* — Jeffrey S Lundgren
*Assistant Examiner* — Michael J Schmitt
(74) *Attorney, Agent, or Firm* — McBee Moore & Vanik IP, LLC

(57) ABSTRACT

The present invention relates to prodrugs of 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[3-(trifluoromethyl)-pyridin-2-yl]-1H-1,2,4-triazole-5-carboxamide, 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[2-(trifluoromethyl)-phenyl]-1H-1,2,4-triazole-5-carboxamide and 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-(3-chloropyridin-2-yl)-1H-1,2,4-triazole-5-carboxamide, to processes for the preparation of such compounds, to pharmaceutical compositions containing such compounds, and to the use of such compounds or compositions for the treatment and/or prevention of diseases, in particular for the treatment and/or prevention of renal and cardiovascular diseases.

12 Claims, No Drawings

(56) References Cited

U.S. PATENT DOCUMENTS

| | | |
|---|---|---|
| 2014/0350020 A1 | 11/2014 | Follmann et al. |
| 2015/0080414 A1 | 3/2015 | Follmann et al. |
| 2016/0051518 A1 | 2/2016 | Furstner et al. |
| 2016/0122325 A1 | 5/2016 | Schmeck et al. |
| 2016/0129004 A1 | 5/2016 | Follmann et al. |
| 2017/0273977 A1 | 9/2017 | Follmann et al. |
| 2017/0313665 A1 | 11/2017 | Schmeck et al. |
| 2017/0320854 A1 | 11/2017 | Collin et al. |
| 2018/0251447 A1 | 9/2018 | Collin et al. |
| 2018/0263981 A1 | 9/2018 | Follmann et al. |
| 2019/0119251 A1 | 4/2019 | Collin-Kropelin et al. |
| 2019/0142804 A1 | 5/2019 | Neubauer et al. |
| 2019/0144422 A1 | 5/2019 | Collin-Kropelin et al. |
| 2019/0144423 A1 | 5/2019 | Collin-Kropelin et al. |
| 2019/0161453 A1 | 5/2019 | Schmeck et al. |
| 2019/0161454 A1 | 5/2019 | Collin-Kropelin et al. |
| 2019/0315720 A1 | 10/2019 | Fuerstner et al. |
| 2020/0017473 A1 | 1/2020 | Collin et al. |

FOREIGN PATENT DOCUMENTS

| | | | |
|---|---|---|---|
| WO | 0119355 A2 | 3/2001 | |
| WO | 200119776 A2 | 3/2001 | |
| WO | 200119778 A1 | 3/2001 | |
| WO | 200119780 A2 | 3/2001 | |
| WO | 200242301 A1 | 5/2002 | |
| WO | 2002070462 A1 | 9/2002 | |
| WO | 2002070510 A2 | 9/2002 | |
| WO | 2003095451 A1 | 11/2003 | |
| WO | 2005063754 A1 | 7/2005 | |
| WO | 2005105779 A1 | 11/2005 | |
| WO | 2011104322 A1 | 9/2011 | |
| WO | 2011147809 A1 | 12/2011 | |
| WO | 2012004258 A1 | 1/2012 | |
| WO | 2012028647 A1 | 3/2012 | |
| WO | 2012059549 A1 | 5/2012 | |
| WO | 2012112363 A1 | 8/2012 | |
| WO | 2016071212 A1 | 5/2016 | |
| WO | WO-2016071212 A1 * | 5/2016 | ............... A61P 7/10 |
| WO | 2017191102 A1 | 11/2017 | |
| WO | 2017191105 A1 | 11/2017 | |
| WO | 2017191107 A1 | 11/2017 | |
| WO | 2017191112 A1 | 11/2017 | |
| WO | 2017191114 A1 | 11/2017 | |
| WO | 2017191115 A1 | 11/2017 | |
| WO | 2018073144 A1 | 4/2018 | |

OTHER PUBLICATIONS

Esaki, Hiroyoshi, et al. "Efficient H/D Exchange Reactions of Alkyl-Substituted Benzene Derivatives by Means of the Pd/C-H2-D2O System." Chemistry—A European Journal, (2007), vol. 13, No. 14: 4052-4063.

Ling, Kah-Hiing John, and Robert P. Hanzlik. "Deuterium isotope effects on toluene metabolism. Product release as a rate-limiting step in cytochrome P-450 catalysis." Biochemical and biophysical research communications, (1989), vol. 160, No. 2: 844-849.

Atzrodt, Jens, et al. "The renaissance of H/D exchange." Angewandte Chemie International Edition, (2007), vol. 46, No. 41: 7744-7765.

Matoishi, Kaori, et al. "The first synthesis of both enantiomers of [α-2H] phenylacetic acid in high enantiomeric excess." Chemical Communications, (2000), vol. 16: 1519-1520.

Perrin, Charles L. "Secondary equilibrium isotope effects on acidity." Advances in Physical Organic Chemistry, (2010), vol. 44: 123, 144-146.

El Tayar, Nabil, Han van de Waterbeemd, Markoulina Gryllaki, Bernard Testa, and William F. Trager. "The lipophilicity of deuterium atoms. A comparison of shake-flask and HPLC methods." International journal of pharmaceutics 19, No. 3 (1984): Abstract.

Mutlib, Abdul E., et al. "The species-dependent metabolism of efavirenz produces a nephrotoxic glutathione conjugate in rats." Toxicology and applied pharmacology, (2000), vol. 169, No. 1: 102-113.

Kushner, D. J., et al. "Pharmacological uses and perspectives of heavy water and deuterated compounds." Canadian journal of physiology and pharmacology, (1999), vol. 77, No. 2: 79-88.

Wenthur, Cody J., et al. "Discovery of (R)-(2-fluoro-4-((-4-methoxyphenyl) ethynyl) phenyl)(3-hydroxypiperidin-1-yl) methanone (ML337), an mGlu3 selective and CNS penetrant negative allosteric modulator (NAM)." Journal of medicinal chemistry, (2013), vol. 56, No. 12: 5208-5212.

Schneider, Frank, et al. "Enhanced plasma concentration by selective deuteration of rofecoxib in rats." Arzneimittelforschung, (2006), vol. 56, No. 04: 295-300.

Maltais, François, et al. "In vitro and in vivo isotope effects with hepatitis C protease inhibitors: enhanced plasma exposure of deuterated telaprevir versus telaprevir in rats." Journal of medicinal chemistry, (2009), vol. 52, No. 24: 7993-8001.

Cross, L. C., and W. Klyne. "Report from IUPAC Commission on Nomenclature of Organic-Chemistry-Rules for Nomenclature of Organic-Chemistry. E. Stereochemistry (Recommendations 1974)." Pure and Applied Chemistry, (1976), vol. 45, No. 1: 13-30.

Berge, Stephen M., Lyle D. Bighley, and Donald C. Monkhouse. "Pharmaceutical salts." Journal of pharmaceutical sciences, (1977), vol. 66, No. 1: 1-19.

Illarionov, Boris A., et al. "Sequence of the cDNA encoding the Ca2+-activated photoprotein obelin from the hydroid polyp Obelia longissima." Gene, (1995), vol. 153, No. 2: 273-274.

Milligan, Graeme, et al. "G16 as a universal G protein adapter: implications for agonist screening strategies." Trends in pharmacological sciences, (1996), vol. 17, No. 7: 235-237.

Rizzuto, Rosario, et al. "Rapid changes of mitochondrial Ca2+ revealed by specifically targeted recombinant aequorin." Nature, (1992), vol. 358, No. 6384: 325-327.

International Search Report for PCT/EP2018/078364, dated Nov. 28, 2018.

MK. Santillan, et al., "Vasopressin in preeclampsia: a novel very early human pregnancy biomarker and clinically relevant mouse model," Hypertension, (2014),vol. 64, No. 4:852-859.

C. Taveau, et al., "Vasopressin and hydration play a major role in the development of glucose intolerance and hepatic steatosis in obese rats," Diabetologia, (2015), vol. 58, No. 5:1081-1090.

Marc Thibonnier and James M. Roberts, "Characterization of human platelet vasopressin receptors," The Journal of clinical investigation, (1985), vol. 76, No. 5:1857-1864.

Melissa A. Wasilewski, et al., "Arginine vasopressin receptor signaling and functional outcomes in heart failure," Cell Signal.,(2016), vol. 28, No. 3:224-233.

Li, Xue, et al., "Controlled and cardiac-restricted overexpression of the arginine vasopressin V1A receptor causes reversible left ventricular dysfunction through Gαq-mediated cell signaling," Circulation, (2011), vol. 124, No. 5: 572-581.

K. Rosman, et al., "Isotopic compositions of the elements 1997 (Technical Report)," Pure and Applied Chemistry, (1998), vol. 70, No. 1:217-235.

Hiroyoshi Esaki, et al., "General method of obtaining deuterium-labeled heterocyclic compounds using neutral D2O with heterogeneous Pd/C," Tetrahedron, (2006), vol. 62, No. 47:10954-10961.

J. R. Morandi, and H. B. Jensen. "Homogeneous catalytic deuteration of olefinic double bonds," The Journal of Organic Chemistry, (1969), vol. 34, No. 6:1889-1891.

N. A. Khan, "Preparation of Deuterized Raney Nickel and Selective Deuteration of the Triple Bond2," Journal of the American Chemical Society, (1952), vol. 74, No. 12:3018-3022.

S. Chandrasekhar, et al., "Flow chemistry approach for partial deuteration of alkynes: synthesis of deuterated taxol side chain," Tetrahedron letters, (2011), vol. 52, No. 30:3865-3867.

Robert P. Hanzlik, et al., "Active site dynamics of toluene hydroxylation by cytochrome P-450," The Journal of Organic Chemistry, (1990), vol. 55, No. 13:3992-3997.

Paul J. Reider, et al., "Synthesis of (R)-serine-2-d and its conversion to the broad-spectrum antibiotic fludalanine," The Journal of Organic Chemistry, (1987), vol. 52, No. 15:3326-3334.

(56) References Cited

OTHER PUBLICATIONS

Michael Jarman, et al., "The deuterium isotope effect for the α-hydroxylation of tamoxifen by rat liver microsomes accounts for the reduced genotoxicity of [D5-ethyl] tamoxifen," Carcinogenesis, (1995), vol. 16, No. 4:683-688.

Charles L. Perrin, and Yanmei Dong, "Secondary deuterium isotope effects on the acidity of carboxylic acids and phenols," Journal of the American Chemical Society, (2007), vol. 129, No. 14:4490-4497.

A. Streitwieser and H. S. Klein, "Isotope effects on acidity of deuterated formic, acetic, pivalic, and benzoic acids," Journal of the American Chemical Society, (1963), vol. 85, No. 18:2759-2763.

Charles L. Perrin, et al., "Stereochemistry of β-deuterium isotope effects on amine basicity," Journal of the American Chemical Society, (2005), vol. 127, No. 26: 9641-9647.

Charles L. Perrin, et al., "β-Deuterium isotope effects on amine basicity,"inductive" and stereochemical," Journal of the American Chemical Society, (2003), vol. 125, No. 49:15008-15009.

Amy M. Sharma, et al., "Nevirapine bioactivation and covalent binding in the skin," Chemical research in toxicology, (2013), vol. 26, No. 3:410-421.

\* cited by examiner

PRODRUGS OF SUBSTITUTED TRIAZOLE DERIVATIVES AND USES THEREOF

CROSS-REFERENCE TO RELATED APPLICATIONS

This application is the National Stage entry of International Application No. PCT/EP2018/078364, filed 17 Oct. 2018, which claims priority to European Patent Application No. 17197935.4, filed 24 Oct. 2017.

BACKGROUND

Field

The present invention relates to prodrugs of 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[3-(trifluoromethyl)pyridin-2-yl]-1H-1,2,4-triazole-5-carboxamide, 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[2-(trifluoromethyl)phenyl]-1H-1,2,4-triazole-5-carboxamide and 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-(3-chloropyridin-2-yl)-1H-1,2,4-triazole-5-carboxamide, to processes for the preparation of such compounds, to pharmaceutical compositions containing such compounds, and to the use of such compounds or compositions for the treatment and/or prevention of diseases, in particular for the treatment and/or prevention of renal and cardiovascular diseases.

Description of Related Art

Prodrugs are derivatives of an active ingredient which undergo in vivo an enzymatic and/or chemical biotransformation in one or more stages before the actual active ingredient is liberated. A prodrug residue is ordinarily used in order to improve the profile of properties of the underlying active ingredient [P. Ettmayer et al., *J. Med. Chem.* 47, 2393 (2004)]. In order to achieve an optimal profile of effects it is necessary in this connection for the design of the prodrug residue as well as the desired mechanism of liberation to conform very accurately with the individual active ingredient, the indication, the site of action and the administration route. A large number of medicaments is administered as prodrugs which exhibit an improved bioavailability by comparison with the underlying active ingredient, for example achieved by improving the physicochemical profile, specifically the solubility, the active or passive absorption properties or the tissue-specific distribution. An example which may be mentioned from the wide-ranging literature on prodrugs is: H. Bundgaard (Ed.), *Design of Prodrugs: Bioreversible derivatives for various functional groups and chemical entities*, Elsevier Science Publishers B.V., 1985.

3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[3-(trifluoromethyl)pyridin-2-yl]-1H-1,2,4-triazole-5-carboxamide (Example 4A), 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[2-(trifluoromethyl)phenyl]-1H-1,2,4-triazole-5-carboxamide (Example 6A) and 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-(3-chloropyridin-2-yl)-1H-1,2,4-triazole-5-carboxamide (Example 8A) are highly potent and selective antagonists of the V1a receptor, as disclosed in WO 2017/191102-A1 (examples 1 and 2) and WO 2017/191107-A1 (example 1).

(Example 4A)

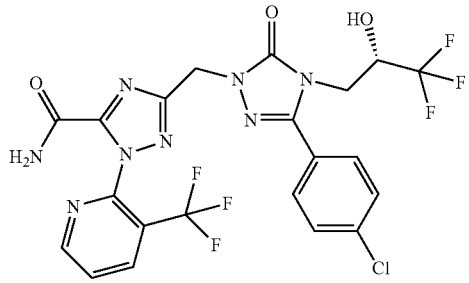

(Example 6A)

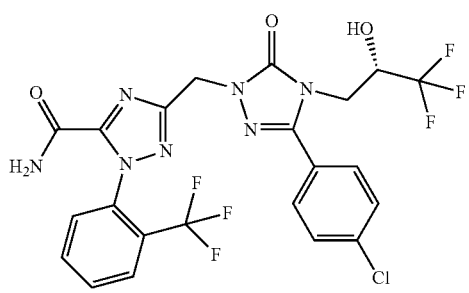

(Example 8A)

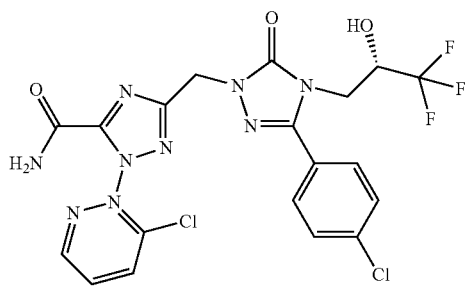

Vasopressin is a neurohormone which basically regulates water homeostasis and vascular tone. It is produced in specialized endocrine neurons in the *Nucleus supraopticus* and *N. paraventricularis* in the wall of the third ventricle (hypothalamus) and is transported from there along the neural processes into the posterior lobes of the hypophysis (neurohypophysis). There, the hormone is released into the bloodstream in response to different physiological and pathophysiological stimuli. A disturbed neurohormonal regulation essentially manifests itself in an elevation of the sympathetic tone and inappropriate activation of the renin-angiotensin-aldosterone system (RAAS). While the inhibition of these components by beta-receptor blockers on the one hand by ACE inhibitors or angiotensin-receptor blockers on the other is now an inherent part of the pharmacological treatment of cardiovascular diseases, the inappropriate elevation of vasopressin secretion is at present still not adequately treatable.

Vasopressin exerts its action mainly via binding to three receptors, which are classified as V1a, V1b and V2 receptors and which belong to the family of G protein-coupled receptors.

V2 receptors are located in the distal tubular epithelium and the epithelium of the collecting tubules in the kidney. Their activation renders these epithelia permeable to water.

This phenomenon is due to the incorporation of aquaporins (special water channels) in the luminal membrane of the epithelial cells. Consequently, pharmacological inhibition of the action of vasopressin on the V2 receptor results in increased urine excretion. Hence, drugs with V2 antagonistic activity appear particularly suitable for the treatment of all disease conditions which are associated with an overloading of the body with water.

V1b receptors (also named V3 receptors) are mainly detectable in the central nervous system. Together with corticotropin-releasing hormone (CRH), vasopressin regulates the basal and stress-induced secretion of adrenocorticotropic hormone (ACTH) via the V1b receptor.

V1a receptors are mainly located on vascular smooth muscle cells (VSMC) but also on cardiomyocytes, fibroblasts and specialized renal cells like glomerular mesangial cells or cells of the macula densa which control the release of renin [Wasilewski M A, Myers V D, Recchia F A, Feldman A M, Tilley D G, Cell Signal., 28(3), 224-233, (2016)]. The activation of VSMC V1a receptor by vasopressin gives rise to intracellular calcium release and according vasoconstriction. Therefore, stimulation of VSMC Via receptors causes increased vascular resistance and increased cardiac afterload. Cardiac output is adversely affected by V1a-mediated vasoconstriction. The increase in afterload and direct stimulation of V1a receptors on cardiomyocytes can lead to cardiac hypertrophy and remodeling including fibrosis. Mice with cardiac-specific overexpression of V1a receptor develop cardiac hypertrophy leading to dilation and left ventricular dysfunction, suggesting an essential role for V1a receptor in the development of heart failure [Li X, Chan T O, Myers V, Chowdhury I, Zhang X Q, Song J, Zhang J, Andrel J, Funakoshi H, Robbins J, Koch W J, Hyslop T, Cheung J Y, Feldman A M, Circulation.; 124, 572-581 (2011)].

V1a receptor is also expressed in the renal cortical and medullary vasculature, where it mediates vasoconstriction of renal vessels and affecting overall renal blood flow. Thus, the activation of V1a receptor can decrease renal medullary blood flow inducing further pathological processes as tissue hypoxia, reduced oxygen and accordingly energy supply for tubular transport processes as well as direct damages of mesangial and macula densa cells. It has been demonstrated that mesangial V1a receptor activation mediates TGFβ signaling and causes an increase in production of collagen IV. While this signaling contributes to extracellular matrix accumulation and remodeling in the kidney, similar signaling pathways are believed to occur in cardiac cells especially after myocardial infarction, which emphasizes the central role of V1a receptor in the development of hypertrophic and fibrotic processes in response to pathophysiological elevated vasopressin levels [Wasilewski M A, Myers V D, Recchia F A, Feldman A M, Tilley D G. Arginine vasopressin receptor signaling and functional outcomes in heart failure. Cell Signal., 28(3), 224-233 (2016)].

Since V1a receptors are mainly expressed on VSMCs and thus participating in vascular function, a link to vascular diseases as peripheral arterial disease (PAD) including claudication and critical limb ischemia as well as coronary microvascular dysfunction (CMD) is conceivable.

Apart from this, V1a receptors are also expressed on human platelets and in the liver. The meaning of platelet V1a receptors is not fully understood although vasopressin induces aggregation of human platelets via V1a receptor at high concentrations ex vivo. Therefore, inhibition of vasopressin-induced platelet aggregation by V1a receptor antagonists is a useful pharmacological ex vivo assay making use of human tissue endogenously expressing the V1a receptor [Thibonnier M, Roberts J M, *J Clin Invest.;* 76:1857-1864, (1985)].

Vasopressin stimulates gluconeogenesis and glycogenolysis via activation of the hepatic V1a receptor. Animal studies have shown that vasopressin impairs glucose tolerance which could be inhibited by a V1a receptor antagonist thereby providing a link of vasopressin receptor Via to diabetes mellitus. [Taveau C, Chollet C, Waeckel L, Desposito D, Bichet D G, Arthus M F, Magnan C, Philippe E, Paradis V, Foufelle F, Hainault I, Enhorning S, Velho G, Roussel R, Bankir L, Melander O, Bouby N. Vasopressin and hydration play a major role in the development of glucose intolerance and hepatic steatosis in obese rats. Diabetologia, 58(5), 1081-1090, (2015)].

Vasopressin was shown to contribute to the development of albuminuria and to diabetes-induced nephropathy in animal models which is consistent with epidemiological findings in humans.

It was found recently that vasopressin also seems to play a causal role in the development of preeclampsia. Chronic infusion of vasopressin during pregnancy in mice is sufficient to induce all of the major maternal and fetal phenotypes associated with human preeclampsia, including pregnancy-specific hypertension [Santillan M K, Santillan D A, Scroggins S M, Min J Y, Sandgren J A, Pearson N A, Leslie K K, Hunter S K, Zamba G K, Gibson-Corley K N, Grobe J L. Vasopressin in preeclampsia: a novel very early human pregnancy biomarker and clinically relevant mouse model. Hypertension. 64(4), 852-859, (2014)].

Vasopressin levels can be elevated in women with dysmenorrhoea (a gynecological disorder which is characterised by cyclical cramping pelvic pain) during menstruation, which appear to increase myometrial smooth muscle contraction. It was found recently that a selective vasopressin V1a receptor antagonist (relcovaptan/SR-49059) can reduce intrauterine contractions elicited by vasopressin.

For these reasons, agents which inhibit the action of vasopressin on the V1a receptor appear suitable for the treatment of several cardiovascular diseases. In particular, agents which inhibit the action of vasopressin selectively on the Via receptor offer an especially ideal profile for the treatment of otherwise normovolemic patients, i.e. those which are not eligible for decongestion by e.g. high doses of loop diuretics or V2 antagonists, and where induced aquaresis via V2 inhibition may be undesired.

Certain 4-phenyl-1,2,4-triazol-3-yl derivatives have been described in WO 2005/063754-A1 and WO 2005/105779-A1 to act as vasopressin Via receptor antagonists that are useful for the treatment of gynecological disorders, notably menstrual disorders such as dysmenorrhea.

In WO 2011/104322-A1, a particular group of bis-aryl-bonded 1,2,4-triazol-3-ones, including 5 phenyl-1,2,4-triazol-3-yl and 1-phenyl-1,2,3-triazol-4-yl derivatives thereof, has been disclosed as antagonists of vasopressin V2 and/or V1a receptors being useful for the treatment and/or prevention of cardiovascular diseases. The described compounds, however, do not show sufficient selectivity towards the V1a receptor and mostly show combined activity on both vasopressin V1a and V2 receptors. Yet, as outlined above, a high affinity as well as selectivity for the V1a receptor is a desirable prerequisite for the treatment of disease conditions where a decongestion is not desired and may lead to a dysregulated body fluid homeostasis including decreased blood plasma osmolality in otherwise normovolemic individuals.

In WO 2016/071212-A1 certain 5-(hydroxyalkyl)-1-phenyl-1,2,4-triazole derivatives have been disclosed, which act as potent antagonists of both vasopressin V1a and V2 receptors and, in addition, exhibit significantly enhanced aquaretic potency in vivo after oral application. The compounds are described to be useful for the treatment and/or prevention of cardiovascular and renal diseases. Yet, as outlined above, a high affinity as well as selectivity for the V1a receptor is a desirable prerequisite for the treatment of disease conditions where a decongestion is not desired and may lead to a dysregulated body fluid homeostasis including decreased blood plasma osmolality in otherwise normovolemic individuals.

In WO 2017/191107-A1 and WO 2017/191102-A1 certain 5-(carboxamide)-1-phenyl-1,2,4-triazole derivatives as well as in WO 2017/191114-A1 specific 5-(hydroxyalkyl)-1-heteroaryl-1,2,4-triazole derivatives have been described, which represent highly potent and selective antagonists of the V1a receptor and are particularly useful for the treatment and/or prevention of renal and cardiovascular diseases in subjects which do not suffer from fluid overload and who therefore should not be decongested.

Further novel 5-(carboxamide)-substituted, 5-(fluoroalkyl)-substituted and 3-(hydroxyalkyl)-substituted 1,2,4-triazole derivatives have been disclosed as antagonists of vasopressin V2 and/or V1a receptors in WO 2017/191105-A1, WO 2017/191112-A1, WO 2017/191115-A1 and WO 2018/073144-A1.

An activity profile with a high selectivity for the V1a receptor has a low potential to cause unwanted off-target related side effects and would also help towards reducing the amount of substance which is going to be required to achieve and maintain the desired therapeutic effect, thus limiting the potential for unacceptable side effects and/or unwanted drug-drug interactions during the treatment of patients which might already be at high risk, such as, for example, in acute or chronic heart and kidney diseases.

One technical problem to be solved according to the present invention may therefore be seen in identifying and providing new compounds that act as potent antagonists of the vasopressin V1a receptor. A further object of the invention is to identify and provide new compounds with a high affinity and selectivity vis-à-vis the vasopressin V1a receptor. The compounds are intended to avoid inducing aquaresis via V2 inhibition. The compounds are further intended to have a similar or improved therapeutic profile compared with the compounds known from the prior art, for example with respect to their in vivo properties, for example their pharmacokinetic and pharmacodynamic characteristics and/or their metabolic profile and/or their dose-activity relationship.

However, compounds of Example 4A, Example 6A and Example 8A which are highly potent and selective antagonists of the V1a receptor have a limited solubility in water and physiological media, making for example intravenous administration of the compounds of Example 4A, Example 6A and Example 8A difficult. Furthermore, the bioavailability of the compounds after oral administration of the compounds should be improved. It was therefore another object of the present invention to identify derivatives or prodrugs of the compounds of Example 4A, Example 6A and Example 8A which have an improved solubility in the media mentioned and, at the same time, allow controlled liberation of the compounds of Example 4A, Example 6A and Example 8A in the patient's body after administration and/or which have a good bioavailability after oral administration.

SUMMARY

Surprisingly, it has now been found that certain prodrugs of the compounds of Example 4A, Example 6A and Example 8A have this specific profile and renders the compounds of the present invention useful for the treatment and/or prevention of diseases, which are associated with V1a receptor activation. The compounds of the present invention are particularly useful for the treatment and/or prevention of renal and cardiovascular diseases in subjects which do not suffer from fluid overload and who therefore should not be decongested.

The invention provides compounds of the general formula (I)

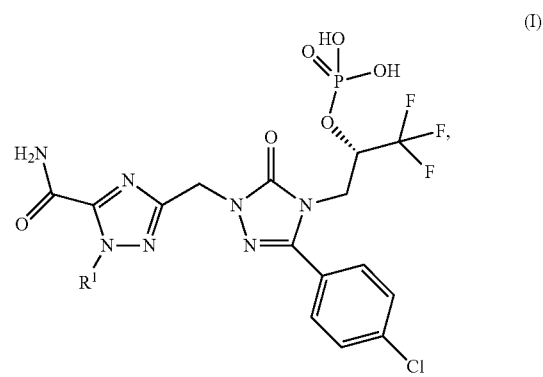

in which
$R^1$ represents a group of the formula

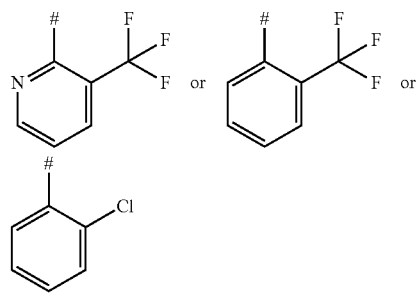

in which
\# represents the point of attachment to the 1,2,4-triazolyl-ring,
and pharmaceutically acceptable salts thereof, solvates thereof and the solvates of the salts thereof.

DETAILED DESCRIPTION OF A PREFERRED EMBODIMENT

The terms as mentioned in the present text have the following meanings:

The term "comprising" when used in the specification includes "consisting of".

In the formulae of the group which represent $R^1$, the end point of the line marked by \# does not represent a carbon atom or a $CH_2$ group, but is part of the bond to the atom to which $R^1$ is attached.

It is possible for the compounds of general formula (I) to exist as isotopic variants. The invention therefore includes one or more isotopic variant(s) of the compounds of general formula (I), particularly deuterium-containing compounds of general formula (I).

The term "Isotopic variant" of a compound or a reagent is defined as a compound exhibiting an unnatural proportion of one or more of the isotopes that constitute such a compound.

The term "Isotopic variant of the compound of general formula (I)" is defined as a compound of general formula (I) exhibiting an unnatural proportion of one or more of the isotopes that constitute such a compound.

The expression "unnatural proportion" means a proportion of such isotope which is higher than its natural abundance. The natural abundances of isotopes to be applied in this context are described in "Isotopic Compositions of the Elements 1997", Pure Appl. Chem., 70(1), 217-235, 1998.

Examples of such isotopes include stable and radioactive isotopes of hydrogen, carbon, nitrogen, oxygen, phosphorus, sulfur, fluorine, chlorine, bromine and iodine, such as $^2H$ (deuterium), $^3H$ (tritium), $^{11}C$, $^{13}C$, $^{14}C$, $^{15}N$, $^{17}O$, $^{18}O$, $^{32}P$, $^{33}P$, $^{33}S$ $^{34}S$ $^{35}S$, $^{36}S$, $^{18}F$, $^{36}Cl$, $^{82}Br$, $^{123}I$, $^{124}I$, $^{125}I$, $^{129}I$ and $^{131}I$, respectively.

With respect to the treatment and/or prevention of the disorders specified herein the isotopic variant(s) of the compounds of general formula (I) preferably contain deuterium ("deuterium-containing compounds of general formula (I)"). Isotopic variants of the compounds of general formula (I) in which one or more radioactive isotopes, such as $^3H$ or $^{14}C$, are incorporated are useful e.g. in drug and/or substrate tissue distribution studies. These isotopes are particularly preferred for the ease of their incorporation and detectability. Positron emitting isotopes such as 18F or $^{11}C$ may be incorporated into a compound of general formula (I). These isotopic variants of the compounds of general formula (I) are useful for in vivo imaging applications. Deuterium-containing and $^{13}C$-containing compounds of general formula (I) can be used in mass spectrometry analyses (H. J. Leis et al., Curr. Org. Chem., 1998, 2, 131) in the context of preclinical or clinical studies.

Isotopic variants of the compounds of general formula (I) can generally be prepared by methods known to a person skilled in the art, such as those described in the schemes and/or examples herein, by substituting a reagent for an isotopic variant of said reagent, preferably for a deuterium-containing reagent. Depending on the desired sites of deuteration, in some cases deuterium from $D_2O$ can be incorporated either directly into the compounds or into reagents that are useful for synthesizing such compounds (Esaki et al., Tetrahedron, 2006, 62, 10954; Esaki et al., Chem. Eur. J., 2007, 13, 4052). Deuterium gas is also a useful reagent for incorporating deuterium into molecules. Catalytic deuteration of olefinic bonds (H. J. Leis et al., Curr. Org. Chem., 1998, 2, 131; J. R. Morandi et al., J. Org. Chem., 1969, 34 (6), 1889) and acetylenic bonds (N. H. Khan, J. Am. Chem. Soc., 1952, 74 (12), 3018; S. Chandrasekhar et al., Tetrahedron Letters, 2011, 52, 3865) is a direct route for incorporation of deuterium. Metal catalysts (i.e. Pd, Pt, and Rh) in the presence of deuterium gas can be used to directly exchange deuterium for hydrogen in functional groups containing hydrocarbons (J. G. Atkinson et al., U.S. Pat. No. 3,966,781). A variety of deuterated reagents and synthetic building blocks are commercially available from companies such as for example C/D/N Isotopes, Quebec, Canada; Cambridge Isotope Laboratories Inc., Andover, Mass., USA; and CombiPhos Catalysts, Inc., Princeton, N.J., USA. Further information on the state of the art with respect to deuterium-hydrogen exchange is given for example in Hanzlik et al., J. Org. Chem. 55, 3992-3997, 1990; R. P. Hanzlik et al., Biochem. Biophys. Res. Commun. 160, 844, 1989; P. J. Reider et al., J. Org. Chem. 52, 3326-3334, 1987; M. Jarman et al., Carcinogenesis 16(4), 683-688, 1995; J. Atzrodt et al., Angew. Chem., Int. Ed. 2007, 46, 7744; K. Matoishi et al., Chem. Commun. 2000, 1519-1520; K. Kassahun et al., WO2012/112363.

The term "deuterium-containing compound of general formula (I)" is defined as a compound of general formula (I), in which one or more hydrogen atom(s) is/are replaced by one or more deuterium atom(s) and in which the abundance of deuterium at each deuterated position of the compound of general formula (I) is higher than the natural abundance of deuterium, which is about 0.015%. Particularly, in a deuterium-containing compound of general formula (I) the abundance of deuterium at each deuterated position of the compound of general formula (I) is higher than 10%, 20%, 30%, 40%, 50%, 60%, 70% or 80%, preferably higher than 90%, 95%, 96% or 97%, even more preferably higher than 98% or 99% at said position(s). It is understood that the abundance of deuterium at each deuterated position is independent of the abundance of deuterium at other deuterated position(s).

The selective incorporation of one or more deuterium atom(s) into a compound of general formula (I) may alter the physicochemical properties (such as for example acidity [C. L. Perrin, et al., J. Am. Chem. Soc., 2007, 129, 4490; A. Streitwieser et al., J. Am. Chem. Soc., 1963, 85, 2759;], basicity [C. L. Perrin et al., J. Am. Chem. Soc., 2005, 127, 9641; C. L. Perrin, et al., J. Am. Chem. Soc., 2003, 125, 15008; C. L. Perrin in Advances in Physical Organic Chemistry, 44, 144], lipophilicity [B. Testa et al., Int. J. Pharm., 1984, 19(3), 271]) and/or the metabolic profile of the molecule and may result in changes in the ratio of parent compound to metabolites or in the amounts of metabolites formed. Such changes may result in certain therapeutic advantages and hence may be preferred in some circumstances. Reduced rates of metabolism and metabolic switching, where the ratio of metabolites is changed, have been reported (A. E. Mutlib et al., Toxicol. Appl. Pharmacol., 2000, 169, 102; D. J. Kushner et al., Can. J. Physiol. Pharmacol., 1999, 77, 79). These changes in the exposure to parent drug and metabolites can have important consequences with respect to the pharmacodynamics, tolerability and efficacy of a deuterium-containing compound of general formula (I). In some cases deuterium substitution reduces or eliminates the formation of an undesired or toxic metabolite and enhances the formation of a desired metabolite (e.g. Nevirapine: A. M. Sharma et al., Chem. Res. Toxicol., 2013, 26, 410; Efavirenz: A. E. Mutlib et al., Toxicol. Appl. Pharmacol., 2000, 169, 102). In other cases the major effect of deuteration is to reduce the rate of systemic clearance. As a result, the biological half-life of the compound is increased. The potential clinical benefits would include the ability to maintain similar systemic exposure with decreased peak levels and increased trough levels. This could result in lower side effects and enhanced efficacy, depending on the particular compound's pharmacokinetic/pharmacodynamic relationship. ML-337 (C. J. Wenthur et al., J. Med. Chem., 2013, 56, 5208) and Odanacatib (K. Kassahun et al., WO2012/112363) are examples for this deuterium effect. Still other cases have been reported in which reduced rates of metabolism result in an increase in exposure of the drug without changing the rate of systemic clearance (e.g. Rofecoxib: F. Schneider et al., Arzneim. Forsch./Drug. Res., 2006, 56, 295; Telaprevir: F. Maltais et al., J. Med. Chem., 2009, 52, 7993). Deuterated drugs showing this effect may have reduced dosing requirements (e.g. lower number of doses or lower dosage to achieve the desired effect) and/or may produce lower metabolite loads.

A compound of general formula (I) may have multiple potential sites of attack for metabolism. To optimize the above-described effects on physicochemical properties and metabolic profile, deuterium-containing compounds of general formula (I) having a certain pattern of one or more deuterium-hydrogen exchange(s) can be selected. Particularly, the deuterium atom(s) of deuterium-containing compound(s) of general formula (I) is/are attached to a carbon atom and/or is/are located at those positions of the compound of general formula (I), which are sites of attack for metabolizing enzymes such as e.g. cytochrome $P_{450}$.

Where the plural form of the word compounds, salts, polymorphs, hydrates, solvates and the like, is used herein, this is taken to mean also a single compound, salt, polymorph, isomer, hydrate, solvate or the like.

By "stable compound' or "stable structure" is meant a compound that is sufficiently robust to survive isolation to a useful degree of purity from a reaction mixture, and formulation into an efficacious therapeutic agent.

Prodrugs are derivatives of an active ingredient. The terms "underlying active ingredient", "underlying respective drug" and "respective drug" are used synonymously in the present invention.

The compounds of the present invention optionally contain one asymmetric centre, depending upon the location and nature of the various substituents desired. It is possible that one asymmetric carbon atom is present in the (R) or (S) configuration, which can result in racemic mixtures. In certain instances, it is possible that asymmetry also be present due to restricted rotation about a given bond, for example, the central bond adjoining two substituted aromatic rings of the specified compounds. Preferred compounds are those which produce the more desirable biological activity. Separated, pure or partially purified isomers and stereoisomers or racemic mixtures of the compounds of the present invention are also included within the scope of the present invention. The purification and the separation of such materials can be accomplished by standard techniques known in the art.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, ditoluoyltartaric and camphorsulfonic acid. Mixtures of diastereoisomers can be separated into their individual diastereomers on the basis of their physical and/or chemical differences by methods known in the art, for example, by chromatography or fractional crystallisation. The optically active bases or acids are then liberated from the separated diastereomeric salts. A different process for separation of optical isomers involves the use of chiral chromatography (e.g., HPLC columns using a chiral phase), with or without conventional derivatisation, optimally chosen to maximise the separation of the enantiomers. Suitable HPLC columns using a chiral phase are commercially available, such as those manufactured by Daicel, e.g., Chiracel OD and Chiracel OJ, for example, among many others, which are all routinely selectable. Enzymatic separations, with or without derivatisation, are also useful. The optically active compounds of the present invention can likewise be obtained by chiral syntheses utilizing optically active starting materials. In order to distinguish different types of isomers from each other reference is made to IUPAC Rules Section E (Pure Appl Chem 45, 11-30, 1976).

The present invention includes all possible stereoisomers of the compounds of the present invention as single stereoisomers, or as any mixture of said stereoisomers, e.g. (R)- or (S)-isomers, in any ratio. Isolation of a single stereoisomer, e.g. a single enantiomer or a single diastereomer, of a compound of the present invention is achieved by any suitable state of the art method, such as chromatography, especially chiral chromatography, for example.

In the context of the present invention, the term "enantiomerically pure" is to be understood as meaning that the compound in question with respect to the absolute configuration of the chiral centre is present in an enantiomeric excess of more than 95%, preferably more than 97%. The enantiomeric excess, ee, is calculated here by evaluating of the corresponding HPLC chromatogram on a chiral phase using the formula below:

$$ee=[E^A(\text{area \%})-E^B(\text{area \%})]\times 100\%/[E^A(\text{area \%})+E^B(\text{area \%})]$$

($E^A$: major enantiomer, $E^B$: minor enantiomer)

The present invention also covers useful forms of the compounds of the present invention, such as metabolites, hydrates, solvates, salts, in particular pharmaceutically acceptable salts, and/or co-precipitates.

The compounds of the present invention can exist as a hydrate, or as a solvate, wherein the compounds of the present invention contain polar solvents, in particular water, methanol or ethanol for example, as structural element of the crystal lattice of the compounds. It is possible for the amount of polar solvents, in particular water, to exist in a stoichiometric or non-stoichiometric ratio. In the case of stoichiometric solvates, e.g. a hydrate, hemi-, (semi-), mono-, sesqui-, di-, tri-, tetra-, penta- etc. solvates or hydrates, respectively, are possible. The present invention includes all such hydrates or solvates. Hydrates, in particular hemihydrates (semihydrates), are preferred solvates in the context of the present invention.

Further, it is possible for the compounds of the present invention to exist in free form, e.g. as a free base, or as a free acid, or as a zwitterion, or to exist in the form of a salt. Said salt may be any salt, either an organic or inorganic addition salt, particularly any pharmaceutically acceptable organic or inorganic addition salt, which is customarily used in pharmacy, or which is used, for example, for isolating or purifying the compounds of the present invention.

The term "pharmaceutically acceptable salt" refers to an inorganic or organic addition salt of a compound of the present invention. For example, see S. M. Berge, et al. "Pharmaceutical Salts," J. Pharm. Sci. 1977, 66, 1-19.

A suitable pharmaceutically acceptable salt of a compound of the present invention which is sufficiently acidic, is an alkali metal salt, for example a sodium salt, potassium salt or lithium salt, an alkaline earth metal salt, for example a calcium salt, magnesium salt or strontium salt, or an aluminium salt or a zinc salt, or an ammonium salt derived from ammonia or from an organic primary, secondary or tertiary amine having 1 to 20 carbon atoms, such as ethylamine, diethylamine, triethylamine, ethyldiisopropylamine, monoethanolamine, diethanolamine, triethanolamine, dicyclohexylamine, dimethylaminoethanol, diethylaminoethanol, tris(hydroxymethyl)aminomethane, procaine, dibenzylamine, N-methylmorpholine, arginine, lysine, 1,2-ethylenediamine, N-methylpiperidine, N-methyl-glucamine, N,N-dimethyl-glucamine, N-ethyl-glucamine, 1,6-hexanediamine, glucosamine, sarcosine, serinol, 2-amino-1,3-propanediol, 3-amino-1,2-propanediol, 4-amino-1,2,3-butanetriol, or a salt with a quarternary ammonium ion having 1 to 20 carbon atoms, such as tetramethylammonium, tetraethylammonium, tetra(n-propyl)ammonium, tetra(n-butyl)ammonium, N-benzyl-N,N,N-trimethylammonium, choline or benzalkonium. Preference is given to a sodium salt, potassium salt, lithium salt, calcium salt or magnesium salt, most preferred is a potassium salt.

Alkali and alkaline earth metal salts of acidic compounds of the present invention are prepared by reacting the compounds of the present invention with the appropriate base via a variety of known methods.

The present invention includes all possible salts of the compounds of the present invention as single salts, or as any mixture of said salts, in any ratio.

In the present text, in particular in the Experimental Section, for the synthesis of intermediates and of examples of the present invention, when a compound is mentioned as a salt form with the corresponding base or acid, the exact stoichiometric composition of said salt form, as obtained by the respective preparation and/or purification process, is, in most cases, unknown.

Unless specified otherwise, suffixes to chemical names or structural formulae relating to salts, such as "sodium salt", "potassium salt", or "x Na$^+$", "x K$^+$", for example, mean a salt form, the stoichiometry of which salt form not being specified.

This applies analogously to cases in which synthesis intermediates or example compounds or salts thereof have been obtained, by the preparation and/or purification processes described, as solvates, such as hydrates, with (if defined) unknown stoichiometric composition.

Furthermore, the present invention includes all possible crystalline forms, or polymorphs, of the compounds of the present invention, either as single polymorph, or as a mixture of more than one polymorph, in any ratio.

Preference is given to compounds of the general formula (I) in which $R^1$ represents a group of the formula

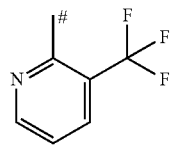

in which # represents the point of attachment to the 1,2,4-triazolyl-ring.

Preference is also given to (2S)-3-[1-({5-Carbamoyl-1-[3-(trifluoromethyl)pyridin-2-yl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate having the formula below

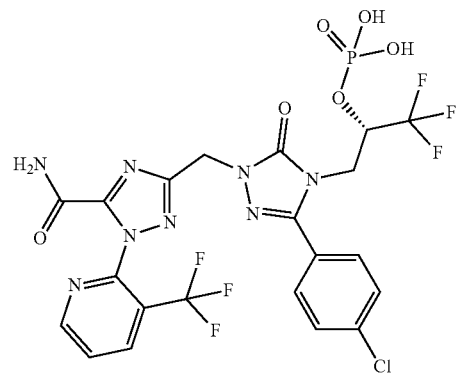 [SMILES: NC(=O)c1nc(Cn2nc(-c3ccc(Cl)cc3)n(C[C@H](OP(=O)(O)O)C(F)(F)F)c2=O)nn1-c1ncccc1C(F)(F)F]

or pharmaceutically acceptable salts thereof, solvates thereof and the solvates of the salts thereof.

Preference is also given to (2S)-3-[1-({5-Carbamoyl-1-[3-(trifluoromethyl)pyridin-2-yl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate having the formula below

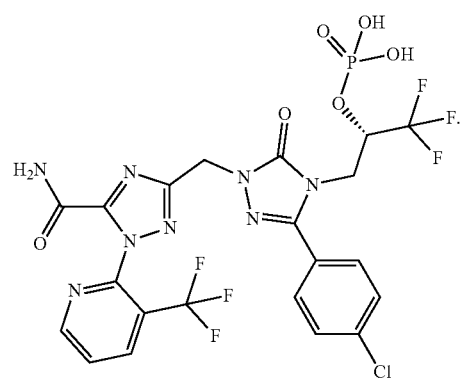 [SMILES: NC(=O)c1nc(Cn2nc(-c3ccc(Cl)cc3)n(C[C@H](OP(=O)(O)O)C(F)(F)F)c2=O)nn1-c1ncccc1C(F)(F)F]

The present invention covers the compounds of general formula (I) which are disclosed in the Example Section of this text.

The invention further provides a process for preparing the compounds of the general formula (I), or the pharmaceutically acceptable salts thereof, solvates thereof or the solvates of the salts thereof, wherein

[A] the compounds of the formula

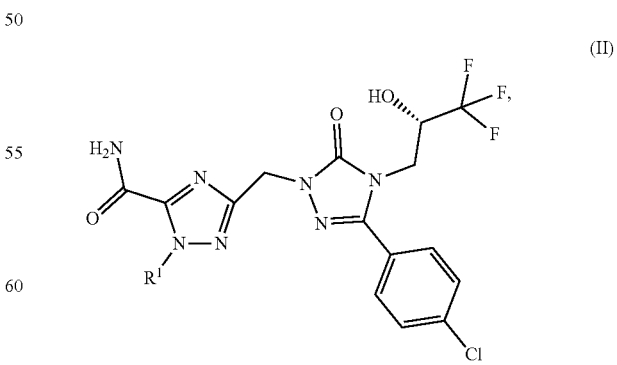

in which $R^1$ has the meaning as defined for the compounds of general formula (I) given above, are reacted in the first step with phosphorus oxychloride and in the second step are hydrolysed to give compounds of the general formula (I), or

[B] the compounds of the formula

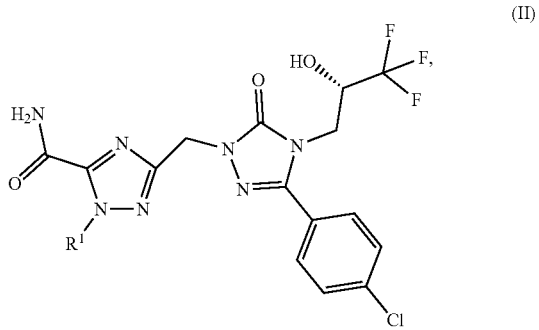

(II)

in which

R[1] has the meaning as defined for the compounds of general formula (I) given above, are reacted in the first step with tetrabenzyl diphosphate and in the second step the benzyl groups are removed under reducing conditions to give compounds of the general formula (I), optionally followed, where appropriate, by converting the compounds of the general formula (I) into their respective pharmaceutically acceptable salts thereof, solvates thereof or the solvates of the salts thereof by treatment with the corresponding solvents and/or bases.

The first step in reaction [A] is generally carried out by reacting a compound of the formula (II) with phosphorus oxychloride in an inert solvent in the presence of a base, optionally in the presence of an additive, preferably in a temperature range from −10° C. to +50° C., more preferably at 0° C. to +30° C. The reactions can be carried out at atmospheric, at elevated or at reduced pressure (for example at from 0.5 to 5 bar); in general, the reactions are carried out at atmospheric pressure.

Inert solvents are, for example, halogenated hydrocarbons such as dichloromethane or trichloromethane, ether such as diethyl ether or methyl tert-butyl ether, hydrocarbons such as benzene or toluene, or other solvents such as dioxane, dimethylformamide or tetrahydrofuran. It is also possible to use mixtures of the solvents. Preference is given to tetrahydrofuran.

Suitable bases are, for example, organic bases such as trialkylamines, for example triethylamine or diisopropylethylamine, or pyridine. Preference is given to triethylamine.

Suitable additives are, for example, 4-N,N-dimethylaminopyridine.

The second step in reaction [A] is generally carried out by adding a base or water, preferably in a temperature range from −10° C. to +50° C., more preferably at 0° C. to +30° C. The reactions can be carried out at atmospheric, at elevated or at reduced pressure (for example at from 0.5 to 5 bar); in general, the reactions are carried out at atmospheric pressure.

Suitable bases are, for example, aqueous alkali metal hydroxides solutions such as aqueous sodium hydroxide, aqueous lithium hydroxide or aqueous potassium hydroxide, or aqueous alkali metal hydrogencarbonates such as aqueous sodium hydrogencarbonate or aqueous potassium hydrogencarbonate, or aqueous alkali metal carbonates such as aqueous sodium carbonate or aqueous potassium carbonate. Preference is given to aqueous sodium hydrogencarbonate solution.

The first step in reaction [B] is generally carried out by reacting a compound of the formula (II) with tetrabenzyl diphosphate in an inert solvent in the presence of a base, preferably in a temperature range from −10° C. to +50° C., more preferably at 0° C. to +30° C. The reactions can be carried out at atmospheric, at elevated or at reduced pressure (for example at from 0.5 to 5 bar); in general, the reactions are carried out at atmospheric pressure.

Inert solvents are, for example, halogenated hydrocarbons such as dichloromethane or trichloromethane, ether such as diethyl ether or methyl tert-butyl ether, or other solvents such as dioxane, dimethylformamide or tetrahydrofuran. It is also possible to use mixtures of the solvents. Preference is given to tetrahydrofuran.

Suitable bases are, for example, potassium tert-butoxide or sodium tert-butoxide, sodium hydride, N-butyllithium, lithium diisopropylamide, bis(trimethylsilyl)sodium amide or bis(trimethylsilyl)-lithium amide, preference is given to bis(trimethylsilyl)lithium amide.

The second step in reaction [B] is generally carried with a reducing agent in an inert solvent, preferably in a temperature range from −10° C. to +50° C., more preferably at 0° C. to +30° C. The reactions can be carried out at atmospheric, at elevated or at reduced pressure (for example at from 0.5 to 5 bar); in general, the reactions are carried out at atmospheric pressure.

Inert solvents are, for example, ethanol, or mixtures of dioxane and water or tetrahydrofuran and water. Preference is given to ethanol.

Reducing agents are, for example, palladium on carbon and hydrogen, palladium dihydroxide, tin dichloride, titanium trichloride or ammonium formate. Preference is given to palladium on carbon and hydrogen.

The compounds of the formula (II) are either commercially available, known from the literature, or can be prepared from readily available starting materials by adaptation of standard methods described in the literature. Detailed procedures and literature references for preparing the starting materials can also be found in the Experimental Part in the section on the preparation of the starting materials and intermediates.

The present invention covers methods of preparing compounds of the present invention of general formula (I), said methods comprising the steps as described in the Experimental Section herein.

The schemes and procedures described below illustrate synthetic routes to the compounds of general formula (I) of the invention and are not intended to be limiting.

The preparation of the compounds of the invention may be illustrated by means of the following synthetic scheme:

Scheme 1

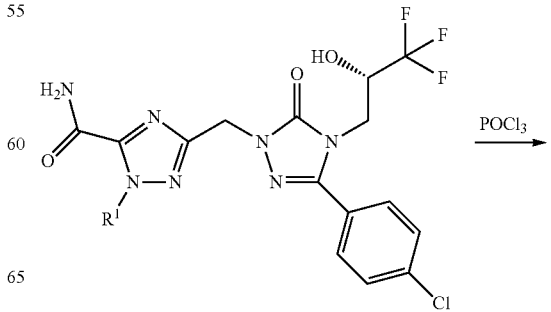

-continued

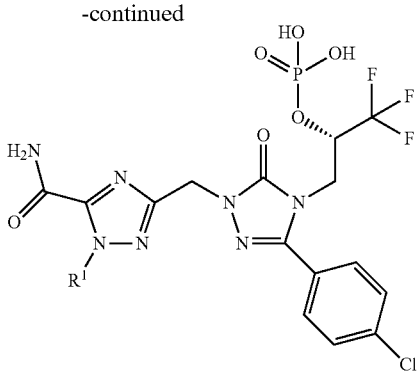

The compounds of general formula (I) of the present invention can be converted to any salt, preferably pharmaceutically acceptable salts, as described herein, by any method which is known to the person skilled in the art. Similarly, any salt of a compound of general formula (I) of the present invention can be converted into the free compound, by any method which is known to the person skilled in the art.

The compounds of the present invention have valuable pharmacological properties and can be used for the prevention and/or treatment of various diseases and disease-induced states in humans and other mammals. Compounds of general formula (I) of the present invention demonstrate a valuable pharmacological spectrum of action and pharmacokinetic profile. Compounds of the present invention have surprisingly been found to effectively inhibit the vasopressin V1a receptor and it is possible therefore that said compounds be used for the treatment and/or prevention of diseases, preferably renal and cardiovascular diseases in humans and animals.

In the context of the present invention, the term "treatment" or "treating" includes inhibiting, delaying, relieving, mitigating, arresting, reducing, or causing the regression of a disease, disorder, condition, or state, the development and/or progression thereof, and/or the symptoms thereof. The term "prevention" or "preventing" includes reducing the risk of having, contracting, or experiencing a disease, disorder, condition, or state, the development and/or progression thereof, and/or the symptoms thereof. The term prevention includes prophylaxis. Treatment or prevention of a disorder, disease, condition, or state may be partial or complete.

Throughout this document, for the sake of simplicity, the use of singular language is given preference over plural language, but is generally meant to include the plural language if not otherwise stated. For example, the expression "A method of treating a disease in a patient, comprising administering to a patient an effective amount of a compound of the general formula (I)" is meant to include the simultaneous treatment of more than one disease as well as the administration of more than one compound of the general formula (I).

The compounds of the present invention are highly potent and in particular selective antagonists of the vasopressin V1a receptor. The compounds of the invention are therefore expected to be highly valuable as therapeutic agents for the treatment and/or prevention of diseases, in particular for the treatment and/or prevention of renal and cardiovascular diseases.

As used herein, the term "vasopressin V1a receptor antagonist" refers to a compound that functions by inhibiting (partially or completely) or blocking the vasopressin V1a receptor, thereby preventing activation of the receptor by vasopressin.

In one embodiment, the underlying respective drugs of the compounds described herein are active at the V1a receptor. In another embodiment the underlying respective drugs of the compounds described herein exhibit inhibition of the V1a receptor according to the study in B-4 with an $IC_{50}<100$ nM. In another embodiment the underlying respective drugs of the compounds described herein exhibit inhibition of the V1a receptor according to the study in B-4 with an $IC_{50}<20$ nM. In another embodiment the underlying respective drugs of the compounds described herein exhibit inhibition of the V1a receptor according to the study in B-4 with an $IC_{50}<10$ nM. In another embodiment the underlying respective drugs of the compounds described herein exhibit inhibition of the V1a receptor according to the study in B-4 with an $IC_{50}<5$ nM.

In a further embodiment, the underlying respective drugs of the compounds described herein are selectively active at the V1a receptor, and are less active, substantially less active, and/or inactive at other vasopressin receptors, such as the V1b and/or V2 subtypes. In another embodiment, the underlying respective drugs of the compounds described herein are at least 10-fold selective for the V1a receptor compared to the V2 receptor as determined according to the study in B-4. In another embodiment, the underlying respective drugs of the compounds described herein are at least 15-fold selective for the V1a receptor compared to the V2 receptor as determined according to the study in B-4. In another embodiment, the underlying respective drugs of the compounds described herein are at least 20-fold selective for the V1a receptor compared to the V2 receptor as determined according to the study in B-4. In another embodiment, the underlying respective drugs of the compounds described herein are at least 30-fold selective for the V1a receptor compared to the V2 receptor as determined according to the study in B-4.

The compounds according to the invention are suitable for the treatment and/or prevention of renal diseases, in particular of acute and chronic kidney diseases, diabetic kidney diseases, and of acute and chronic renal failure. The general terms 'renal disease' or 'kidney disease' describe a class of conditions in which the kidneys fail to filter and remove waste products from the blood. There are two major forms of kidney disease: acute kidney disease (acute kidney injury, AKI) and chronic kidney disease (CKD). The compounds according to the invention may further be used for the treatment and/or prevention of sequelae of acute kidney injury arising from multiple insults such as ischemia-reperfusion injury, radiocontrast administration, cardiopulmonary bypass surgery, shock and sepsis. In the sense of the present invention, the term renal failure or renal insufficiency comprises both acute and chronic manifestations of renal insufficiency, as well as underlying or related kidney diseases such as renal hypoperfusion, intradialytic hypotension, obstructive uropathy, glomerulopathies, IgA nephropathy, glomerulonephritis, acute glomerulonephritis, glomerulosclerosis, tubulointerstitial diseases, nephropathic diseases such as primary and congenital kidney disease, nephritis, Alport syndrome, kidney inflammation, immunological kidney diseases such as kidney transplant rejection, immune complex-induced kidney diseases, nephropathy induced by toxic substances, contrast medium-induced nephropathy; minimal change glomerulonephritis (lipoid); Membranous glomerulonephritis; focal segmental glomerulosclerosis (FSGS); hemolytic uremic syndrome (HUS), amyloidosis, Goodpasture's syndrome, Wegener's granulomatosis, Purpura Schönlein-Henoch, diabetic and non-diabetic nephropathy, pyelonephritis, renal cysts, nephrosclerosis, hypertensive nephrosclerosis and nephrotic syndrome, which can be characterized diagnostically, for example, by abnormally reduced creatinine and/or water excretion, abnormally increased blood concentrations of urea, nitrogen, potassium and/or creatinine, altered activity of renal enzymes such as, for example, glutamyl synthetase, altered urine osmolarity or urine volume, increased microalbuminuria, macroalbuminuria, lesions of glomeruli and arterioles, tubular dilatation, hyperphosphataemia and/or the need for dialysis. The present invention also comprises the use of the compounds according to the invention for the treatment and/or prevention of sequelae of renal insufficiency, for example pulmonary edema, heart failure, uraemia, anaemia, electrolyte disturbances (e.g. hyperkalaemia, hyponatraemia) and disturbances in bone and carbohydrate metabolism. The compounds according to the invention are also suitable for the treatment and/or prevention of polycystic kidney disease (PCKD) and of the syndrome of inadequate ADH secretion (SIADH).

Cardiovascular diseases in this context that may be treated and/or prevented with the compounds of the invention include, but are not limited to, the following: acute and chronic heart failure including worsening chronic heart failure (or hospitalization for heart failure) and including congestive heart failure, arterial hypertension, resistant hypertension, arterial pulmonary hypertension, coronary heart disease, stable and unstable angina pectoris, atrial and ventricular arrhythmias, disturbances of atrial and ventricular rhythm and conduction disturbances, for example atrioventricular blocks of degree I-III (AVB I-III), supraventricular tachyarrhythmia, atrial fibrillation, atrial flutter, ventricular fibrillation, ventricular flutter, ventricular tachyarrhythmia, torsade-de-pointes tachycardia, atrial and ventricular extrasystoles, AV-junction extrasystoles, sick-sinus syndrome, syncopes, AV-node re-entry tachycardia and Wolff-Parkinson-White syndrome, acute coronary syndrome (ACS), autoimmune heart diseases (pericarditis, endocarditis, valvulitis, aortitis, cardiomyopathies), shock such as cardiogenic shock, septic shock and anaphylactic shock, aneurysms, Boxer cardiomyopathy (premature ventricular contraction), furthermore thromboembolic diseases and ischaemias such as peripheral perfusion disturbances, reperfusion injury, arterial and venous thromboses, myocardial insufficiency, endothelial dysfunction, micro- and macrovascular damage (vasculitis) and for preventing restenoses such as after thrombolysis therapies, percutaneous transluminal angioplasty (PTA), percutaneous transluminal coronary angioplasty (PTCA), heart transplantation and bypass operations, arteriosclerosis, disturbances of lipid metabolism, hypolipoproteinaemias, dyslipidemias, hypertriglyceridemias, hyperlipidemias and combined hyperlipidemias, hyper-cholesterolaemias, abetalipoproteinaemia, sitosterolemia, xanthomatosis, Tangier disease, adipositas, obesity, metabolic syndrome, transitory and ischemic attacks, stroke, inflammatory cardiovascular diseases, peripheral and cardiac vascular diseases, peripheral circulation disorders, spasms of the coronary arteries and peripheral arteries, and edema such as, for example, pulmonary edema, cerebral edema, renal edema and heart failure-related edema.

In the sense of the present invention, the term heart failure also includes more specific or related disease forms such as right heart failure, left heart failure, global insufficiency, ischemic cardiomyopathy, dilatative cardiomyopathy, congenital heart defects, heart valve defects, heart failure with heart valve defects, mitral valve stenosis, mitral valve insufficiency, aortic valve stenosis, aortic valve insufficiency, tricuspidal stenosis, tricuspidal insufficiency, pulmonary valve stenosis, pulmonary valve insufficiency, combined heart valve defects, heart muscle inflammation (myocarditis), chronic myocarditis, acute myocarditis, viral myocarditis, diabetic heart failure, alcohol-toxic cardiomyopathy, cardiac storage diseases, heart failure with preserved ejection fraction (HFpEF or diastolic heart failure), and heart failure with reduced ejection fraction (HFrEF or systolic heart failure).

The compounds of the present invention may be particularly useful for the treatment and/or prevention of the cardiorenal syndrome (CRS) and its various subtypes. This term embraces certain disorders of the heart and kidneys whereby acute or chronic dysfunction in one organ may induce acute or chronic dysfunction of the other.

Moreover, the compounds according to the invention may be used for the treatment and/or prevention of peripheral arterial disease (PAD) including claudication and including critical limb ischemia as well as coronary microvascular dysfunction (CMD) including CMD type 1-4, primary and secondary Raynaud's phenomenon, microcirculation disturbances, claudication, peripheral and autonomic neuropathies, diabetic microangiopathies, diabetic retinopathy, diabetic limb ulcers, gangrene, CREST syndrome, erythematous disorders, rheumatic diseases and for promoting wound healing.

Furthermore, the compounds of the invention are suitable for treating urological diseases and diseases of the male and female urogenital system such as, for example, benign prostatic syndrome (BPS), benign prostatic hyperplasia (BPH), benign prostatic enlargement (BPE), bladder outlet obstruction (BOO), lower urinary tract syndromes (LUTS), neurogenic overactive bladder (OAB), interstitial cystitis (IC), urinary incontinence (UI) such as, for example, mixed, urge, stress and overflow incontinence (MUI, UUI, SUI, OUI), pelvic pains, erectile dysfunction, dysmenorrhea and endometriosis.

The compounds according to the invention may also be used for the treatment and/or prevention of inflammatory diseases, asthmatic diseases, chronic obstructive pulmonary disease (COPD), acute respiratory distress syndrome (ARDS), acute lung injury (ALI), alpha-1-antitrypsin deficiency (AATD), pulmonary fibrosis, pulmonary emphysema (e.g. smoking-induced pulmonary emphysema) and cystic fibrosis (CF). In addition, the compounds of the invention may be used for the treatment and/or prevention of pulmonary arterial hypertension (PAH) and other forms of pulmonary hypertension (PH), including pulmonary hypertension associated with left ventricular disease, HIV infection, sickle cell anaemia, thromboembolism (CTEPH), sarcoidosis, chronic obstructive pulmonary disease (COPD) or pulmonary fibrosis.

Additionally, the compounds according to the invention may be used for the treatment and/or prevention of liver cirrhosis, ascites, diabetes mellitus and diabetic complications such as, for example, neuropathy and nephropathy.

Further, the compounds of the invention are suitable for the treatment and/or prevention of central nervous disorders such as anxiety states, depression, glaucoma, cancer such as in particular pulmonary tumors, and circadian rhythm misalignment such as jet lag and shift work.

Furthermore, the compounds according to the invention may be useful for the treatment and/or prevention of pain conditions, diseases of the adrenals such as, for example, pheochromocytoma and adrenal apoplexy, diseases of the intestine such as, for example, Crohn's disease and diarrhea, menstrual disorders such as, for example, dysmenorrhea, endometriosis, preterm labor and tocolysis.

Due to their activity and selectivity profile, the compounds of the present invention are believed to be particularly suitable for the treatment and/or prevention of acute and chronic kidney diseases including diabetic nephropathy, acute and chronic heart failure, preeclampsia, peripheral arterial disease (PAD), coronary microvascular dysfunction (CMD), Raynaud's syndrome and dysmenorrhea.

The diseases mentioned above have been well characterized in humans, but also exist with a comparable etiology in other mammals, and may be treated in those with the compounds and methods of the present invention.

Thus, the present invention further relates to the use of the compounds according to the invention for the treatment and/or prevention of diseases, especially of the aforementioned diseases.

The present invention further relates to the use of the compounds according to the invention for preparing a pharmaceutical composition for the treatment and/or prevention of diseases, especially of the aforementioned diseases.

The present invention further relates to the use of the compounds according to the invention in a method for the treatment and/or prevention of diseases, especially of the aforementioned diseases.

The present invention further relates to a method for the treatment and/or prevention of diseases, especially of the aforementioned diseases, by using an effective amount of at least one of the compounds according to the invention.

In accordance with another aspect, the present invention covers pharmaceutical combinations, in particular medicaments, comprising at least one compound of general formula (I) of the present invention and at least one or more further active ingredients, in particular for the treatment and/or prevention of diseases, especially of the aforementioned diseases.

Particularly, the present invention covers a pharmaceutical combination, which comprises:
one or more first active ingredients, in particular compounds of general formula (I) as defined aforementioned, and
one or more further active ingredients, in particular for the treatment and/or prevention of diseases, especially of the aforementioned diseases.

The term "combination" in the present invention is used as known to persons skilled in the art, it being possible for said combination to be a fixed combination, a non-fixed combination or a kit-of-parts.

A "fixed combination" in the present invention is used as known to persons skilled in the art and is defined as a combination wherein, for example, a first active ingredient, such as one or more compounds of general formula (I) of the present invention, and a further active ingredient are present together in one unit dosage or in one single entity. One example of a "fixed combination" is a pharmaceutical composition wherein a first active ingredient and a further active ingredient are present in admixture for simultaneous administration, such as in a formulation. Another example of a "fixed combination" is a pharmaceutical combination wherein a first active ingredient and a further active ingredient are present in one unit without being in admixture.

A non-fixed combination or "kit-of-parts" in the present invention is used as known to persons skilled in the art and is defined as a combination wherein a first active ingredient and a further active ingredient are present in more than one unit. One example of a non-fixed combination or kit-of-parts is a combination wherein the first active ingredient and the further active ingredient are present separately. It is possible for the components of the non-fixed combination or kit-of-parts to be administered separately, sequentially, simultaneously, concurrently or chronologically staggered.

The compounds of the present invention can be administered as the sole pharmaceutical agent or in combination with one or more other pharmaceutically active ingredients where the combination causes no unacceptable adverse effects. The present invention also covers such pharmaceutical combinations. For example, the compounds of the present invention can be combined with known agents for the treatment and/or prevention of diseases, especially of the aforementioned diseases.

In particular, the compounds of the present invention may be used in fixed or separate combination with
antithrombotic agents, for example and preferably from the group of platelet aggregation inhibitors, anticoagulants and profibrinolytic substances;
blood pressure lowering agents, for example and preferably from the group of calcium antagonists, angiotensin AII antagonists, ACE inhibitors, NEP inhibitors, vasopeptidase inhibitors, endothelin antagonists, renin inhibitors, alpha-blockers, beta-blockers, mineralocorticoid receptor antagonists and diuretics;
antidiabetic agents (hypoglycemic or antihyperglycemic agents), such as for example and preferably insulin and derivatives, sulfonylureas, biguanides, thiazolidinediones, acarbose, DPP4 inhibitors, GLP-1 analogues, or SGLT inhibitors (gliflozins);
organic nitrates and NO-donors, for example sodium nitroprusside, nitroglycerin, isosorbide mononitrate, isosorbide dinitrate, molsidomine or SIN-1, and inhalational NO;
compounds that inhibit the degradation of cyclic guanosine monophosphate (cGMP), for example inhibitors of phosphodiesterases (PDE) 1, 2, 5 and/or 9, in particular PDE-5 inhibitors such as sildenafil, vardenafil, tadalafil, udenafil, dasantafil, avanafil, mirodenafil, lodenafil, CTP-499 or PF-00489791;
positive-inotropic agents, such as for example cardiac glycosides (digoxin) and beta-adrenergic and dopaminergic agonists such as isoproterenol, adrenalin, noradrenalin, dopamine or dobut-amine;
natriuretic peptides, such as for example atrial natriuretic peptide (ANP, anaritide), B-type natriuretic peptide or brain natriuretic peptide (BNP, nesiritide), C-type natriuretic peptide (CNP) or urodilatin;
calcium sensitizers, such as for example and preferably levosimendan;
NO- and heme-independent activators of soluble guanylate cyclase (sGC), for example and with preference the compounds described in WO 01/19355, WO 01/19776, WO 01/19778, WO 01/19780, WO 02/070462 and WO 02/070510;
NO-independent, but heme-dependent stimulators of guanylate cyclase (sGC), for example and with preference the compounds described in WO 00/06568, WO 00/06569, WO 02/42301, WO 03/095451, WO 2011/147809, WO 2012/004258, WO 2012/028647 and WO 2012/059549;
agents, that stimulates the synthesis of cGMP, for example and with preference sGC modulators, for example and with preference riociguat, cinaciguat, vericiguat or BAY 1101042;
inhibitors of human neutrophil elastase (HNE), such as for example sivelestat or DX-890 (reltran);

compounds inhibiting the signal transduction cascade, in particular tyrosine and/or serine/threo-nine kinase inhibitors, such as for example nintedanib, dasatinib, nilotinib, bosutinib, regorafenib, sorafenib, sunitinib, cediranib, axitinib, telatinib, imatinib, brivanib, pazopanib, vatalanib, gefitinib, erlotinib, lapatinib, canertinib, lestaurtinib, pelitinib, semaxanib or tandutinib;

compounds influencing the energy metabolism of the heart, such as for example and preferably etomoxir, dichloroacetate, ranolazine or trimetazidine, or full or partial adenosine A1 receptor agonists as GS-9667 (previously known as CVT-3619), capadenoson and neladenoson bialanate (BAY 1067197);

compounds influencing the heart rate, such as for example and preferably ivabradine;

cardiac myosin activators, such as for example and preferably omecamtiv mecarbil (CK-1827452);

anti-inflammatory drugs such as non-steroidal anti-inflammatory drugs (NSAIDs) including acetylsalicylic acid (aspirin), ibuprofen and naproxen, glucocorticoids such as for example and preferably prednison, prednisolon, methylprednisolon, triamcinolon, dexamethason, beclomethason, betamethason, flunisolid, budesonid or fluticason, or 5-aminosalicylic acid derivatives, leukotriene antagonists, TNF-alpha inhibitors and chemokine receptor antagonists such as CCR1, 2 and/or 5 inhibitors;

fat metabolism altering agents, for example and preferably from the group of thyroid receptor agonists, cholesterol synthesis inhibitors, such as for example and preferably HMG-CoA-reductase or squalene synthesis inhibitors, ACAT inhibitors, CETP inhibitors, MTP inhibitors, PPAR-alpha, PPAR-gamma and/or PPAR-delta agonists, cholesterol absorption inhibitors, lipase inhibitors, polymeric bile acid adsorbers, bile acid reabsorption inhibitors and lipoprotein(a) antagonists.

Antithrombotic agents are preferably to be understood as compounds from the group of platelet aggregation inhibitors, anticoagulants and profibrinolytic substances.

In a preferred embodiment of the invention, the compounds according to the invention are administered in combination with a platelet aggregation inhibitor, for example and preferably aspirin, clopidogrel, ticlopidine or dipyridamole.

In a preferred embodiment of the invention, the compounds according to the invention are administered in combination with a thrombin inhibitor, for example and preferably ximelagatran, dabigatran, melagatran, bivalirudin or enoxaparin.

In a preferred embodiment of the invention, the compounds according to the invention are administered in combination with a GPIIb/IIIa antagonist, for example and preferably tirofiban or abciximab.

In a preferred embodiment of the invention, the compounds according to the invention are administered in combination with a factor Xa inhibitor, for example and preferably rivaroxaban, apixaban, otamixaban, fidexaban, razaxaban, fondaparinux, idraparinux, DU-176b, PMD-3112, YM-150, KFA-1982, EMD-503982, MCM-17, MLN-1021, DX 9065a, DPC 906, JTV 803, SSR-126512 or SSR-128428.

In a preferred embodiment of the invention, the compounds according to the invention are administered in combination with heparin or a low molecular weight (LMW) heparin derivative. In a preferred embodiment of the invention, the compounds according to the invention are administered in combination with a vitamin K antagonist, for example and preferably coumarin. Blood pressure lowering agents are preferably to be understood as compounds from the group of calcium antagonists, angiotensin AII antagonists, ACE inhibitors, NEP inhibitors, vasopeptidase inhibitors, endothelin antagonists, renin inhibitors, alpha-blockers, beta-blockers, mineralocorticoid receptor antagonists and diuretics.

In a preferred embodiment of the invention, the compounds according to the invention are administered in combination with a calcium antagonist, for example and preferably nifedipine, amlodipine, verapamil or diltiazem.

In a preferred embodiment of the invention, the compounds according to the invention are administered in combination with an alpha-1-receptor blocker, for example and preferably prazosin or tamsulosin.

In a preferred embodiment of the invention, the compounds according to the invention are administered in combination with a beta-blocker, for example and preferably propranolol, atenolol, timolol, pindolol, alprenolol, oxprenolol, penbutolol, bupranolol, metipranolol, nadolol, mepindolol, carazolol, sotalol, metoprolol, betaxolol, celiprolol, bisoprolol, carteolol, esmolol, labetalol, carvedilol, adaprolol, landiolol, nebivolol, epanolol or bucindolol.

In a preferred embodiment of the invention, the compounds according to the invention are administered in combination with an angiotensin AII receptor antagonist, for example and preferably losartan, candesartan, valsartan, telmisartan, irbesartan, olmesartan, eprosartan, embursartan or azilsartan.

In a preferred embodiment of the invention, the compounds according to the invention are administered in combination with a vasopeptidase inhibitor or inhibitor of neutral endopeptidase (NEP), such as for example and preferably sacubitril, omapatrilat or AVE-7688.

In a preferred embodiment of the invention, the compounds according to the invention are administered in combination with a dual angiotensin AII receptor antagonist/NEP inhibitor (ARNI), for example and preferably LCZ696.

In a preferred embodiment of the invention, the compounds according to the invention are administered in combination with an ACE inhibitor, for example and preferably enalapril, captopril, lisinopril, ramipril, delapril, fosinopril, quinopril, perindopril, benazepril or trandopril.

In a preferred embodiment of the invention, the compounds according to the invention are administered in combination with an endothelin antagonist, for example and preferably bosentan, darusentan, ambrisentan, tezosentan, sitaxsentan, avosentan, macitentan or atrasentan.

In a preferred embodiment of the invention, the compounds according to the invention are administered in combination with a renin inhibitor, for example and preferably aliskiren, SPP-600 or SPP-800.

In a preferred embodiment of the invention, the compounds according to the invention are administered in combination with a mineralocorticoid receptor antagonist, for example and preferably finerenone, spironolactone, canrenone, potassium canrenoate, eplerenone, esaxerenone (CS-3150), or apararenone (MT-3995), CS-3150, or MT-3995.

In a preferred embodiment of the invention, the compounds according to the invention are administered in combination with a diuretic, such as for example and preferably furosemide, bumetanide, piretanide, torsemide, bendroflumethiazide, chlorothiazide, hydrochlorothiazide, xipamide, indapamide, hydroflumethiazide, methyclothiazide, polythiazide, trichloromethiazide, chlorthalidone, metolazone, quinethazone, acetazolamide, dichlorophenamide, methazolamide, glycerine, isosorbide, mannitol, amiloride or triamterene.

Fat metabolism altering agents are preferably to be understood as compounds from the group of CETP inhibitors, thyroid receptor agonists, cholesterol synthesis inhibitors such as HMG-CoA-reductase or squalene synthesis inhibitors, ACAT inhibitors, MTP inhibitors, PPAR-alpha, PPAR-gamma and/or PPAR-delta agonists, cholesterol absorption inhibitors, polymeric bile acid adsorbers, bile acid reabsorption inhibitors, lipase inhibitors and lipoprotein(a) antagonists.

In a preferred embodiment of the invention, the compounds according to the invention are administered in combination with a CETP inhibitor, for example and preferably dalcetrapib, anacetrapib, BAY 60-5521 or CETP-vaccine (Avant).

In a preferred embodiment of the invention, the compounds according to the invention are administered in combination with a thyroid receptor agonist, for example and preferably D-thyroxin, 3,5,3'-triiodothyronin (T3), CGS 23425 or axitirome (CGS 26214).

In a preferred embodiment of the invention, the compounds according to the invention are administered in combination with an HMG-CoA-reductase inhibitor from the class of statins, for example and preferably lovastatin, simvastatin, pravastatin, fluvastatin, atorvastatin, rosuvastatin or pitavastatin.

In a preferred embodiment of the invention, the compounds according to the invention are administered in combination with a squalene synthesis inhibitor, for example and preferably BMS-188494 or TAK-475.

In a preferred embodiment of the invention, the compounds according to the invention are administered in combination with an ACAT inhibitor, for example and preferably avasimibe, melinamide, pactimibe, eflucimibe or SMP-797.

In a preferred embodiment of the invention, the compounds according to the invention are administered in combination with an MTP inhibitor, for example and preferably implitapide, R-103757, BMS-201038 or JTT-130.

In a preferred embodiment of the invention, the compounds according to the invention are administered in combination with a PPAR-gamma agonist, for example and preferably pioglitazone or rosiglitazone.

In a preferred embodiment of the invention, the compounds according to the invention are administered in combination with a PPAR-delta agonist, for example and preferably GW 501516 or BAY 68-5042.

In a preferred embodiment of the invention, the compounds according to the invention are administered in combination with a cholesterol absorption inhibitor, for example and preferably ezetimibe, tiqueside or pamaqueside.

In a preferred embodiment of the invention, the compounds according to the invention are administered in combination with a lipase inhibitor, for example and preferably orlistat.

In a preferred embodiment of the invention, the compounds according to the invention are administered in combination with a polymeric bile acid adsorber, for example and preferably cholestyr-amine, colestipol, colesolvam, CholestaGel or colestimide.

In a preferred embodiment of the invention, the compounds according to the invention are administered in combination with a bile acid reabsorption inhibitor, for example and preferably ASBT(=IBAT) inhibitors such as AZD-7806, S-8921, AK-105, BARI-1741, SC-435 or SC-635.

In a preferred embodiment of the invention, the compounds according to the invention are administered in combination with a lipoprotein(a) antagonist, for example and preferably gemcabene calcium (CI-1027) or nicotinic acid.

In a preferred embodiment of the invention, the compounds according to the invention are administered in combination with a TGFbeta antagonist, by way of example and with preference pirfenidone or fresolimumab.

In a preferred embodiment of the invention, the compounds according to the invention are administered in combination with HIF-PH inhibitors, by way of example and with preference molidustat or roxadustat.

In a preferred embodiment of the invention, the compounds according to the invention are administered in combination with a CCR2 antagonist, by way of example and with preference CCX-140.

In a preferred embodiment of the invention, the compounds according to the invention are administered in combination with a TNFalpha antagonist, by way of example and with preference adalimumab.

In a preferred embodiment of the invention, the compounds according to the invention are administered in combination with a galectin-3 inhibitor, by way of example and with preference GCS-100.

In a preferred embodiment of the invention, the compounds according to the invention are administered in combination with a BMP-7 agonist, by way of example and with preference THR-184.

In a preferred embodiment of the invention, the compounds according to the invention are administered in combination with a p53 modulator, by way of example and with preference QPI-1002.

In a preferred embodiment of the invention, the compounds according to the invention are administered in combination with a NOX1/4 inhibitor, by way of example and with preference GKT-137831.

In a preferred embodiment of the invention, the compounds according to the invention are administered in combination with a medicament which affects the vitamin D metabolism, by way of example and with preference cholecalciferol or paracalcitol.

In a preferred embodiment of the invention, the compounds according to the invention are administered in combination with a cytostatic agent, by way of example and with preference cyclophosphamide.

In a preferred embodiment of the invention, the compounds according to the invention are administered in combination with an immunosuppressive agent, by way of example and with preference ciclosporin.

In a preferred embodiment of the invention, the compounds according to the invention are administered in combination with a phosphate binder, by way of example and with preference sevelamer or lanthanum carbonate.

In a preferred embodiment of the invention, the compounds according to the invention are administered in combination with a calcimimetic for therapy of hyperparathyroidism.

In a preferred embodiment of the invention, the compounds according to the invention are administered in combination with agents for iron deficit therapy, by way of example and with preference iron products.

In a preferred embodiment of the invention, the compounds according to the invention are administered in combination with agents for the therapy of hyperurikaemia, by way of example and with preference allopurinol or rasburicase.

In a preferred embodiment of the invention, the compounds according to the invention are administered in combination with glycoprotein hormone for the therapy of anaemia, by way of example and with preference erythropoietin.

In a preferred embodiment of the invention, the compounds according to the invention are administered in combination with biologics for immune therapy, by way of example and with preference abatacept, rituximab, eculizumab or belimumab.

In a preferred embodiment of the invention, the compounds according to the invention are administered in combination with Jak inhibitors, by way of example and with preference ruxolitinib, tofacitinib, baricitinib, CYT387, GSK2586184, lestaurtinib, pacritinib (SB1518) or TG101348.

In a preferred embodiment of the invention, the compounds according to the invention are administered in combination with prostacyclin analogs for therapy of microthrombi.

In a preferred embodiment of the invention, the compounds according to the invention are administered in combination with an alkali therapy, by way of example and with preference sodium bicarbonate.

In a preferred embodiment of the invention, the compounds according to the invention are administered in combination with an mTOR inhibitor, by way of example and with preference everolimus or rapamycin.

In a preferred embodiment of the invention, the compounds according to the invention are administered in combination with an NHE3 inhibitor, by way of example and with preference AZD1722.

In a preferred embodiment of the invention, the compounds according to the invention are administered in combination with an eNOS modulator, by way of example and with preference sapropterin.

In a preferred embodiment of the invention, the compounds according to the invention are administered in combination with a CTGF inhibitor, by way of example and with preference FG-3019.

In a preferred embodiment of the invention, the compounds according to the invention are administered in combination with antidiabetics (hypoglycemic or antihyperglycemic agents), such as for example and preferably insulin and derivatives, sulfonylureas such as tolbutamide, carbutamide, acetohexamide, chlorpropamide, glipizide, gliclazide, glibenclamide, glyburide, glibornuride, gliquidone, glisoxepide, glyclopyramide, glimepiride, JB253 and JB558, meglitinides such as repaglinide and nateglinide, biguanides such as metformin and buformin, thiazolidinediones such as rosiglitazone and pioglitazone, alpha-glucosidase inhibitors such as miglitol, acarbose and voglibose, DPP4 inhibitors such as vildagliptin, sitagliptin, saxagliptin, linagliptin, alogliptin, septagliptin and teneligliptin, GLP-1 analogues such as exenatide (also exendin-4, liraglutide, lixisenatide and taspoglutide, or SGLT inhibitors (gliflozins) such as canagliflozin, dapagliflozin and empagliflozin.

In a particularly preferred embodiment, the compounds of the present invention are administered in combination with one or more additional therapeutic agents selected from the group consisting of diuretics, angiotensin AII antagonists, ACE inhibitors, beta-receptor blockers, mineralocorticoid receptor antagonists, antidiabetics, organic nitrates and NO donors, activators and stimulators of the soluble guanylate cyclase (sGC), and positive-inotropic agents.

In a further particularly preferred embodiment, the compounds of the present invention are administered in combination with one or more additional therapeutic agents selected from the group consisting of diuretics, angiotensin AII antagonists, ACE inhibitors, beta-receptor blockers, mineralocorticoid receptor antagonists, antidiabetics, organic nitrates and NO donors, activators and stimulators of the soluble guanylate cyclase (sGC), positive-inotropic agents, antiinflammatory agents, immunosuppressive agents, phosphate binders and/or compounds which modulate vitamin D metabolism.

Thus, in a further embodiment, the present invention relates to pharmaceutical compositions comprising at least one of the compounds according to the invention and one or more additional therapeutic agents for the treatment and/or prevention of diseases, especially of the aforementioned diseases.

Furthermore, the compounds of the present invention may be utilized, as such or in compositions, in research and diagnostics, or as analytical reference standards and the like, which are well known in the art.

When the compounds of the present invention are administered as pharmaceuticals, to humans and other mammals, they can be given per se or as a pharmaceutical composition containing, for example, 0.1% to 99.5% (more preferably, 0.5% to 90%) of active ingredient in combination with one or more pharmaceutically acceptable excipients.

Thus, in another aspect, the present invention relates to pharmaceutical compositions comprising at least one of the compounds according to the invention, conventionally together with one or more inert, non-toxic, pharmaceutically acceptable excipients, and to the use thereof for the treatment and/or prevention of diseases, especially of the aforementioned diseases.

It is possible for the compounds according to the invention to have systemic and/or local activity. For this purpose, they can be administered in a suitable manner, such as, for example, via the oral, parenteral, pulmonary, nasal, sublingual, lingual, buccal, rectal, vaginal, dermal, transdermal, conjunctival, otic route or as an implant or stent.

For these administration routes, it is possible for the compounds according to the invention to be administered in suitable administration forms.

For oral administration, it is possible to formulate the compounds according to the invention to dosage forms known in the art that deliver the compounds of the invention rapidly and/or in a modified manner, such as, for example, tablets (uncoated or coated tablets, for example with enteric or controlled release coatings that dissolve with a delay or are insoluble), orally-disintegrating tablets, films/wafers, films/lyophylisates, capsules (for example hard or soft gelatine capsules), sugar-coated tablets, granules, pellets, powders, emulsions, suspensions, aerosols or solutions. It is possible to incorporate the compounds according to the invention in crystalline and/or amorphised and/or dissolved form into said dosage forms.

Parenteral administration can be effected with avoidance of an absorption step (for example intravenous, intraarterial, intracardial, intraspinal or intralumbal) or with inclusion of absorption (for example intramuscular, subcutaneous, intracutaneous, percutaneous or intraperitoneal). Administration forms which are suitable for parenteral administration are, inter alia, preparations for injection and infusion in the form of solutions, suspensions, emulsions, lyophylisates or sterile powders.

Examples which are suitable for other administration routes are pharmaceutical forms for inhalation [inter alia powder inhalers, nebulizers], nasal drops, nasal solutions, nasal sprays; tablets/films/wafers/capsules for lingual, sublingual or buccal administration; suppositories; eye drops, eye ointments, eye baths, ocular inserts, ear drops, ear sprays, ear powders, ear-rinses, ear tampons; vaginal capsules, aqueous suspensions (lotions, mixturae agitandae), lipophilic suspensions, emulsions, ointments, creams, transdermal therapeutic systems (such as, for example, patches), milk, pastes, foams, dusting powders, implants or stents.

The compounds according to the invention can be incorporated into the stated administration forms. This can be effected in a manner known per se by mixing with pharmaceutically suitable excipients. Pharmaceutically suitable excipients include, inter alia,

- fillers and carriers (for example cellulose, microcrystalline cellulose (such as, for example, Avicel®), lactose, mannitol, starch, calcium phosphate (such as, for example, Di-Cafos®)),
- ointment bases (for example petroleum jelly, paraffins, triglycerides, waxes, wool wax, wool wax alcohols, lanolin, hydrophilic ointment, polyethylene glycols),
- bases for suppositories (for example polyethylene glycols, cacao butter, hard fat),
- solvents (for example water, ethanol, iso-propanol, glycerol, propylene glycol, medium chain-length triglycerides fatty oils, liquid polyethylene glycols, paraffins),
- surfactants, emulsifiers, dispersants or wetters (for example sodium dodecyl sulfate), lecithin, phospholipids, fatty alcohols (such as, for example, Lanette®), sorbitan fatty acid esters (such as, for example, Span®), polyoxyethylene sorbitan fatty acid esters (such as, for example, Tween®), polyoxyethylene fatty acid glycerides (such as, for example, Cremophor®), polyoxyethylene fatty acid esters, polyoxyethylene fatty alcohol ethers, glycerol fatty acid esters, poloxamers (such as, for example, Pluronic®),
- buffers, acids and bases (for example phosphates, carbonates, citric acid, acetic acid, hydrochloric acid, sodium hydroxide solution, ammonium carbonate, trometamol, triethanolamine),
- isotonicity agents (for example glucose, sodium chloride),
- adsorbents (for example highly-disperse silicas),
- viscosity-increasing agents, gel formers, thickeners and/or binders (for example polyvinylpyrrolidone, methylcellulose, hydroxypropylmethylcellulose, hydroxypropylcellulose, carboxymethylcellulose-sodium, starch, carbomers, polyacrylic acids (such as, for example, Carbopol®); alginates, gelatine),
- disintegrants (for example modified starch, carboxymethylcellulose-sodium, sodium starch glycolate (such as, for example, Explotab©), cross-linked polyvinylpyrrolidone, croscarmellose-sodium (such as, for example, AcDiSol®)),
- flow regulators, lubricants, glidants and mould release agents (for example magnesium stearate, stearic acid, talc, highly-disperse silicas (such as, for example, Aerosil®)),
- coating materials (for example sugar, shellac) and film formers for films or diffusion membranes which dissolve rapidly or in a modified manner (for example polyvinylpyrrolidones (such as, for example, Kollidon®), polyvinyl alcohol, hydroxypropylmethylcellulose, hydroxypropylcellulose, ethylcellulose, hydroxypropylmethylcellulose phthalate, cellulose acetate, cellulose acetate phthalate, polyacrylates, polymethacrylates such as, for example, Eudragit®)),
- capsule materials (for example gelatine, hydroxypropylmethylcellulose),
- synthetic polymers (for example polylactides, polyglycolides, polyacrylates, polymethacrylates (such as, for example, Eudragit®), polyvinylpyrrolidones (such as, for example, Kollidon®), polyvinyl alcohols, polyvinyl acetates, polyethylene oxides, polyethylene glycols and their copolymers and blockcopolymers),
- plasticizers (for example polyethylene glycols, propylene glycol, glycerol, triacetine, triacetyl citrate, dibutyl phthalate),
- penetration enhancers,
- stabilisers (for example antioxidants such as, for example, ascorbic acid, ascorbyl palmitate, sodium ascorbate, butylhydroxyanisole, butylhydroxytoluene, propyl gallate),
- preservatives (for example parabens, sorbic acid, thiomersal, benzalkonium chloride, chlorhexidine acetate, sodium benzoate),
- colourants (for example inorganic pigments such as, for example, iron oxides, titanium dioxide),
- flavourings, sweeteners, flavour- and/or odour-masking agents.

The present invention furthermore relates to a pharmaceutical composition which comprises at least one compound according to the invention, conventionally together with one or more pharmaceutically suitable excipient(s), and to their use according to the present invention. Based upon standard laboratory techniques known to evaluate compounds useful for the treatment of cardiovascular and renal disorders, by standard toxicity tests and by standard pharmacological assays for the determination of treatment of the conditions identified above in mammals, and by comparison of these results with the results of known active ingredients or medicaments that are used to treat these conditions, the effective dosage of the compounds of the present invention can readily be determined for treatment of each desired indication. The amount of the active ingredient to be administered in the treatment of one of these conditions can vary widely according to such considerations as the particular compound and dosage unit employed, the mode of administration, the period of treatment, the age and sex of the patient treated, and the nature and extent of the condition treated.

The total amount of the active ingredient to be administered will generally range from about 0.001 mg/kg to about 200 mg/kg body weight per day, and preferably from about 0.01 mg/kg to about 20 mg/kg body weight per day. Clinically useful dosing schedules will range from one to three times a day dosing to once every four weeks dosing. In addition, it is possible for "drug holidays", in which a patient is not dosed with a drug for a certain period of time, to be beneficial to the overall balance between pharmacological effect and tolerability. It is possible for a unit dosage to contain from about 0.5 mg to about 1500 mg of active ingredient, and can be administered one or more times per day or less than once a day. The average daily dosage for administration by injection, including intravenous, intramuscular, subcutaneous and parenteral injections, and use of infusion techniques will preferably be from 0.01 to 200 mg/kg of total body weight. Illustratively, the compound of the present invention may be administered parenterally at a dose of about 0.001 mg/kg to about 10 mg/kg, preferably of about 0.01 mg/kg to about 1 mg/kg of body weight. In oral administration, an exemplary dose range is about 0.01 to 100 mg/kg, preferably about 0.01 to 20 mg/kg, and more preferably about 0.1 to 10 mg/kg of body weight. Ranges intermediate to the above-recited values are also intended to be part of the invention.

Of course the specific initial and continuing dosage regimen for each patient will vary according to the nature and severity of the condition as determined by the attending diagnostician, the activity of the specific compound employed, the age and general condition of the patient, time of administration, route of administration, rate of excretion of the drug, drug combinations, and the like. The desired mode of treatment and number of doses of a compound of the present invention or a pharmaceutically acceptable salt or ester or composition thereof can be ascertained by those skilled in the art using conventional treatment tests.

The following exemplary embodiments illustrate the invention. The invention is not restricted to the examples.

The percentages in the following tests and examples are, unless stated otherwise, by weight; parts are by weight. Solvent ratios, dilution ratios and concentrations reported for liquid/liquid solutions are each based on volume.

EXPERIMENTAL SECTION

Experimental Section—General Part

NMR peak forms are stated as they appear in the spectra, possible higher order effects have not been considered.

Chemical names were generated using the ACD/Name software from ACD/Labs. In some cases generally accepted names of commercially available reagents were used in place of ACD/Name generated names.

The following table 1 lists the abbreviations used in this paragraph and in the Examples section as far as they are not explained within the text body. Other abbreviations have their meanings customary per se to the skilled person.

TABLE 1

Abbreviations
The following table lists the abbreviations used herein.

| Abbreviation | Meaning |
|---|---|
| abs | absolut |
| br | broad ($^1$H-NMR signal) |
| conc. | concentrated |
| CI | chemical ionisation |
| d | doublet ($^1$H-NMR signal) |
| d | day(s) |
| DAD | diode array detector |
| DCM | dichloromethane |
| dd | double-doublet |
| Dess-Martin periodinane | 1,1,1-Triacetoxy-1,1-dihydro-1,2-benziodoxol-3(1H)-one |
| DMSO | dimethylsulfoxide |
| ESI | electrospray (ES) ionisation |
| h | hour(s) |
| HATU | 1-[Bis(dimethylamino)methylene]-1H-1,2,3-triazolo[4,5-b]pyridinium 3-oxide hexafluorophosphate |
| HPLC | high performance liquid chromatography |
| LC-MS | liquid chromatography mass spectrometry |
| m | multiplet ($^1$H-NMR signal) |
| min | minute(s) |
| MS | mass spectrometry |
| MTBE | methyl-tert-butylether |
| NMR | nuclear magnetic resonance spectroscopy: chemical shifts (δ) are given in ppm. The chemical shifts were corrected by setting the DMSO signal to 2.50 ppm unless otherwise stated. |
| of th. | of theory |
| PDA | Photo Diode Array |
| $R_t$ | retention time (as measured either with HPLC or UPLC) in minutes |
| s | singlet ($^1$H-NMR signal) |
| SFC | Supercritical Fluid Chromatography |
| SQD | Single-Quadrupole-Detector |
| t | triplet ($^1$H-NMR signal) |

TABLE 1-continued

Abbreviations
The following table lists the abbreviations used herein.

| Abbreviation | Meaning |
|---|---|
| td | triple-doublet ($^1$H-NMR signal) |
| TFA | trifluoroacetic acid |
| THF | tetrahydrofuran |
| UPLC | ultra performance liquid chromatography |

The various aspects of the invention described in this application are illustrated by the following examples which are not meant to limit the invention in any way.

The example testing experiments described herein serve to illustrate the present invention and the invention is not limited to the examples given.

All reagents, for which the synthesis is not described in the experimental part, are either commercially available, or are known compounds or may be formed from known compounds by known methods by a person skilled in the art.

The compounds and intermediates produced according to the methods of the invention may require purification. Purification of organic compounds is well known to the person skilled in the art and there may be several ways of purifying the same compound. In some cases, no purification may be necessary. In some cases, the compounds may be purified by crystallization. In some cases, impurities may be stirred out using a suitable solvent. In some cases, the compounds may be purified by chromatography, particularly flash column chromatography, using for example prepacked silica gel cartridges, e.g. Biotage SNAP cartidges KP-Sil® or KP-NH® in combination with a Biotage autopurifier system (SP4® or Isolera Four®) and eluents such as gradients of hexane/ethyl acetate or DCM/methanol. In some cases, the compounds may be purified by preparative HPLC using for example a Waters autopurifier equipped with a diode array detector and/or on-line electrospray ionization mass spectrometer in combination with a suitable prepacked reverse phase column and eluents such as gradients of water and acetonitrile which may contain additives such as trifluoroacetic acid, formic acid or aqueous ammonia.

In some cases, purification methods as described above can provide those compounds of the present invention which possess a sufficiently basic or acidic functionality in the form of a salt, such as, in the case of a compound of the present invention which is sufficiently basic, a trifluoroacetate or formate salt for example, or, in the case of a compound of the present invention which is sufficiently acidic, an ammonium salt for example. A salt of this type can either be transformed into its free base or free acid form, respectively, by various methods known to the person skilled in the art, or be used as salts in subsequent biological assays. It is to be understood that the specific form (e.g. salt, free base etc.) of a compound of the present invention as isolated and as described herein is not necessarily the only form in which said compound can be applied to a biological assay in order to quantify the specific biological activity.

In the case of the synthesis intermediates and working examples of the invention described hereinafter, any compound specified in the form of a salt of the corresponding base or acid is generally a salt of unknown exact stoichiometric composition, as obtained by the respective preparation and/or purification process. Unless specified in more detail, additions to names and structural formulae, such as "hydrochloride", "trifluoroacetate", "sodium salt", "potassium salt", "dipotassium salt", "hydrogen phosphate", "phosphate" or "x HCl", "x CF₃COOH", "x Na*", "x K+", "x Ca²+", "x Mg²+" should not therefore be understood in a stoichiometric sense in the case of such salts, but have merely descriptive character with regard to the salt-forming components present therein.

This applies correspondingly if synthesis intermediates or working examples or salts thereof were obtained in the form of solvates, for example hydrates, of unknown stoichiometric composition (if they are of a defined type) by the preparation and/or purification processes described.

HPLC and LC-MS Methods:

Method 1 (LC-MS)

Instrument: Waters ACQUITY SQD UPLC System; Column: Waters Acquity UPLC HSS T3 1.8µ 50×1 mm; eluent A: 1 l water+0.25 ml 99% formic acid, eluent B: 1 l acetonitrile+0.25 ml 99% formic acid; gradient: 0.0 min 90% A→1.2 min 5% A→2.0 min 5% A; oven: 50° C.; flow rate: 0.40 ml/min; UV detection: 208-400 nm.

Method 2 (LC-MS):

Instrument MS: Thermo Scientific FT-MS; Instrument type UHPLC+: Thermo Scientific UltiMate 3000; Column: Waters, HSST3, 2.1×75 mm, C18 1.8 µm; eluent A: 1 l water+0.01% formic acid; eluent B: 1 l acetonitrile+0.01% formic acid; gradient: 0.0 min 10% B→2.5 min 95% B→3.5 min 95% B; oven: 50° C.; flow rate: 0.90 ml/min; UV detection: 210 nm/optimum integration path 210-300 nm.

Method 3 (LC-MS):

Instrument: Agilent MS Quad 6150; HPLC: Agilent 1290; Column: Waters Acquity UPLC HSS T3 1.8µ 50×2.1 mm; eluent A: 1 l water+0.25 ml 99% formic acid, eluent B: 1 l acetonitrile+0.25 ml99% formic acid; gradient: 0.0 min 90% A→0.3 min 90% A→1.7 min 5% A→3.0 min 5% A; oven: 50° C.; flow: 1.20 ml/min; UV-detection: 205-305 nm.

Method 4 (Preparative HPLC):

Column: Chromatorex or Reprosil C18 10 µm, 125×30 mm; eluent A: water+0.1% formic acid, eluent B: acetonitrile+0.1% formic acid; gradient: 3 min 10% B, 17.5 min 95% B, 19.5 min 100% B, 20 min 10% B; flow: 75 ml/min; run time: 20 min; detection at 210 nm.

Method 5 (LC-MS):

Instrument: Waters Single Quad MS System; Instrument Waters UPLC Acquity; Column: Waters BEH C18 1.7 µm 50×2.1 mm; eluent A: 1 l water+1.0 ml (aqueous ammonia solution, 25%)/1, eluent B: 1 l acetonitrile; gradient: 0.0 min 92% A→0.1 min 92% A→1.8 min 5% A→3.5 min 5% A; oven: 50° C.; flow: 0.45 ml/min; UV-detection: 210 nm (208-400 nm).

Microwave

The microwave reactor used was an Initiator⁺ microwave system with robot sixty from Biotage®.

X-Ray Diffractometry

Transmission diffractometer PANalytical X`Pert PRO with PIXcel counter (multichannel):

radiation: copper, K alpha
primary monochromator: focussing X-ray mirror
wavelength (K1): 1.5406 Å
wavelength (K2): 1.5444 Å
generator parameters: 40 kV, 40 mA
measuring range: 2-38°
room conditions: 25° C., 40-60% rh Thermogravimetry TGA 7 Thermogravimetric Analyzer; manufacturer: Perkin-Elmer; heating rate: 10 Kmin⁻¹; purge gas: nitrogen, 20-30 ml/min; crucible: open Aluminium crucible; sample preparation: none.

Infrared Spectra

Bruker Tensor 37 spectrometer; spectral resolution 2 cm⁻¹; number of individual measurements 64; wave number range 4000-550 cm⁻¹; sample preparation: none.

Experimental Section—Starting Materials and Intermediates

Example 1A

{3-(4-Chlorophenyl)-5-oxo-4-[(2S)-3,3,3-trifluoro-2-hydroxypropyl]-4,5-dihydro-1H-1,2,4-triazol-1-yl}acetonitrile

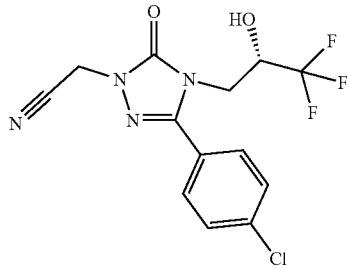 [SMILES: N#CCn1nc(-c2ccc(Cl)cc2)n(C[C@H](O)C(F)(F)F)c1=O]

In a 2 l reaction vessel, 100 g (273 mmol) of {3-(4-chlorophenyl)-5-oxo-4-[(2S)-3,3,3-trifluoro-2-hydroxypropyl]-4,5-dihydro-1H-1,2,4-triazol-1-yl}acetic acid (synthesis described as Example 8A in WO 2010/105770-A1), 43.3 g (547 mmol) of pyridine and 33 mg (0.3 mmol) of 4-dimethylaminopyridine were dissolved in 300 ml THF. The resulting solution was treated at 5° C. with 52.8 g (438 mmol) of 2,2-dimethylpropanoylchloride over 15 minutes and the resulting mixture was stirred at room temperature for 2.5 hours. After cooling to 0° C., 183 ml of 28% aqueous ammonia solution was added over 1 h while the solution temperature was kept between 10° C. and 20° C. and at the resulting mixture then stirred at 5° C. for an additional time period of 1 h. 500 ml methyl tert-butylether and 300 ml 20% aqueous citric acid were then added while keeping the internal temperature between 10° C. and 20° C. The phases were the separated and the organic phase was washed with 300 ml of 20% aqueous citric acid followed by 300 ml saturated aqueous sodium hydrogencarbonate solution and finally with 300 ml of 10% aqueous sodium chloride solution. The organic phase was evaporated at 60° C. under reduced pressure until an oily residue was obtained. 300 ml THF was then added and the solution was evaporated again until an oily solution was obtained. This operation was repeated a second time. The oil residue was retaken in 360 ml THF and treated with 172 g (820 mmol) trifluoroacetic acid anhydride over 20 min at a temperature between 10° C. and 20° C. The resulting solution was then stirred at room temperature for 1 h. 720 ml 4-methyl-2-pentanone and 650 ml 7.5% aqueous sodium hydroxide solution were added at a temperature between 10° C. and 20° C. Finally the pH-value was adjusted to pH=9.5 using 7.5% aqueous sodium hydroxide solution. After phase separation, the organic phase was washed twice with 450 ml 10% aqueous sodium chloride solution. The organic phase was evaporated at a temperature of 80° C. under reduced pressure while 1200 ml n-heptane was added. The formed suspension was cooled to 20° C. and a solid formed which was filtered off and washed with 200 ml n-heptane and then dried under reduced pressure (50° C., 30 mbar) affording 88 g (93% of th.) of {3-(4-chlorophenyl)-5-oxo-4-[(2S)-3,3,3-trifluoro-2-hydroxypropyl]-4,5-dihydro-1H-1,2,4-triazol-1-yl}acetonitrile as a solid.

1H-NMR (400 MHz, DMSO-d6): δ [ppm]=7.78 (d, 2H), 7.55 (d, 2H), 6.91 (d, 1H), 5.17 (s, 2H), 4.34-4.23 (m, 1H), 3.98 (dd, 1H), 3.81 (dd, 1H).

Example 2A

Methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate

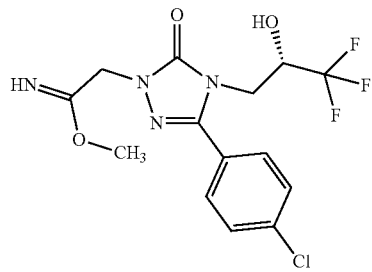 [SMILES: COC(=N)Cn1nc(-c2ccc(Cl)cc2)n(C[C@H](O)C(F)(F)F)c1=O]

In a 4 l reaction vessel, 200 g (576.9 mmol) of {3-(4-chlorophenyl)-5-oxo-4-[(2S)-3,3,3-trifluoro-2-hydroxypropyl]-4,5-dihydro-1H-1,2,4-triazol-1-yl}acetonitrile (Example 1A) in 1600 ml methanol was treated with 5.2 g (28 mmol) sodium methanolate (30% in methanol) and the resulting mixture was stirred at 50° C. for 2.5 hours. The solution was then evaporated at 50° C. under reduced pressure until an oily solution was obtained. 2000 ml methyl tert-butylether was added and the solution was concentrated until a volume of 800 ml was achieved. 3000 ml n-heptane was then added and a suspension was formed. After cooling at 20° C., the solid was filtered and washed with 500 ml n-heptane and then dried under reduced pressure (50° C., 30 mbar) affording 175 g (80% of th.) of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate as a solid.

1H-NMR (400 MHz, DMSO-d6): δ [ppm]=8.01 (s, 1H), 7.78 (d, 2H), 7.62 (d, 2H), 6.93 (br. s, 1H), 4.50 (s, 2H), 4.35-4.23 (m, 1H), 3.96 (dd, 1H), 3.81 (dd, 1H), 3.67 (s, 3H)..

Example 3A

Methyl 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[3-(trifluoromethyl)pyridin-2-yl]-1H-1,2,4-triazole-5-carboxylate

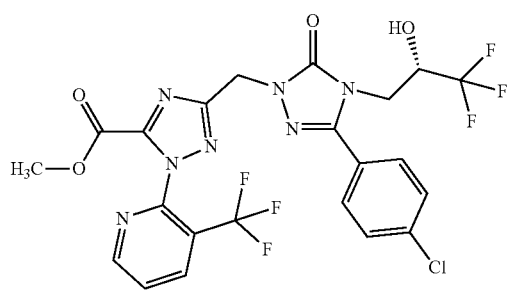 [SMILES: COC(=O)c1nc(Cn2nc(-c3ccc(Cl)cc3)n(C[C@H](O)C(F)(F)F)c2=O)nn1-c1ncccc1C(F)(F)F]

A solution of 1.0 g of methyl 2-{3-(4-chlorophenyl)-5-oxo-4-[(2S)-3,3,3-trifluoro-2-hydroxypropyl]-4,5-dihydro-1H-1,2,4-triazol-1-yl}ethanimidate (Example 2A, 2.64 mmol) in 20 ml 1,4-dioxane was cooled to 10° C. and then treated with 388 mg (3.17 mmol) methyl chlorooxoacetate and 0.55 ml (3.18 mmol) N,N-diisopropylethylamine. The resulting mixture was then stirred for 30 min. A prestirred solution of 1.10 g (3.17 mmol) 2-hydrazino-3-(trifluoromethyl)pyridine 4-methylbenzenesulfonate salt (1:1), 0.65 ml (3.72 mmol) N,N-diisopropylethylamine and 506 mg (3.19 mmol) anhydrous copper(II) sulfate in 10 ml 1,4-dioxane were added to the reaction mixture and the resulting mixture was then stirred overnight at room temperature. Water was then added and the aqueous phase was extracted with ethyl acetate, the combined organic phases were washed with aqueous sodium chloride solution, dried over magnesium sulfate and evaporated in vacuo affording 777 mg (50% of th.) of the title compound as a solid.

LC-MS (Method 1): $R_t$=1.00 min; MS (ESIpos): m/z=592.6 [M+H]⁻

¹H-NMR (400 MHz, DMSO-d6): δ [ppm]=8.93 (d, 1H), 8.60 (dd, 1H), 7.98 (dd, 1H), 7.75 (d, 2H), 7.67-7.57 (m, 2H), 6.91 (d, 1H), 5.22 (s, 2H), 4.37-4.22 (m, 1H), 4.10-3.97 (m, 1H), 3.85 (dd, 1H), 3.77 (s, 3H).

Example 4A 3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-[3-(trifluoromethyl)pyridin-2-yl]-1H-1,2,4-triazole-5-carboxamide

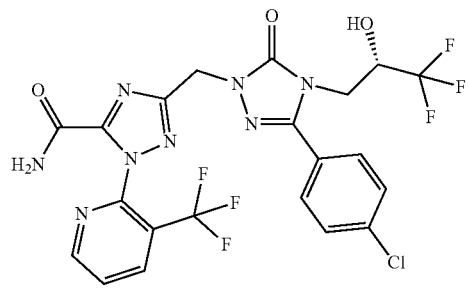 [SMILES: NC(=O)c1nc(Cn2nc(-c3ccc(Cl)cc3)n(C[C@H](O)C(F)(F)F)c2=O)nn1-c1ncccc1C(F)(F)F]

1.80 g Methyl 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[3-(trifluoromethyl)pyridin-2-yl]-1H-1,2,4-triazole-5-carboxylate (Example 3A, 3.04 mmol) was dissolved in 10.0 ml of an ammonia solution (7N in methanol, 70.0 mmol). The resulting mixture was stirred for 1 h at room temperature. The solvent was removed in vacuo and the crude product was purified by preparative HPLC (Method 4). Lyophilisation of the product containing fractions afforded 1.49 g (85% of th.) of the title compound as a solid.

LC-MS (Method 3): $R_t$=1.20 min; MS (ESIpos): m/z=577 [M+H]⁺

¹H-NMR (400 MHz, DMSO-d6): δ [ppm]=8.87 (d, 1H), 8.51 (d, 1H), 8.39 (s, 1H), 7.99 (s, 1H), 7.90 (dd, 1H), 7.82-7.68 (m, 2H), 7.63 (d, 2H), 6.90 (s, 1H), 5.22-5.07 (m, 2H), 4.29 (br s, 1H), 4.16-3.94 (m, 1H), 3.85 (dd, 1H).

Example 5A

Methyl 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[2-(trifluoromethyl)phenyl]-1H-1,2,4-triazole-5-carboxylate

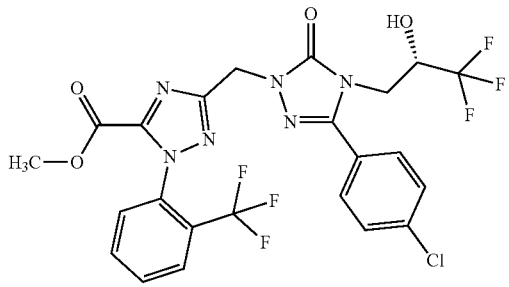 [SMILES: COC(=O)c1nc(Cn2nc(-c3ccc(Cl)cc3)n(C[C@H](O)C(F)(F)F)c2=O)nn1-c1ccccc1C(F)(F)F]

Under argon, a solution of 150 mg (0.40 mmol) of methyl-2-{3-(4-chlorophenyl)-5-oxo-4-[(2S)-3,3,3-trifluoro-2-hydroxypropyl]-4,5-dihydro-1H-1,2,4-triazol-1-yl}ethanimidate (Example 2A) in 3 ml anhydrous THF was treated at 0° C. with 75 µl (0.44 mmol) N,N-diisopropylethylamine and 40 µl (0.44 mmol) methyl chlorooxoacetate and the mixture was then stirred at 0° C. for 30 min. 93 mg (0.44 mmol) of [2-(trifluoromethyl)phenyl]hydrazine were then added, followed by 145 µl (0.83 mmol) of N,N-diisopropylethylamine. The resulting mixture was stirred for 2 h at room temperature, followed by 1 h at 120° C. in the microwave and then evaporated. The obtained residue was purified by preparative HPLC (Method 4) affording 75 mg (32% of th.) of the title compound.

LC-MS (Method 2): $R_t$=2.01 min; MS (ESIpos): m/z=591.1 [M+H]$^+$ $^1$H-NMR (400 MHz, DMSO-d6): δ [ppm]=8.07-7.56 (m, 8H), 6.91 (d, 1H), 5.17 (d, 2H), 4.37-4.21 (m, 1H), 4.09-3.80 (m, 2H), 3.74 (s, 3H).

Example 6A 3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-[2-(trifluoromethyl)phenyl]-1H-1,2,4-triazole-5-carboxamide

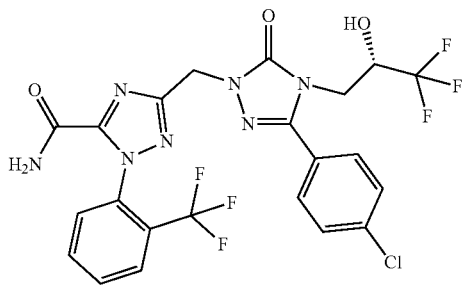 [SMILES: NC(=O)c1nc(Cn2nc(-c3ccc(Cl)cc3)n(C[C@H](O)C(F)(F)F)c2=O)nn1-c1ccccc1C(F)(F)F]

A mixture of 55 mg (0.093 mmol) of methyl 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[2-(trifluoromethyl)phenyl]-1H-1,2,4-triazole-5-carboxylate (Example 5A) in an ammonia solution (7N in methanol, 0.8 ml, 5.6 mmol) was stirred overnight at room temperature and the mixture was then evaporated. The obtained residue was purified by preparative HPLC (Method 4) affording 55 mg (quant.) of the title compound.

LC-MS (Method 2): $R_t$=1.77 min; MS (ESIpos): m/z=576.1 [M+H]$^+$ $^1$H NMR (400 MHz, DMSO-d6): δ [ppm]=8.23 (s, 1H), 8.00-7.55 (m, 9H), 6.90 (d, 1H), 5.22-5.01 (m, 2H), 4.40-4.18 (m, 1H), 4.10-3.76 (m, 2H).

Example 7A

Methyl 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-(3-chloropyridin-2-yl)-1H-1,2,4-triazole-5-carboxylate

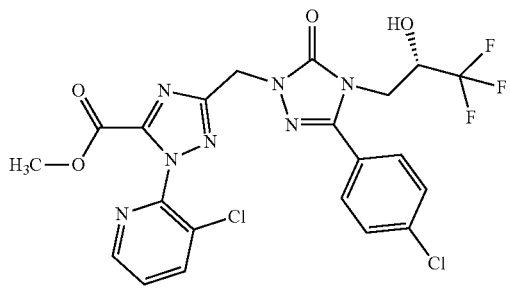 [SMILES: COC(=O)c1nc(Cn2nc(-c3ccc(Cl)cc3)n(C[C@H](O)C(F)(F)F)c2=O)nn1-c1ncccc1Cl]

A solution of 150 mg of methyl-2-{3-(4-chlorophenyl)-5-oxo-4-[(2S)-3,3,3-trifluoro-2-hydroxypropyl]-4,5-dihydro-1H-1,2,4-triazol-1-yl}ethanimidate (Example 2A, 26.4 mmol) in 3 ml THF was cooled to 0° C. and then treated with 58.2 mg (0.48 mmol) methyl chlorooxoacetate and 275 µl (1.58 mmol) N,N-diisopropylethylamine. The resulting mixture was warmed up to room temperature and stirred for 1 h and cooled again to 0° C. 62.6 mg (0.436 mmol) 3-chloro-2-hydrazinopyridine were then added and the reaction mixture was warmed up to room temperature and then stirred for 1 h, followed by 1 h at 120° C. in a sealed vial under microwave irradiation. The crude product was purified by preparative HPLC (Method 4). Lyophilisation of the product containing fractions afforded 25.3 mg (11% of th.) of the title compound.

LC-MS (Method 2): $R_t$=1.82 min; MS (ESIpos): m/z=558.1[M+H]$^+$ $^1$H-NMR (400 MHz, DMSO-d6): δ [ppm]=8.70-8.24 (m, 2H), 7.89-7.56 (m, 5H), 6.92 (d, 1H), 5.22 (s, 2H), 4.46-4.20 (m, 1H), 3.79 (s, 5H).

Example 8A 3-({3-(4-Chlorophenyl)-5-oxo-4-[(2S)-3,3,3-trifluoro-2-hydroxypropyl]-4,5-dihydro-1H-1,2,4-triazol-1-yl}methyl)-1-(3-chloropyridin-2-yl)-1H-1,2,4-triazole-5-carboxamide

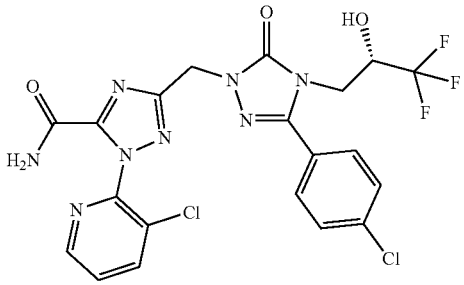 [SMILES: NC(=O)c1nc(Cn2nc(-c3ccc(Cl)cc3)n(C[C@H](O)C(F)(F)F)c2=O)nn1-c1ncccc1Cl]

5.1 g Methyl 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-(3-chloropyridin-2-yl)-1H-1,2,4-triazole-5-carboxylate (Example 7A, 9.134 mmol) was dissolved in 42.5 ml of an ammonia solution (7N in methanol, 297 mmol). The resulting mixture was stirred for 2 h at room temperature. The solution was then poured on ice and the mixture stirred for 10 min. The precipitate was filtered off and washed with water, which afforded 3.5 g of crude product. The aqueous phase was extracted with ethyl acetate. The organic phase was dried over magnesium sulfate, filtered and the solvent was removed in vacuo. The crude product was purified by flash chromatography (silica gel, dichloromethane/methanol, 97/3), affording 4.00 g (81% of th.) of the title compound as a solid.

LC-MS (Method 2): $R_t$=1.62 min; MS (ESIpos): m/z=543.1 [M+H]$^+$ $^1$H-NMR (400 MHz, DMSO-d6): δ [ppm]=8.55 (dd, 1H), 8.39 (s, 1H), 8.25 (dd, 1H), 8.00 (s, 1H), 7.76 (d, 2H), 7.69 (dd, 1H), 7.62 (d, 2H), 6.90 (d, 1H), 5.18 (d, 2H), 4.36-4.23 (m, 1H), 4.06-3.97 (m, 1H), 3.85 (dd, 1H).

Experimental Section—Examples

Example 1

(2S)-3-[1-({5-Carbamoyl-1-[3-(trifluoromethyl)pyridin-2-yl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl Dihydrogen Phosphate

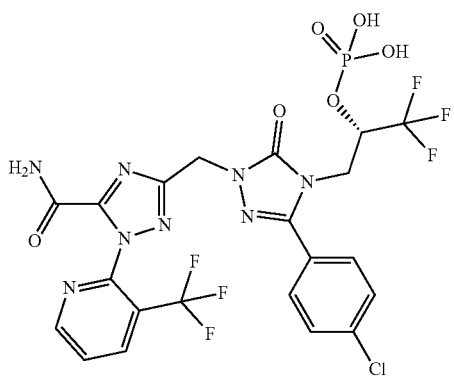 [SMILES: NC(=O)c1nc(Cn2nc(-c3ccc(Cl)cc3)n(C[C@H](OP(=O)(O)O)C(F)(F)F)c2=O)nn1-c1ncccc1C(F)(F)F]

At 0° C., a solution of 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[3-(trifluoromethyl)pyridin-2-yl]-1H-1,2,4-triazole-5-carboxamide (Example 4A, 2.00 g, 3.47 mmol) in tetrahydrofuran (40 ml, 490 mmol) was treated with 4-N,N-dimethylaminopyridine (635 mg, 5.20 mmol) and triethylamine (720 µl, 5.2 mmol). Phosphorus oxychloride (480 µl, 5.2 mmol) was then added dropwise. The resulting mixture was stirred for 40 min at 0° C. and then for 50 min at room temperature. Thereafter water (4.0 ml) and a saturated aqueous sodium hydrogen carbonate solution (24 ml) were added and the resulting mixture was stirred overnight at room temperature. Tetrahydrofuran was then evaporated at room temperature. The resulting solution was diluted with water and extracted with ethyl acetate. The aqueous phase was brought to pH=1 with a hydrochloric acid solution (1N), diluted with a saturated aqueous sodium chloride solution and extracted with ethyl acetate. The combined organic layers were washed with a saturated aqueous sodium chloride solution, dried over magnesium sulfate and evaporated. The residue was purified by preparative HPLC (Method 4) affording 1.32 g (58% of th.) of the title compound.

LC-MS (Method 3): $R_t$=0.94 min; MS (ESIpos): m/z=657.0 [M+H]$^+$ $^1$H-NMR (400 MHz, DMSO-d6): δ [ppm]=8.86 (d, 1H), 8.58-8.29 (m, 2H), 8.07-7.82 (m, 2H), 7.79-7.45 (m, 4H), 5.33-5.00 (m, 2H), 4.95-4.77 (br m, 1H), 4.29-3.89 (m, 2H), 3.36 (br s, 2H, overlapping with HDO peak).

Example 1-1

(2S)-3-[1-({5-Carbamoyl-1-[3-(trifluoromethyl)pyridin-2-yl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl Dihydrogen Phosphate Hemihydrate

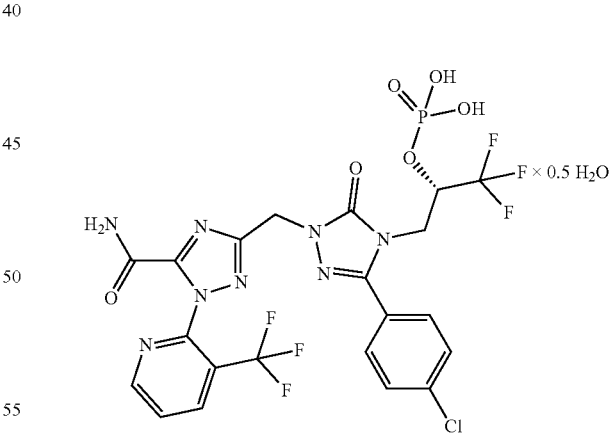

A suspension of (2S)-3-[1-({5-carbamoyl-1-[3-(trifluoromethyl)pyridin-2-yl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate (4.46 g, 6.79 mmol) in 446 ml toluene was stirred at 25° C. for seven days. The solid was filtered off and the filtrate evaporated. The solid and the residue obtained from the filtrate were mixed together and suspended in a mixture of dichloromethane/n-heptane (200 ml, 55:45). The resulting mixture was stirred at 40° C. for eight days. The solid material was filtered off and examined by X-Ray diffractometry and corresponds to the title compound as crystalline material (hemihydrate form).

TABLE 2

X-ray powder diffractometry of the compound obtained as crystalline material in example 1-1
Reflexes [2θ]
(peak maxima)

| | |
|---|---|
| 6.2 | 20.4 |
| 7.5 | 20.6 |
| 11.0 | 21.3 |
| 12.8 | 21.6 |
| 13.0 | 22.4 |
| 13.3 | 23.3 |
| 14.6 | 23.5 |
| 14.7 | 23.8 |
| 14.8 | 23.9 |
| 16.0 | 24.2 |
| 16.3 | 24.6 |
| 16.5 | 25.1 |
| 16.9 | 25.8 |
| 17.3 | 30.2 |
| 19.5 | |

TABLE 3

Infrared spectrum of the compound obtained as crystalline material in example 1-1
Bands
[peak maxima in cm$^{-1}$]

| | |
|---|---|
| 569* | 1100 |
| 619 | 1131 |
| 642 | 1137 |
| 656 | 1163* |
| 678 | 1175 |
| 703 | 1191* |
| 710 | 1237* |
| 723 | 1273 |
| 727 | 1321 |
| 746 | 1334 |
| 762* | 1354 |
| 781 | 1374 |
| 810 | 1398* |
| 823 | 1405 |
| 853* | 1423 |
| 860* | 1450 |
| 888 | 1495 |
| 944 | 1582 |
| 976 | 1605 |
| 1014 | 1699 |
| 1031 | 3188 |
| 1036 | 3253* |
| 1045 | 3305* |
| 1091 | 3392 |

The bands marked with * are specific to the free acid.

Example 2

Potassium (2S)-3-[1-({5-carbamoyl-1-[3-(trifluoromethyl)pyridin-2-yl]-1H-1,2,4-triazol-3-yl}-methyl)-3-(4-chlorophenyl)-5-oxo-1,5-dihydro-4H-1,2,4-triazol-4-yl]-1,1,1-trifluoropropan-2-yl Hydrogen Phosphate

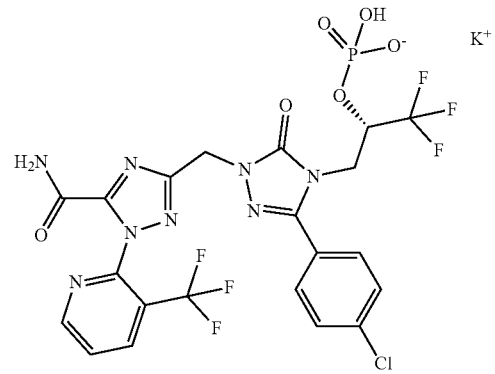 [SMILES: NC(=O)c1nc(Cn2nc(-c3ccc(Cl)cc3)n(C[C@H](OP(=O)([O-])O)C(F)(F)F)c2=O)nn1-c1ncccc1C(F)(F)F ; [K+]]

A solution of (2S)-3-[1-({5-carbamoyl-1-[3-(trifluoromethyl)pyridin-2-yl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate (Example 1, 104 mg, 158 µmol) in water (3.0 ml) was treated with potassium hydrogen carbonate (31.6 mg, 316 µmol), then stirred for 15 min at room temperature and lyophilized affording 124 mg (quant.) of the title compound.

LC-MS (Method 1): $R_t$=0.67 min; MS (ESIpos): m/z=657.0 [M+H]$^+$ $^1$H-NMR (500 MHz, D$_2$O): δ [ppm]=8.87-8.80 (m, 1H), 8.52 (d, 1H), 7.95 (dd, 1H), 7.72-7.57 (m, 4H), 5.45-5.36 (m, 1H), 5.35-5.26 (m, 1H), 4.99-4.55 (m, 1H, overlap with HDO peak), 4.20-4.07 (m, 2H).

Example 3

Potassium (2S)-3-[1-({5-carbamoyl-1-[3-(trifluoromethyl)pyridin-2-yl]-1H-1,2,4-triazol-3-yl}-methyl)-3-(4-chlorophenyl)-5-oxo-1,5-dihydro-4H-1,2,4-triazol-4-yl]-1,1,1-trifluoropropan-2-yl Hydrogen Phosphate

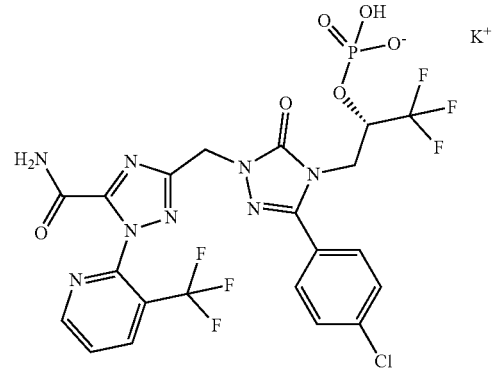 [SMILES: NC(=O)c1nc(Cn2nc(-c3ccc(Cl)cc3)n(C[C@H](OP(=O)([O-])O)C(F)(F)F)c2=O)nn1-c1ncccc1C(F)(F)F ; [K+]]

A solution of (2S)-3-[1-({5-carbamoyl-1-[3-(trifluoromethyl)pyridin-2-yl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate (Example 1, 35.0 mg, 53.3 μmol) in water (1.0 ml) was treated with potassium hydrogen carbonate (5.33 mg, 53.3 μmol), then stirred for 15 min at room temperature and lyophilized affording 39.5 mg (quant.) of the title compound.

LC-MS (Method 1): $R_t$=0.67 min; MS (ESIpos): m/z=657.0 [M+H]$^+$ $^1$H-NMR (500 MHz, D$_2$O): δ [ppm]=8.87-8.80 (m, 1H), 8.54-8.48 (m, 1H), 7.97-7.91 (m, 1H), 7.71-7.57 (m, 4H), 5.43-5.37 (m, 1H), 5.35-5.28 (m, 1H), 4.90-4.64 (m, 1H, overlap with HDO peak), 4.23-4.10 (m, 2H).

Example 4

Sodium (2S)-3-[1-({5-carbamoyl-1-[3-(trifluoromethyl)pyridin-2-yl]-1H-1,2,4-triazol-3-yl}-methyl)-3-(4-chlorophenyl)-5-oxo-1,5-dihydro-4H-1,2,4-triazol-4-yl]-1,1,1-trifluoropropan-2-yl Hydrogen Phosphate

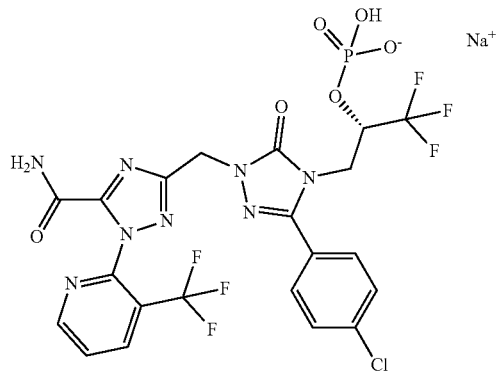 [SMILES: NC(=O)c1nc(Cn2nc(-c3ccc(Cl)cc3)n(C[C@H](OP(=O)([O-])O)C(F)(F)F)c2=O)nn1-c1ncccc1C(F)(F)F ; [Na+]]

A solution of (2S)-3-[1-({5-carbamoyl-1-[3-(trifluoromethyl)pyridin-2-yl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate (Example 1, 35.0 mg, 53.3 μmol) in water (1.0 ml) was treated with disodium carbonate (5.65 mg, 53.3 μmol), then stirred for 15 min at room temperature and lyophilized affording 41.2 mg (quant.) of the title compound.

LC-MS (Method 1): $R_t$=0.68 min; MS (ESIpos): m/z=657.0 [M+H]$^+$ $^1$H-NMR (500 MHz, D$_2$O): δ [ppm]=8.86-8.82 (m, 1H), 8.54-8.49 (m, 1H), 7.98-7.92 (m, 1H), 7.72-7.58 (m, 4H), 5.43-5.37 (m, 1H), 5.34-5.28 (m, 1H), 4.88-4.65 (m, 1H, overlap with HDO peak), 4.20-4.06 (m 2H).

Example 5

Sodium (2S)-3-[1-({5-carbamoyl-1-[3-(trifluoromethyl)pyridin-2-yl]-1H-1,2,4-triazol-3-yl}-methyl)-3-(4-chlorophenyl)-5-oxo-1,5-dihydro-4H-1,2,4-triazol-4-yl]-1,1,1-trifluoropropan-2-yl Hydrogen Phosphate

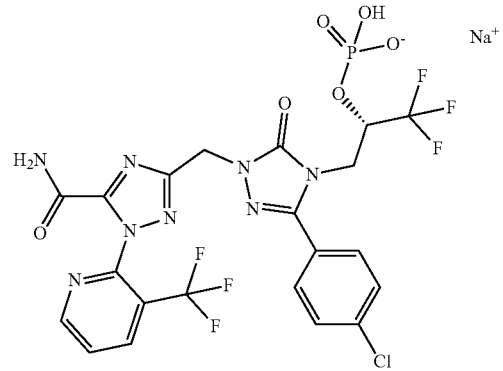 [SMILES: NC(=O)c1nc(Cn2nc(-c3ccc(Cl)cc3)n(C[C@H](OP(=O)([O-])O)C(F)(F)F)c2=O)nn1-c1ncccc1C(F)(F)F ; [Na+]]

A solution of (2S)-3-[1-({5-carbamoyl-1-[3-(trifluoromethyl)pyridin-2-yl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate (Example 1, 35.0 mg, 53.3 μmol) in water (1.0 ml) was treated with sodium hydrogen carbonate (4.48 mg, 53.3 μmol), then stirred for 15 min at room temperature and lyophilized affording 38.6 mg (quant.) of the title compound.

LC-MS (Method 1): $R_t$=0.68 min; MS (ESIpos): m/z=657 [M+H]$^+$ $^1$H-NMR (500 MHz, D$_2$O): δ [ppm]=8.86-8.81 (m, 1H), 8.53-8.48 (m, 1H), 7.97-7.92 (m, 1H), 7.71-7.58 (m, 4H), 5.42-5.36 (m, 1H), 5.34-5.27 (m, 1H), 4.68 (s, 1H, overlap with HDO peak), 4.22-4.10 (m, 2H).

Example 6

Lithium (2S)-3-[1-({5-carbamoyl-1-[3-(trifluoromethyl)pyridin-2-yl]-1H-1,2,4-triazol-3-yl}-methyl)-3-(4-chlorophenyl)-5-oxo-1,5-dihydro-4H-1,2,4-triazol-4-yl]-1,1,1-trifluoropropan-2-yl Hydrogen Phosphate

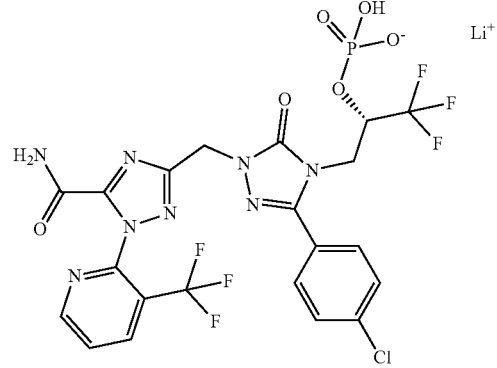 [SMILES: NC(=O)c1nc(Cn2nc(-c3ccc(Cl)cc3)n(C[C@H](OP(=O)([O-])O)C(F)(F)F)c2=O)nn1-c1ncccc1C(F)(F)F ; [Li+]]

A solution of (2S)-3-[1-({5-carbamoyl-1-[3-(trifluoromethyl)pyridin-2-yl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate (Example 1, 35.0 mg, 53.3 μmol) in water (1.0 ml) was treated with lithium hydroxide hydrate (1:1) (4.47 mg, 107 μmol), then stirred for 15 min at room temperature and lyophilized affording 38.7 mg (quant) of the title compound.

LC-MS (Method 1): $R_t$=0.67 min; MS (ESIpos): m/z=657.0 [M+H]$^+$ $^1$H-NMR (500 MHz, D$_2$O): δ [ppm]=8.86-8.82 (m, 1H), 8.54-8.49 (m, 1H), 7.98-7.91 (m, 1H), 7.72-7.58 (m, 4H), 5.43-5.37 (m, 1H), 5.34-5.28 (m, 1H), 4.90-4.68 (m, 1H, overlap with HDO peak), 4.21-4.06 (m, 2H).

Example 7

Lithium (2S)-3-[1-({5-carbamoyl-1-[3-(trifluoromethyl)pyridin-2-yl]-1H-1,2,4-triazol-3-yl}-methyl)-3-(4-chlorophenyl)-5-oxo-1,5-dihydro-4H-1,2,4-triazol-4-yl]-1,1,1-trifluoropropan-2-yl Hydrogen Phosphate

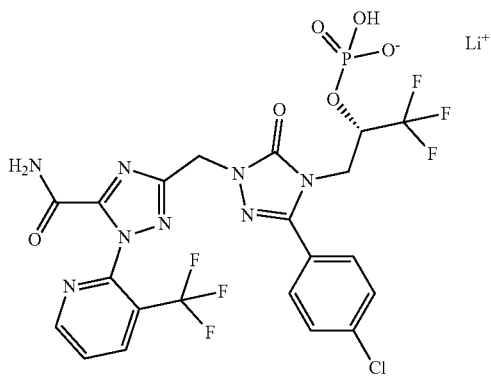 [SMILES: NC(=O)c1nc(Cn2nc(-c3ccc(Cl)cc3)n(C[C@H](OP(=O)([O-])O)C(F)(F)F)c2=O)nn1-c1ncccc1C(F)(F)F ; [Li+]]

A solution of (2S)-3-[1-({5-carbamoyl-1-[3-(trifluoromethyl)pyridin-2-yl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate (Example 1, 35.0 mg, 53.3 μmol) in water (1.0 ml) was treated with lithium hydroxide hydrate (1:1) (2.24 mg, 53.3 μmol), then stirred for 15 min at room temperature and lyophilized affording 38.3 mg (quant.) of the title compound.

LC-MS (Method 1): $R_t$=0.67 min; MS (ESIpos): m/z=657.0 [M+H]$^+$ $^1$H-NMR (500 MHz, D$_2$): δ [ppm]=8.83 (d, 1H), 8.51 (d, 1H), 7.94 (dd, 1H), 7.71-7.58 (m, 4H), 5.42-5.37 (m, 1H), 5.34-5.28 (m, 1H), 4.89-4.65 (m, 1H, overlap with HDO peak), 4.22-4.10 (m, 2H).

Example 8

Calcium (2S)-3-[1-({5-carbamoyl-1-[3-(trifluoromethyl)pyridin-2-yl]-1H-1,2,4-triazol-3-yl}-methyl)-3-(4-chlorophenyl)-5-oxo-1,5-dihydro-4H-1,2,4-triazol-4-yl]-1,1,1-trifluoropropan-2-yl Phosphate

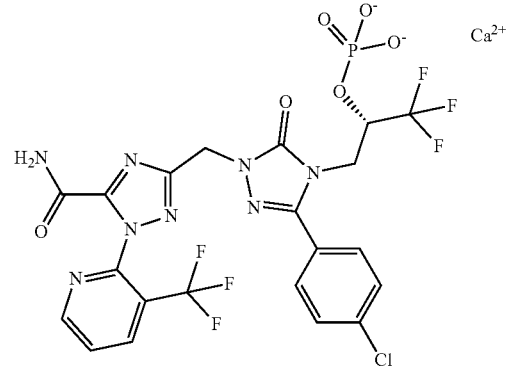 [SMILES: NC(=O)c1nc(Cn2nc(-c3ccc(Cl)cc3)n(C[C@H](OP(=O)([O-])[O-])C(F)(F)F)c2=O)nn1-c1ncccc1C(F)(F)F ; [Mg+2]]

A solution of (2S)-3-[1-({5-carbamoyl-1-[3-(trifluoromethyl)pyridin-2-yl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate (Example 1, 100 mg, 152 μmol) in water (1 l) was treated with calcium carbonate (15.2 mg, 152 μmol), then stirred for 15 min at room temperature and lyophilized affording 93.9 mg (quant.) of the title compound.

LC-MS (Method 1): $R_t$=0.69 min; MS (ESIpos): m/z=657.1 [M+H]$^+$ $^1$H-NMR (500 MHz, D$_2$O): δ [ppm]=8.86-8.82 (m, 1H), 8.54-8.49 (m, 1H), 7.98-7.92 (m, 1H), 7.72-7.57 (m, 4H), 5.45-5.37 (m, 1H), 5.35-5.28 (m, 1H), 4.91-4.66 (m, 1H, overlap with HDO peak), 4.21-4.09 (m, 2H).

Example 9

Magnesium (2S)-3-[1-({5-carbamoyl-1-[3-(trifluoromethyl)pyridin-2-yl]-1H-1,2,4-triazol-3-yl}-methyl)-3-(4-chlorophenyl)-5-oxo-1,5-dihydro-4H-1,2,4-triazol-4-yl]-1,1,1-trifluoropropan-2-yl Phosphate

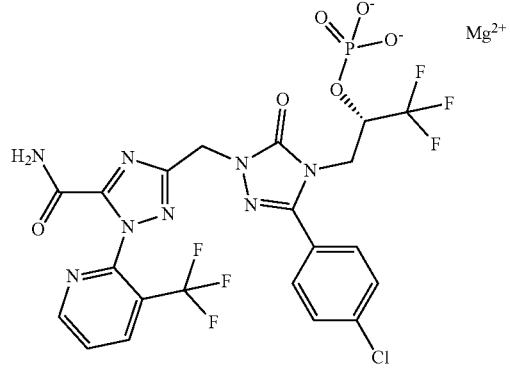

A solution of (2S)-3-[1-({5-carbamoyl-1-[3-(trifluoromethyl)pyridin-2-yl]-1H-1,2,4-triazol-3-yl}methyl)-3-(4- chlorophenyl)-5-oxo-1,5-dihydro-4H-1,2,4-triazol-4-yl]-1,1,1-trifluoropropan-2-yl dihydrogen phosphate (Example 1, 35.0 mg, 53.3 µmol) in water (1.0 ml) was treated with magnesium carbonate (4.49 mg, 53.3 µmol), then stirred for 15 min at room temperature and lyophilized affording 40.1 mg (quant.) of the title compound.

LC-MS (Method 1): $R_t$=0.68 min; MS (ESIpos): m/z=657.0 [M+H]$^+$ $^1$H-NMR (500 MHz, D$_2$O): δ [ppm]=8.87-8.81 (m, 1H), 8.54-8.48 (m, 1H), 7.98-7.91 (m, 1H), 7.73-7.58 (m, 4H), 5.43-5.37 (m, 1H), 5.35-5.27 (m, 1H), 4.92-4.60 (m, 1H, overlap with HDO peak), 4.20-4.06 (m, 2H).

Example 10

(2S)-3-[1-({5-Carbamoyl-1-[2-(trifluoromethyl)phenyl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl Dihydrogen Phosphate

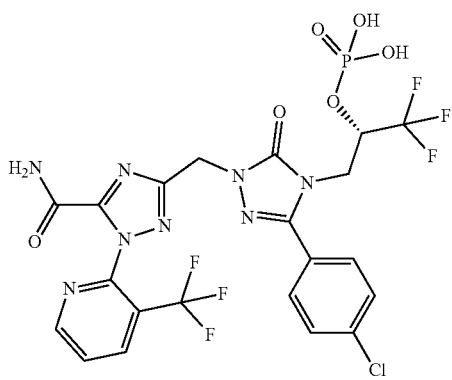 [SMILES: NC(=O)c1nc(Cn2nc(-c3ccc(Cl)cc3)n(C[C@H](OP(=O)(O)O)C(F)(F)F)c2=O)nn1-c1ncccc1C(F)(F)F]

At 0° C., a solution of 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-[2-(trifluoromethyl)phenyl]-1H-1,2,4-triazole-5-carboxamide (Example 6A, 1000 mg, 1.74 mmol) in tetrahydrofuran (20 ml, 250 mmol) was treated with 4-N,N-dimethylaminopyridine (318 mg, 2.60 mmol) and triethylamine (360 µl, 2.6 mmol). Phosphorus oxychloride (240 µl, 2.6 mmol) was added dropwise. The resulting mixture was stirred for 40 min at 0° C. and then for 50 min at room temperature. Thereafter water (2.0 ml) and a saturated aqueous sodium hydrogen carbonate solution (12 ml) were added and the resulting mixture was stirred overnight at room temperature. Tetrahydrofuran was then evaporated at room temperature. The resulting solution was diluted with water and extracted with ethyl acetate. The aqueous phase was brought to pH=1 with a hydrochloric acid solution (1N), diluted with a saturated aqueous sodium chloride solution and extracted with ethyl acetate. The combined organic layers were washed with a saturated sodium chloride solution, dried over magnesium sulfate and evaporated. The residue was purified by preparative HPLC (Method 4) affording 876 mg (77% of th.) of the title compound.

LC-MS (Method 1): $R_t$=0.74 min; MS (ESIpos): m/z=656.0 [M+H]$^+$ $^1$H-NMR (400 MHz, DMSO-d6): δ [ppm]=8.30 (br s, 1H), 7.96-7.50 (m, 8H), 5.25-4.96 (m, 2H), 4.97-4.74 (br m, 1H), 4.26-3.91 (m, 2H), 3.57 (br s, 2H, overlapping with HDO peak).

Example 11

Potassium (2S)-3-[1-({5-carbamoyl-1-[2-(trifluoromethyl)phenyl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl Hydrogen Phosphate

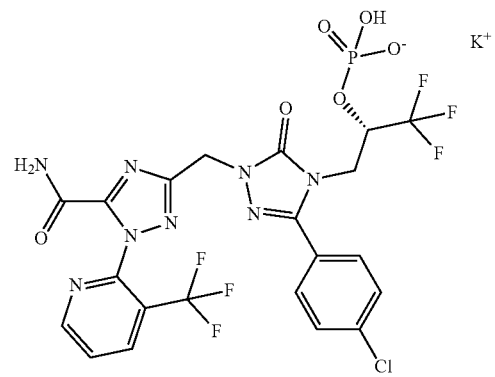 [SMILES: NC(=O)c1nc(Cn2nc(-c3ccc(Cl)cc3)n(C[C@H](OP(=O)([O-])O)C(F)(F)F)c2=O)nn1-c1ncccc1C(F)(F)F ; [K+]]

A solution of (2S)-3-[1-({5-carbamoyl-1-[2-(trifluoromethyl)phenyl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate (Example 10, 35.0 mg, 53.4 µmol) in water (1.0 ml) was treated with potassium hydrogen carbonate (10.7 mg, 107 µmol), then stirred for 15 min at room temperature and lyophilized affording 40.4 mg (quant.) of the title compound.

LC-MS (Method 1): $R_t$=0.73 min; MS (ESIpos): m/z=656.0 [M+H]$^+$ $^1$H-NMR (500 MHz, D$_2$O): δ [ppm]=7.97-7.93 (m, 1H), 7.87-7.79 (m, 2H), 7.73-7.59 (m, 5H), 5.38-5.33 (m, 1H), 5.30-5.24 (m, 1H), 4.88-4.66 (m, 1H, overlap with HDO peak), 4.20-4.06 (m, 2H).

Example 12

Potassium (2S)-3-[1-({5-carbamoyl-1-[2-(trifluoromethyl)phenyl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl Hydrogen Phosphate

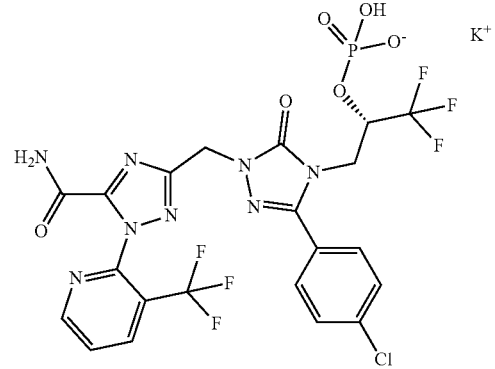 [SMILES: NC(=O)c1nc(Cn2nc(-c3ccc(Cl)cc3)n(C[C@H](OP(=O)([O-])O)C(F)(F)F)c2=O)nn1-c1ncccc1C(F)(F)F ; [K+]]

A solution of (2S)-3-[1-({5-carbamoyl-1-[2-(trifluoromethyl)phenyl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate (Example 10, 35.0 mg, 53.4 μmol) in water (1.0 ml) was treated with potassium hydrogen carbonate (5.34 mg, 53.4 μmol), then stirred for 15 min at room temperature and lyophilized affording 36.3 mg (quant.) of the title compound.

LC-MS (Method 1): $R_t$=0.73 min; MS (ESIpos): m/z=656.0 [M+H]$^+$ $^1$H-NMR (500 MHz, D$_2$O): δ [ppm]=7.97-7.93 (m, 1H), 7.88-7.79 (m, 2H), 7.71-7.58 (m, 5H), 5.39-5.24 (m, 2H), 4.90-4.67 (m, 1H, overlap with HDO peak), 4.19-4.09 (m, 2H).

Example 13

Sodium (2S)-3-[1-({5-carbamoyl-1-[2-(trifluoromethyl)phenyl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl Hydrogen Phosphate

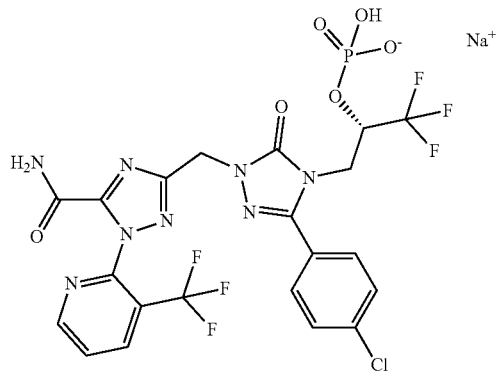 [SMILES: NC(=O)c1nc(Cn2nc(-c3ccc(Cl)cc3)n(C[C@H](OP(=O)([O-])O)C(F)(F)F)c2=O)nn1-c1ncccc1C(F)(F)F ; [Na+]]

A solution of (2S)-3-[1-({5-carbamoyl-1-[2-(trifluoromethyl)phenyl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate (Example 10, 35.0 mg, 53.4 μmol) in water (1.0 ml) was treated with disodium carbonate (5.66 mg, 53.4 μmol), then stirred for 15 min at room temperature and lyophilized affording 37.9 mg (quant.) of the title compound.

LC-MS (Method 1): $R_t$=0.74 min; MS (ESIpos): m/z=656.1 [M+H]$^+$ $^1$H-NMR (500 MHz, D$_2$O): δ [ppm]=7.97-7.93 (m, 1H), 7.89-7.78 (m, 2H), 7.74-7.57 (m, 5H), 5.40-5.22 (m, 2H), 4.92-4.64 (m, 1H, overlap with HDO peak), 4.22-4.04 (m, 2H).

Example 14

Sodium (2S)-3-[1-({5-carbamoyl-1-[2-(trifluoromethyl)phenyl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl Hydrogen Phosphate

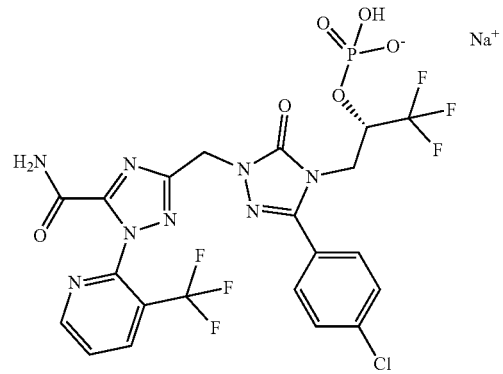 [SMILES: NC(=O)c1nc(Cn2nc(-c3ccc(Cl)cc3)n(C[C@H](OP(=O)([O-])O)C(F)(F)F)c2=O)nn1-c1ncccc1C(F)(F)F ; [Na+]]

A solution of (2S)-3-[1-({5-carbamoyl-1-[2-(trifluoromethyl)phenyl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate (Example 10, 35.0 mg, 53.4 μmol) in water (1.0 ml) was treated with sodium hydrogen carbonate (4.48 mg, 53.4 μmol), then stirred for 15 min at room temperature and lyophilized affording 36.2 mg (quant.) of the title compound.

LC-MS (Method 1): $R_t$=0.47 min; MS (ESIpos): m/z=656.0 [M+H]$^+$ $^1$H-NMR (500 MHz, D$_2$O): δ [ppm]=7.97-7.93 (m, 1H), 7.87-7.79 (m, 2H), 7.72-7.59 (m, 5H), 5.39-5.24 (m, 2H), 4.90-4.65 (m, 1H, overlap with HDO peak), 4.20-4.09 (m, 2H).

Example 15

Magnesium (2S)-3-[1-({5-carbamoyl-1-[2-(trifluoromethyl)phenyl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl Phosphate

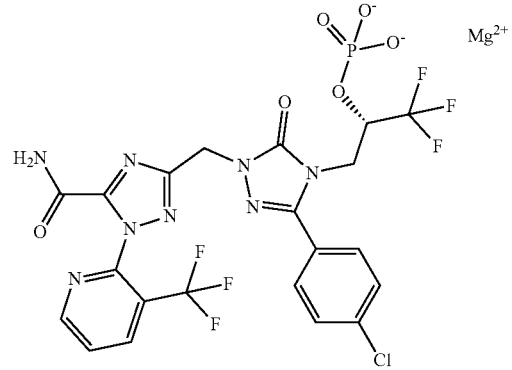 [SMILES: NC(=O)c1nc(Cn2nc(-c3ccc(Cl)cc3)n(C[C@H](OP(=O)([O-])[O-])C(F)(F)F)c2=O)nn1-c1ncccc1C(F)(F)F ; [Mg+2]]

A solution of (2S)-3-[1-({5-carbamoyl-1-[2-(trifluoromethyl)phenyl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate (Example 10, 35.0 mg, 53.4 μmol) in water (50 ml) was treated with magnesium carbonate (4.50 mg, 53.4 µmol), then stirred for 15 min at room temperature and lyophilized affording 37.3 mg (quant.) of the title compound.

LC-MS (Method 2): $R_t$=1.34 min; MS (ESIpos): m/z=656.1 [M+H]$^+$ $^1$H-NMR (500 MHz, D$_2$O): δ [ppm]=7.97-7.93 (m, 1H), 7.88-7.79 (m, 2H), 7.72-7.58 (m, 5H), 5.39-5.24 (m, 2H), 4.92-4.63 (m, 1H, overlap with HDO peak), 4.20-4.09 (m, 2H).

Example 16

Calcium (2S)-3-[1-({5-carbamoyl-1-[2-(trifluoromethyl)phenyl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl Phosphate

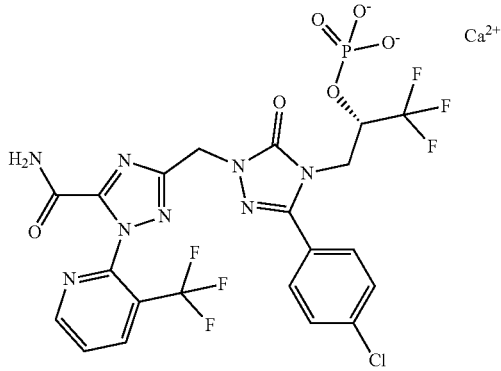 [SMILES: NC(=O)c1nc(Cn2nc(-c3ccc(Cl)cc3)n(C[C@H](OP(=O)([O-])[O-])C(F)(F)F)c2=O)nn1-c1ncccc1C(F)(F)F ; [Ca+2]]

A solution of (2S)-3-[1-({5-carbamoyl-1-[2-(trifluoromethyl)phenyl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate (Example 10, 35.0 mg, 53.4 µmol) in water (15 ml) was treated with calcium acetate monohydrate (9.40 mg, 53.4 µmol), then stirred for 15 min at room temperature and lyophilized affording 37.9 mg (quant.) of the title compound.

LC-MS (Method 2): $R_t$=1.33 min: MS (ESIpos): m/z=656.1 [M+H]$^+$ $^1$H-NMR (500 MHz, D$_2$O): δ [ppm]=8.00-7.91 (m, 1H), 7.89-7.77 (m, 2H), 7.73-7.55 (m, 5H), 5.42-5.22 (m, 2H), 4.99-4.50 (m, 1H, overlap with HDO peak), 4.27-3.99 (m, 2H).

Example 17

(2S)-3-[1-{[5-Carbamoyl-1-(3-chloropyridin-2-yl)-1H-1,2,4-triazol-3-yl]methyl}-3-(4-chloro-phenyl)-5-oxo-1,5-dihydro-4H-1,2,4-triazol-4-yl]-1,1,1-trifluoropropan-2-yl Dihydrogen Phosphate

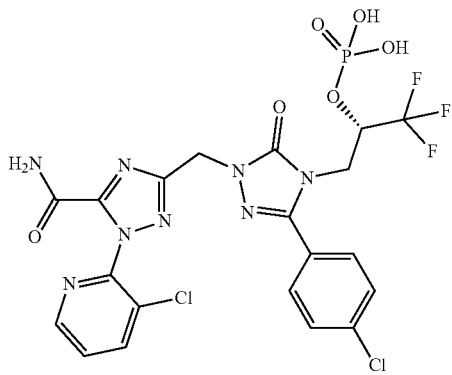 [SMILES: NC(=O)c1nc(Cn2nc(-c3ccc(Cl)cc3)n(C[C@H](OP(=O)(O)O)C(F)(F)F)c2=O)nn1-c1ncccc1Cl]

At 0° C., a solution of 3-({3-(4-chlorophenyl)-5-oxo-4-[(2S)-3,3,3-trifluoro-2-hydroxypropyl]-4,5-dihydro-1H-1,2,4-triazol-1-yl}methyl)-1-(3-chloropyridin-2-yl)-1H-1,2,4-triazole-5-carboxamide (Example 8A, 200 mg, 368 µmol) in tetrahydrofuran (4.2 ml, 52 mmol) was treated with 4-N,N-dimethylaminopyridine (67.5 mg, 552 µmol) and triethylamine (77 µl, 550 µmol). Phosphorus oxychloride (52 µl, 0.55 mmol) was then added dropwise. The resulting mixture was stirred for 40 min at 0° C. and then for 50 min at room temperature. Thereafter water (420 µl) and a saturated aqueous sodium hydrogen carbonate solution (2.5 ml) were added and the resulting mixture was stirred overnight at room temperature. Tetrahydrofuran was then evaporated at room temperature. The resulting solution was diluted with water and extracted with ethyl acetate. The aqueous phase was brought to pH=1 with a hydrochloric acid solution (1N), diluted with a saturated aqueous sodium chloride solution and extracted with ethyl acetate. The combined organic layers were washed with a saturated sodium chloride solution, dried over magnesium sulfate and evaporated. The residue was purified by preparative HPLC (Method 4) affording 126 mg (55% of th.) of the title compound.

LC-MS (Method 2): $R_t$=1.22 min; MS (ESIneg): m/z=621.0 [M−H]$^−$ $^1$H-NMR (400 MHz, DMSO-d6): δ [ppm]=8.64-8.34 (m, 2H), 8.24 (dd, 1H), 7.96 (s, 1H), 7.80-7.48 (m, 5H), 5.25-5.00 (m, 2H), 4.93-4.76 (br m, 1H), 4.20-3.87 (m, 2H), 3.34 (br s, 2H, overlapping with HDO peak).

Example 18

Potassium (2S)-3-[1-{[5-carbamoyl-1-(3-chloropyridin-2-yl)-1H-1,2,4-triazol-3-yl]methyl}-3-(4-chlorophenyl)-5-oxo-1,5-dihydro-4H-1,2,4-triazol-4-yl]-1,1,1-trifluoropropan-2-yl Hydrogen Phosphate

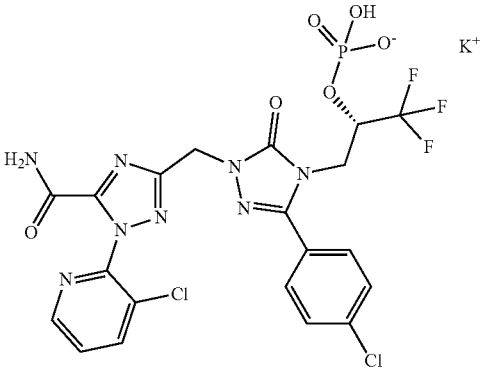 [SMILES: NC(=O)c1nc(Cn2nc(-c3ccc(Cl)cc3)n(C[C@H](OP(=O)([O-])O)C(F)(F)F)c2=O)nn1-c1ncccc1Cl ; [K+]]

A solution of (2S)-3-[1-{[5-carbamoyl-1-(3-chloropyridin-2-yl)-1H-1,2,4-triazol-3-yl]methyl}-3-(4-chlorophenyl)-5-oxo-1,5-dihydro-4H-1,2,4-triazol-4-yl]-1,1,1-trifluoropropan-2-yl dihydrogen phosphate (Example 17, 35.0 mg, 56.2 µmol) in water (2.0 ml) was treated with potassium hydrogen carbonate (11.2 mg, 112 µmol), then stirred for 15 min at room temperature and lyophilized affording 40.2 mg (quant.) of the title compound.

LC-MS (Method 1): $R_t$=0.64 min; MS (ESIpos): m/z=623.0 [M+H]$^+$ $^1$H-NMR (500 MHz, D$_2$O): δ [ppm]=8.54 (dd, 1H), 8.22 (dd, 1H), 7.76-7.58 (m, 5H), 5.42-5.29 (m, 2H), 4.92-4.63 (m, 1H, overlap with HDO peak), 4.20-4.07 (m, 2H).

Example 19

Potassium (2S)-3-[1-{[5-carbamoyl-1-(3-chloropyridin-2-yl)-1H-1,2,4-triazol-3-yl]methyl}-3-(4-chlorophenyl)-5-oxo-1,5-dihydro-4H-1,2,4-triazol-4-yl]-1,1,1-trifluoropropan-2-yl Hydrogen Phosphate

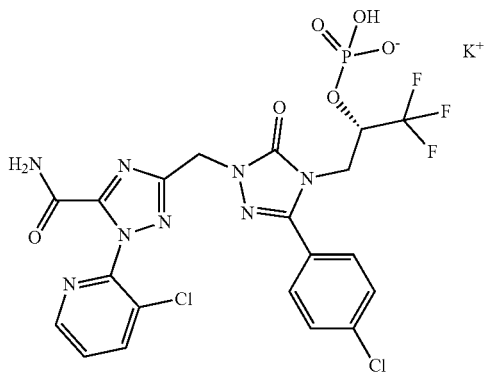 [SMILES: NC(=O)c1nc(Cn2nc(-c3ccc(Cl)cc3)n(C[C@H](OP(=O)([O-])O)C(F)(F)F)c2=O)nn1-c1ncccc1Cl ; [K+]]

A solution of (2S)-3-[1-{[5-carbamoyl-1-(3-chloropyridin-2-yl)-1H-1,2,4-triazol-3-yl]methyl}-3-(4-chlorophenyl)-5-oxo-1,5-dihydro-4H-1,2,4-triazol-4-yl]-1,1,1-trifluoropropan-2-yl dihydrogen phosphate (Example 17, 35.0 mg, 56.2 µmol) in water (2.0 ml) was treated with potassium hydrogen carbonate (5.62 mg, 56.2 µmol), then stirred for 15 min at room temperature and lyophilized affording 37.1 mg (quant.) of the title compound.

LC-MS (Method 1): $R_t$=0.65 min; MS (ESIpos): m/z=623.0 [M+H]$^+$ $^1$H-NMR (500 MHz, D$_2$O): δ [ppm]=8.55-8.51 (m, 1H), 8.23-8.18 (m, 1H), 7.75-7.57 (m, 5H), 5.35 (q, 2H), 4.90-4.63 (m, 1H, overlap with HDO peak), 4.22-4.10 (m, 2H).

Example 20

Sodium (2S)-3-[1-{[5-carbamoyl-1-(3-chloropyridin-2-yl)-1H-1,2,4-triazol-3-yl]methyl}-3-(4-chlorophenyl)-5-oxo-1,5-dihydro-4H-1,2,4-triazol-4-yl]-1,1,1-trifluoropropan-2-yl Hydrogen Phosphate

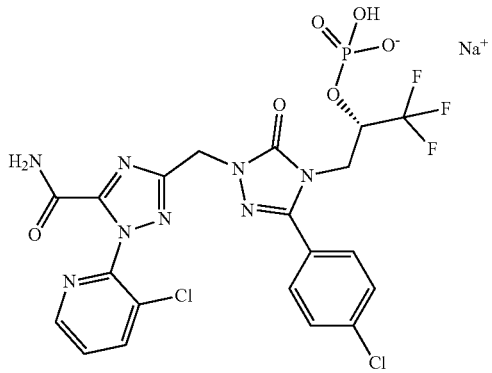 [SMILES: NC(=O)c1nc(Cn2nc(-c3ccc(Cl)cc3)n(C[C@H](OP(=O)([O-])O)C(F)(F)F)c2=O)nn1-c1ncccc1Cl ; [Na+]]

A solution of (2S)-3-[1-{[5-carbamoyl-1-(3-chloropyridin-2-yl)-1H-1,2,4-triazol-3-yl]methyl}-3-(4-chlorophenyl)-5-oxo-1,5-dihydro-4H-1,2,4-triazol-4-yl]-1,1,1-trifluoropropan-2-yl dihydrogen phosphate (Example 17, 35.0 mg, 56.2 µmol) in water (2.0 ml) was treated with disodium carbonate (5.95 mg, 56.2 µmol), then stirred for 15 min at room temperature and lyophilized affording 38.9 mg (quant.) of the title compound.

LC-MS (Method 1): $R_t$=0.65 min; MS (ESIpos): m/z=623.0 [M+H]$^+$ $^1$H-NMR (500 MHz, D$_2$O): δ [ppm]=8.56-8.53 (m, 1H), 8.25-8.20 (m, 1H), 7.75-7.58 (m, 5H), 5.42-5.28 (m, 2H), 4.90-4.64 (m, 1H, overlap with HDO peak), 4.21-4.06 (m, 2H).

Example 21

Sodium (2S)-3-[1-{[5-carbamoyl-1-(3-chloropyridin-2-yl)-1H-1,2,4-triazol-3-yl]methyl}-3-(4-chlorophenyl)-5-oxo-1,5-dihydro-4H-1,2,4-triazol-4-yl]-1,1,1-trifluoropropan-2-yl Hydrogen Phosphate

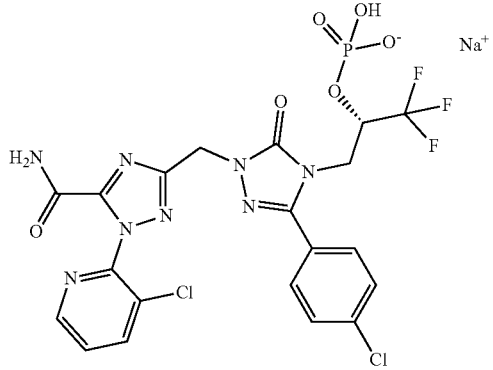 [SMILES: NC(=O)c1nc(Cn2nc(-c3ccc(Cl)cc3)n(C[C@H](OP(=O)([O-])O)C(F)(F)F)c2=O)nn1-c1ncccc1Cl ; [Na+]]

A solution of (2S)-3-[1-{[5-carbamoyl-1-(3-chloropyridin-2-yl)-1H-1,2,4-triazol-3-yl]methyl}-3-(4-chlorophenyl)-5-oxo-1,5-dihydro-4H-1,2,4-triazol-4-yl]-1,1,1-trifluoropropan-2-yl dihydrogen phosphate (Example 17, 35.0 mg, 56.2 µmol) in water (2.0 ml) was treated with sodium hydrogen carbonate (4.72 mg, 56.2 µmol), then stirred for 15 min at room temperature and lyophilized affording 36.4 mg (quant.) of the title compound.

LC-MS (Method 1): $R_t$=0.64 min; MS (ESIpos): m/z=623.1 [M+H]$^+$ $^1$H-NMR (500 MHz, D$_2$O): δ [ppm]=8.56-8.51 (m, 1H), 8.24-8.18 (m, 1H), 7.75-7.56 (m, 5H), 5.43-5.28 (m, 2H), 4.92-4.59 (m, 1H, overlap with HDO peak), 4.25-4.09 (m, 2H).

Example 22

Magnesium (2S)-3-[1-{[5-carbamoyl-1-(3-chloropyridin-2-yl)-1H-1,2,4-triazol-3-yl]methyl}-3-(4-chlorophenyl)-5-oxo-1,5-dihydro-4H-1,2,4-triazol-4-yl]-1,1,1-trifluoropropan-2-yl Phosphate

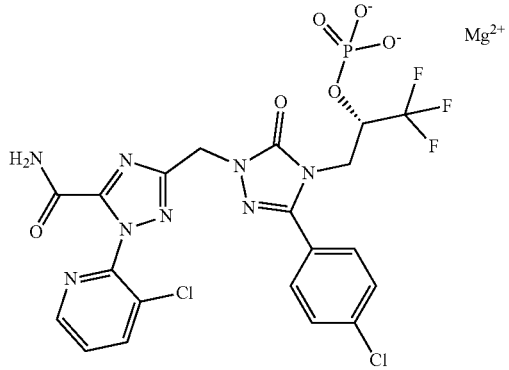 [SMILES: NC(=O)c1nc(Cn2nc(-c3ccc(Cl)cc3)n(C[C@H](OP(=O)([O-])[O-])C(F)(F)F)c2=O)nn1-c1ncccc1Cl ; [Mg+2]]

A solution of (2S)-3-[1-{[5-carbamoyl-1-(3-chloropyridin-2-yl)-1H-1,2,4-triazol-3-yl]methyl}-3-(4-chlorophenyl)-5-oxo-1,5-dihydro-4H-1,2,4-triazol-4-yl]-1,1,1-trifluoropropan-2-yl dihydrogen phosphate (Example 17, 35.0 mg, 56.2 μmol) in water (53 ml) was treated with magnesium carbonate (4.74 mg, 56.2 μmol), then stirred for 15 min at room temperature and lyophilized affording 37.8 mg (quant.) of the title compound.

LC-MS (Method 2): $R_t$=1.13 min: MS (ESIpos): m/z=623.0 [M+H]$^+$ $^1$H-NMR (500 MHz, D$_2$O): δ [ppm]=8.57-8.52 (m, 1H), 8.26-8.19 (m, 1H), 7.77-7.58 (m, 5H), 5.43-5.28 (m, 2H), 4.95-4.58 (m, 1H, overlap with HDO peak), 4.07 (s, 2H).

Example 23

Calcium (2S)-3-[1-{[5-carbamoyl-1-(3-chloropyridin-2-yl)-1H-1,2,4-triazol-3-yl]methyl}-3-(4-chlorophenyl)-5-oxo-1,5-dihydro-4H-1,2,4-triazol-4-yl]-1,1,1-trifluoropropan-2-yl Phosphate

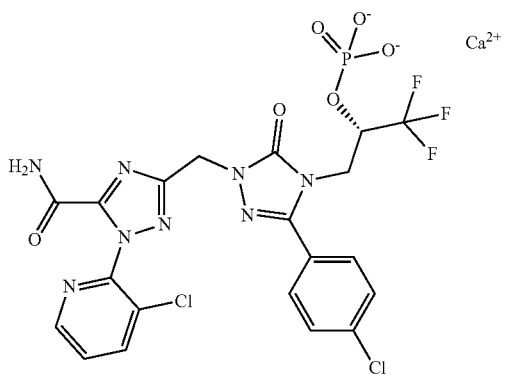

A solution of (2S)-3-[1-{[5-carbamoyl-1-(3-chloropyridin-2-yl)-1H-1,2,4-triazol-3-yl]methyl}-3-(4-chlorophenyl)-5-oxo-1,5-dihydro-4H-1,2,4-triazol-4-yl]-1,1,1-trifluoropropan-2-yl dihydrogen phosphate (Example 17, 35.0 mg, 56.2 μmol) in water (2.0 ml) was treated with calcium acetate monohydrate (1:1) (9.89 mg, 56.2 μmol), then stirred for 15 min at room temperature and lyophilized affording 38.5 mg (quant.) of the title compound.

LC-MS (Method 1): $R_t$=0.65 min; MS (ESIpos): m/z=623.0 [M+H]$^+$ $^1$H-NMR (500 MHz, D$_2$O): δ [ppm]=8.56-8.52 (m, 1H), 8.25-8.19 (m, 1H), 7.76-7.58 (m, 5H), 5.42-5.29 (m, 2H), 4.68 (s, 1H, overlap with HDO peak), 4.23-4.10 (m, 2H).

Example 24

Dipotassium (2S)-3-[1-({5-carbamoyl-1-[3-(trifluoromethyl)pyridin-2-yl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl Phosphate

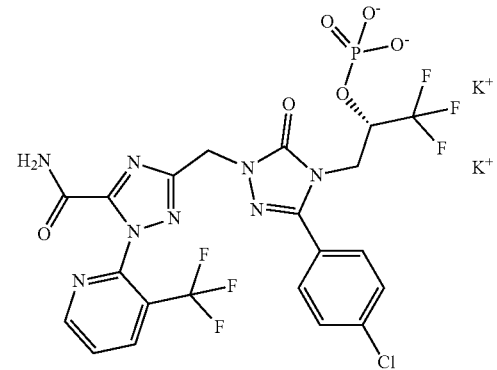 [SMILES: NC(=O)c1nc(Cn2nc(-c3ccc(Cl)cc3)n(C[C@H](OP(=O)([O-])[O-])C(F)(F)F)c2=O)nn1-c1ncccc1C(F)(F)F ; [K+] ; [K+]]

At 0° C., a solution of (2S)-3-[1-({5-carbamoyl-1-[3-(trifluoromethyl)pyridin-2-yl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate (Example 1, 400 mg, 0.609 mmol) in acetonitrile (12 ml) was treated with a solution of potassium hydrogen carbonate (1.2 ml, 1 M, 1.2 mmol). The resulting mixture was stirred for 5 min at 0° C., 5 min at room temperature and lyophilized.

50 mg of the lyophilized compound was dissolved in 2-propanol (3 ml). The resulting solution was slowly concentrated under stirring at room temperature. After 3 weeks, the solvent was completely evaporated. The obtained solid was examined by X-Ray diffractometry and correspond to the title compound as mesomorph material. A potassium stoichiometry of 1.9±0.2 was calculated based on the TGA analysis (9.9% residual solvent in mass) and the ion chromatography (9.1% potassium in mass) according to the following formula:

Stoichiometry=[(%$_{potassium}$)/(1−%$_{residual\ solvent}$−%$_{potassium}$)]×[(M$_{free\ acid}$)/(M$_{potassium}$)]

LC-MS (Method 5): $R_t$=0.67 min; MS (ESIpos): m/z=657.1 [M+H]$^+$ $^1$H-NMR (500 MHz, D2O): δ [ppm]=8.84 (d, 1H), 8.51 (d, 1H), 7.95 (dd, 1H), 7.74-7.56 (m, 4H), 5.47-5.23 (m, 2H), 4.23-4.03 (m, 2H).

TABLE 4

| X-ray powder diffractometry of the compound obtained in example 24 Reflexes [2θ] (peak maxima) | |
|---|---|
| 3.6 | 20.3 |
| 7.3 | 20.7 |
| 11.1 | 21.4 |
| 12.1 | 21.8 |
| 12.5 | 22.2 |
| 12.7 | 22.9 |
| 14.2 | 25.3 |
| 14.5 | 25.6 |
| 15.6 | 25.9 |

TABLE 4-continued

X-ray powder diffractometry of the
compound obtained in example 24
Reflexes [2θ]
(peak maxima)

| | |
|---|---|
| 17.8 | 26.3 |
| 18.1 | |

TABLE 5

Infrared spectrum of the compound
obtained in example 24
Bands
[peak maxima in cm$^{-1}$]

| | |
|---|---|
| 567 | 1031 |
| 578 | 1046 |
| 591* | 1089 |
| 623 | 1123* |
| 639 | 1142* |
| 655 | 1227* |
| 687* | 1258 |
| 708* | 1266 |
| 722 | 1287 |
| 727 | 1320 |
| 747 | 1349* |
| 757* | 1373 |
| 782 | 1403 |
| 808 | 1431* |
| 821 | 1449 |
| 835* | 1496 |
| 883 | 1579 |
| 974 | 1601 |
| 1015 | 1699 |

The bands marked with * are specific to the potassium salt.

Experimental Section—Biological Assays

Abbreviations and Acronyms

Acc. No. accession number
AP alkaline phosphatase
AVP arginine vasopressin
B$_{max}$ maximal ligand binding capacity
BSA bovine serum albumin
cAMP cyclic adenosine monophosphate
Cat. No. catalogue number
cDNA complementary deoxyribonucleic acid
CHO chinese hamster ovary
CRE cAMP response element
Ct cycle threshold
DMEM/F12 Dulbecco's modified Eagle's medium/Ham's F12 medium (1:1)
DNA deoxyribonucleic acid
DMSO dimethylsulfoxide
DTT dithiothreitol
EC$_{50}$ half-maximal effective concentration
EDTA ethylenediamine-tetraacetic acid
FAM carboxyfluorescein succinimidyl ester
f.c. final concentration
FCS fetal calf serum
HEPES 4-(2-hydroxyethyl)piperazine-1-ethanesulfonic acid
IC$_{50}$ half-maximal inhibitory concentration
K$_d$ dissociation constant
K$_i$ dissociation constant of an inhibitor
mRNA messenger ribonucleic acid
PBS phosphate buffered saline
PEG polyethylene glycol
p.o. per os, peroral
RNA ribonucleic acid
RTPCR real-time polymerase chain reaction
SPA scintillation proximity assay
TAMRA carboxytetramethylrhodamine
TRIS; Tris 2-amino-2-hydroxymethylpropane-1,3-diol
v/v volume/volume; concentration, percentage solution Demonstration of the activity of the compounds of the present invention may be accomplished through in vitro, ex vivo, and in vivo assays that are well known in the art. For example, to demonstrate the activity of the compounds of the present invention, the following assays may be used.

B-1. Cellular In Vitro Assay for Determining Vasopressin Receptor Activity

The identification of agonists and antagonists of the V1a and V2 vasopressin receptors from humans, rats and dogs as well as the quantification of the activity of the compounds of the invention is carried out using recombinant cell lines. These cell lines originally derive from a hamster's ovary epithelial cell (Chinese Hamster Ovary, CHO K1, ATCC: American Type Culture Collection, Manassas, Va. 20108, USA). The test cell lines constitutively express the human, rat or dog V1a or V2 receptors. In case of the Gaq-coupled V1a receptors, cells are also stably transfected with a modified form of the calcium-sensitive photoproteins aequorin (human and rat V1a) or obelin (dog V1a), which, after reconstitution with the cofactor coelenterazine, emit light when there are increases in free calcium concentrations [Rizzuto R, Simpson A W, Brini M, Pozzan T, Nature 358, 325-327 (1992); Illarionov B A, Bondar V S, Illarionova V A, Vysotski E S, Gene 153 (2), 273-274 (1995)]. The resulting vasopressin receptor cells react to stimulation of the recombinantly expressed Via receptors by intracellular release of calcium ions, which can be quantified by the resulting photoprotein luminescence. The Gs-coupled V2 receptors are stably transfected into cell lines expressing the gene for firefly luciferase under control of a CRE-responsible promoter. Activation of V2 receptors induces the activation of the CRE-responsive promoter via cAMP increase, thereby inducing the expression of firefly luciferase. The light emitted by photoproteins of V1a cell lines as well as the light emitted by firefly luciferase of V2 cell lines corresponds to the activation or inhibition of the respective vasopressin receptor. The bioluminescence of the cell lines is detected using a suitable luminometer [Milligan G, Marshall F, Rees S, Trends in Pharmacological Sciences 17, 235-237 (1996)].

Test Procedure:

Vasopressin V1a Receptor Cell Lines:

On the day before the assay, the cells are plated out in culture medium (DMEM/F12, 2% FCS, 2 mM glutamine, 10 mM HEPES, 5 µg/ml coelenterazine) in 384-well microtiter plates and kept in a cell incubator (96% humidity, 5% v/v CO$_2$, 37C). On the day of the assay, test compounds in various concentrations are placed for 10 minutes in the wells of the microtiter plate before the agonist [Arg$^8$]-vasopressin at EC$_{50}$ concentration is added. The resulting light signal is measured immediately in a luminometer.

Vasopressin V2 Receptor Cell Lines:

On the day before the assay, the cells are plated out in culture medium (DMEM/F12, 2% FCS, 2 mM glutamine, 10 mM HEPES) in 384-well microtiter plates and kept in a cell incubator (96% humidity, 5% v/v CO$_2$, 37C). On the day of the assay, test compounds in various concentrations and the agonist [Arg$^8$]-vasopressin at EC$_{50}$ concentration are added together to the wells, and plates are incubated for 3 hours in a cell incubator. Upon addition of the cell lysis reagent Triton™ and the substrate luciferin, luminescence of firefly luciferase is measured in a luminometer.

Table 1A below lists individual $IC_{50}$ values for the compounds of the invention (including racemic mixtures as well as separated enantiomers) that were obtained from cell lines transfected with the human V1a or V2 receptor. This means these $IC_{50}$ values are the values for the prodrug and not for the underlying respective drug as the prodrug is mainly stable under the assay conditions. Data for the underlying respective drug are shown in Experiments mentioned below.

TABLE 1A

| Example No. | $IC_{50}$ hV1a [μM] | $IC_{50}$ hV2 [μM] | ratio $IC_{50}$ hV2/hV1a |
|---|---|---|---|
| 4A | 0.00120 | 0.16966 | 141.0 |
| 6A | 0.00058 | 0.02390 | 41.4 |
| 8A | 0.00102 | 0.03900 | 38.2 |
| 1 | 0.01572 | 0.19333 | 12.3 |
| 2 | 0.03950 | 0.62000 | 15.7 |
| 3 | 0.00615 | 0.12300 | 20.0 |
| 4 | 0.01110 | 0.15000 | 13.5 |
| 5 | 0.00505 | 0.08500 | 16.8 |
| 6 | 0.01550 | 0.22000 | 14.2 |
| 7 | 0.00885 | 0.16000 | 18.1 |
| 8 | 0.01700 | 0.14500 | 8.5 |
| 9 | 0.01400 | 0.22500 | 16.1 |
| 10 | 0.01063 | 0.04700 | 4.4 |
| 11 | 0.04050 | 0.03700 | 0.9 |
| 12 | 0.01650 | 0.02400 | 1.5 |
| 13 | 0.01900 | 0.02650 | 1.4 |
| 14 | 0.01900 | 0.01850 | 1.0 |
| 15 | 0.01950 | 0.02100 | 1.1 |
| 16 | 0.02900 | 0.03050 | 1.1 |
| 17 | 0.00980 | 0.13000 | 13.3 |
| 18 | 0.03350 | 0.08400 | 2.5 |
| 19 | 0.02400 | 0.05100 | 2.1 |
| 20 | 0.03950 | 0.08550 | 2.2 |
| 21 | 0.02100 | 0.03800 | 1.8 |
| 22 | 0.04500 | 0.09000 | 2.0 |
| 23 | 0.02700 | 0.07350 | 2.7 |

B-2. Radioactive Binding Assay $IC_{50}$ and $K_i$ values can be determined in radioactive binding assays using membrane fractions of recombinant human embryonic kidney cell line 293 (HEK293) or CHO-K1 cell lines expressing the respective human vasopressin V1a and V2 receptors.

Human recombinant vasopressin V1a receptors expressed in HEK293 cells are used in 50 mM Tris-HCl buffer, pH 7.4, 5 mM $MgCl_2$, 0.1% BSA using standard techniques. Aliquots of prepared membranes are incubated with test compounds in various concentrations in duplicates and 0.03 nM [$^{125}$I]Phenylacetyl-D-Tyr(Me)-Phe-Gln-Asn-Arg-Pro-Arg-Tyr-$NH_2$ for 120 minutes at 25° C. Non-specific binding is estimated in the presence of 1 μM [Arg$^8$]Vasopressin. Receptors are filtered and washed, the filters are then counted to determine [$^{125}$I]Phenylacetyl-D-Tyr(Me)-Phe-Gln-Asn-Arg-Pro-Arg-Tyr-$NH_2$ specifically bound.

CHO-K1 cells stably transfected with a plasmid encoding human vasopressin V2 receptor are used to prepare membranes in 50 mM Tris-HCl buffer, pH 7.4, 10 mM $MgCl_2$, 0.1% BSA using standard techniques. Aliquots of prepared membrane are incubated with test compounds in various concentrations in duplicates and 4 nM [$^3$H](Arg$^8$)-Vasopressin for 120 minutes at 25° C. Non-specific binding is estimated in the presence of 1 mM (Arg$^8$)-vasopressin. Membranes are filtered and washed 3 times and the filters are counted to determine [3H](Arg$_8$)-Vasopressin specifically bound.

$IC_{50}$ values are determined by a non-linear, least squares regression analysis using MathIQ™ (ID Business Solutions Ltd., UK). The inhibition constant $K_i$ is calculated using the equation of Cheng and Prusoff (Cheng, Y., Prusoff, W. H., Biochem. Pharmacol. 22:3099-3108, 1973).

To verify the conversion of prodrugs into the respective drugs, the prodrugs are incubated with and without alkaline phosphatase. Cleavage of the phosphate moiety by alkaline phosphatase converts the prodrug into the underlying respective drug [Coleman J. E. *Annu. Rev. Biophys. Biomol. Struct.* 1992, 21, 441-483]. As prodrug and underlying respective drug show different $IC_{50}$ values, the value of the prodrug after alkaline phosphatase treatment resembles the $IC_{50}$ of the respective drug.

B-3. Cellular In Vitro Assay for Detecting the Action of Vasopressin V1a Receptor Antagonists on the Regulation of Pro-Fibrotic Genes The cell line H9C2 (American Type Culture Collection ATCC No. CRL-1446), described as a cardiomyocyte type isolated from rat cardiac tissue, endogenously expresses the vasopressin V1a receptor AVPR1A in high copy number, whereas AVPR2 expression cannot be detected. Likewise, the cell line NRK49F (ATCC No. CRL1570) isolated from rat kidney tissue, shows similar expression pattern of high AVPR1A mRNA expression and diminishing AVPR2 expression. For cell assays detecting the inhibition of AVPR1A receptor-dependent regulation of gene expression by receptor antagonists, the procedure is as follows:

H9C2 cells or NRK49F cells are seeded in 6-well microtiter plates for cell culture at a cell density of 50 000 cells/well in 2.0 ml of Opti-MEM medium (Invitrogen Corp., Carlsbad, Calif., USA, Cat. No. 11058-021) and held in a cell incubator (96% humidity, 8% v/v $CO_2$, 37C). After 24 hours, sets of three wells (triplicate) are charged with vehicle solution (negative control) and vasopressin solution ([Arg8]-vasopressin acetate, Sigma, Cat. No. V9879), or test compound (dissolved in vehicle: water with 20% v/v ethanol) and vasopressin solution. In the cell culture, the final vasopressin concentration is 1 nM. The test compound solution is added to the cell culture in small volumes, so that a final concentration of 0.03% of ethanol in the cell assay is not exceeded. After an incubation time of 5 hours, the culture supernatant is drawn off under suction, the adherent cells are lysed in 350 μl of RLT buffer (Qiagen, Cat. No. 79216), and the RNA is isolated from the lysate using the RNeasy kit (Qiagen, Cat. No. 74104). This is followed by DNAse digestion (Invitrogen, Cat. No. 18068-015), cDNA synthesis (Promaga, ImProm-II Reverse Transcription System, Cat. No. A3800) and Reverse Transcription Polymerase Chain Reaction (RTPCR) (pPCR MasterMix RT-QP2X-03-075, Eurogentec, Seraing, Belgium). All procedures take place in accordance with the working protocols of the test reagents' manufacturers. The primer sets for the RTPCR are selected on the basis of the mRNA gene sequences (NCBI GenBank Entrez Nucleotide Data Base) using the Primer3Plus program with 6-FAM TAMRA-labelled probes. The RTPCR for determining the relative mRNA expression in the cells of the various assay batches is carried out using the Applied Biosystems ABI Prism 7700 Sequence Detector in 384-well microtiter plate format in accordance with the instrument operating instructions. The relative gene expression is represented by the delta-delta Ct value [Applied Biosystems, User Bulletin No. 2 ABI Prism 7700 SDS, Dec. 11, 1997 (updated 10/2001)] with reference to the level of expression of the ribosomal protein L-32 gene (GenBank Acc. No. NM_013226) and the threshold Ct value of Ct=35.

To verify the conversion of prodrugs into the respective drugs, the prodrugs are incubated with and without alkaline phosphatase. Cleavage of the phosphate moiety by alkaline phosphatase converts the prodrug into the underlying respective drug [Coleman J. E., *Annu. Rev. Biophys. Biomol. Struct.* 1992, 21, 441-483]. As prodrug and underlying respective drug show different $IC_{50}$ values, the value of the prodrug after alkaline phosphatase treatment resembles the $IC_{50}$ of the respective drug.

B-4. Cellular In Vitro Assay for Verification of Prodrug Conversion into Drug

To verify the conversion of prodrugs into the respective drugs, the prodrugs are incubated with and without alkaline phosphatase. Cleavage of the phosphate moiety by alkaline phosphatase converts the prodrug into the underlying respective drug [Coleman J. E., Annu. Rev. Biophys. Biomol. Struct. 1992, 21, 441-483]. As prodrug and underlying respective drug show different $IC_{50}$ values, the value of the prodrug after alkaline phosphatase treatment resembles the $IC_{50}$ of the respective drug. The determination of $IC_{50}$ values of compounds of the invention at the human V1a receptor is carried out using a recombinant cell line. The cell line originally derives from a hamster's ovary epithelial cell (Chinese Hamster Ovary, CHO K1, ATCC: American Type Culture Collection, Manassas, Va. 20108, USA). The test cell line constitutively expresses the human V1a receptor. Cells are also stably transfected with a modified form of the calcium-sensitive photoprotein aequorin which, after reconstitution with the cofactor coelenterazine, emits light upon increase in free calcium concentration [Rizzuto R, Simpson A W, Brini M, Pozzan T, *Nature* 358, 325-327 (1992); Illarionov B A, Bondar V S, Illarionova V A, Vysotski E S, *Gene* 153 (2), 273-274 (1995)]. The resulting vasopressin receptor cell reacts to stimulation of the recombinantly expressed V1a receptor by intracellular release of calcium ions, which can be quantified by the resulting luminescence of photoprotein. The bioluminescence of the cell line is detected using a suitable luminometer [Milligan G, Marshall F, Rees S, *Trends in Pharmacological Sciences* 17, 235-237 (1996)].

Test Procedure:

On the day before the assay, the cells are seeded in culture medium (DMEM/F12, 2% FCS, 2 mM glutamine, 10 mM HEPES, 5 µg/ml coelenterazine) in 384-well microtiter plates and kept in a cell incubator (96% humidity, 5% v/v $CO_2$, 37C). On the day of the assay, 100 µl of test compounds at a concentration of 100 µM are incubated for 15 minutes with 500 units alkaline phosphatase at 37° C. in tyrode buffer (20 mM HEPES, 130 mM NaCl, 5 mM KCl, 5 mM $NaHCO_3$, 2 mM $MgCl_2$, pH 7,4). After incubation compounds are immediately diluted and placed for 10 minutes at 37° C. on the before seeded V1a cells. For detection of antagonistic activity of the compounds [$Arg^8$]-vasopressin at $EC_{50}$ concentration is added and the resulting light signal is measured immediately in a luminometer.

LC-MS of the compound samples (Example 4A and Example 1) with and without alkaline phosphatase (AP) was performed.

Method 6 (LC-MS):

Instrument MS: Waters TOF instrument; Instrument type UPLC: Waters Acquity I-CLASS; Column: Waters, HSST3, 2.1×50 mm, C18 1.8 µm; eluent A: 1 l water+0.01% formic acid; eluent B: 1 l acetonitrile+0.01% formic acid; gradient: 0.0 min 2% B→0.5 min 2% B→7.5 min 95% B→10.0 min 95% B; Oven: 50° C.; Flow: 1.00 ml/min; UV-Detection: 210 nm.

Example 4A with AP
LC-MS (Method 6): $R_t$=3.83 min; MS (ESIpos): m/z=577.1 $[M+H]^+$ Example 4A without AP
LC-MS (Method 6): $R_t$=3.84 min; MS (ESIpos): m/z=577.1 $[M+H]^+$ Example 1 with AP
LC-MS (Method 6): $R_t$=3.83 min; MS (ESIpos): m/z=577.1 $[M+H]^+$ Example 1 without AP
LC-MS (Method 6): $R_t$=3.19 min; MS (ESIpos): m/z=657.1 $[M+H]^+$

TABLE 2A

IC50 values of drugs and their respective prodrugs in the presence and absence of alkaline phosphatase (AP)

| Example No. | drug | $IC_{50}$ with AP [µM] | $IC_{50}$ without AP [µM] |
|---|---|---|---|
| 1 | prodrug | 0.00145 | 0.01310 |
| 4A | drug | 0.00135 | 0.00125 |
| 10 | prodrug | 0.00130 | 0.01100 |
| 6A | drug | 0.00135 | 0.00135 |
| 17 | prodrug | 0.00103 | 0.00945 |
| 8A | drug | 0.00110 | 0.00170 |

B-5. Inhibition of Vasopressin Induced Aggregation of Human Platelets for Verification of Prodrug Conversion into Drug Human platelets endogenously express the V1a receptor. It was found that relatively high arginine vasopressin (AVP) concentrations (ca. 50-100 nM) stimulate platelet aggregation ex vivo. Therefore, platelets enriched from human blood may serve as a V1a expressing tissue for pharmacological studies with vasopressin antagonists.

To verify the conversion of prodrugs into the respective drugs, the prodrugs are incubated with and without alkaline phosphatase. Cleavage of the phosphate moiety by alkaline phosphatase converts the prodrug into the drug. As prodrug and underlying respective drug show different $IC_{50}$ values, the value of the prodrug after alkaline phosphatase treatment resembles the $IC_{50}$ of the respective drug.

100 µl of test compound at a concentration of 100 µM are incubated for 15 min with 500 units alkaline phosphatase at 37° C. in modified Tyrode buffer (134 mM NaCl, 12 mM $NaH_2PO_4*H_2O$, 0.34 mM $NaH_2PO_4*H_2O$, 2.9 mM KCl, 5 mM HEPES, 5 mM Glucose) and stored at 4° C. until further use in the platelet aggregation assay.

Human blood is collected into plastic tubes containing 1/10 volume of 0.106 M trisodium citrate by venous puncture from nonsmoking healthy volunteers (n=4/group) who are drug free for at least 1 week. Platelet-rich plasma (PRP) is obtained by centrifugation of the blood sample at 140 g for 20 min at room temperature. The resulting pellet is discarded and the PRP further centrifuged (11.000 rpm, 1 min) to produce platelet-poor plasma (PPP). Platelet aggregation is measured turbidimetrically using an aggregometer (APACT 4). The reaction is followed by monitoring changes in light transmission on 178 µL PRP aliquots, under continuous stirring at 37° C., against PPP control. Various concentrations of vasopressin antagonists (in 2 µL) are added to PRP 5 min before the addition of 20 µL AVP (final concentration 100 nM). The inhibitory effects of the compounds are determined by measuring the maximal amplitude of the aggregation curve compared with the control response. $IC_{50}$ values are calculated on the basis of a concentration-response inhibition curve by an iterative nonlinear regression program. All values are expressed as mean values (Table 3A).

TABLE 3A

Effects of test compounds on aggregation in human platelet rich plasma.

| Example No. | drug | $IC_{50}$ with AP [μM] | $IC_{50}$ without AP [μM] |
|---|---|---|---|
| 1 | prodrug | 0.01274 | 0.14460 |
| 4A | drug | 0.01020 | 0.02115 |

B-6. Effects on the Contraction of Isolated Rat Vessel Rings

Isolated Aorta

Test compounds can be investigated on isolated aortic rings from male Wistar rats endogenously expressing the V1a receptor. Male Wistar rats are euthanized using carbon dioxide. The aorta is removed and placed in ice-cold Krebs-Henseleit buffer of following composition (in mmol/l): NaCl 112, KCl 5.9, $CaCl_2$ 2.0, $MgCl_2$ 1.2, $NaH_2PO_4$ 1.2, $NaHCO_3$ 25, glucose 11.5. The aorta is cut into 3 mm rings and transferred to 20 ml organ baths containing Krebs-Henseleit solution equilibrated with 95% $O_2$, 5% $CO_2$ at 37° C. For recording of isometric tension the rings are mounted between two hooks. The resting tension is adjusted to 3 g. After an equilibration period, each experiment is started by exposing the preparation to K+(50 mM) Krebs-Henseleit solution. The aortic rings are than pre-contracted using 1 nmol/l Arg-vasopressin. After a stable contraction is established, a cumulative dose response curve of the test compound is constructed. The stabilized contraction induced by Arg-vasopressin is defined as 100% tension. The relaxation is expressed as percentage tension.

Isolated A. renalis

Male Wistar rats (200-250 g) are euthanized using carbon dioxide. The A. renalis is removed and placed in ice-cold Krebs-Henseleit buffer of following composition (in mmol/1): NaCl 112, KCl 5.9, $CaCl_2$ 2.0, $MgCl_2$ 1.2, $NaH_2PO_4$ 1.2, $NaHCO_3$ 25, glucose 11.5. For measurement of isometric tension, ring segments, 2 mm in length, are mounted in a small vessel chamber myograph (Danish Myo Technology A/S, Denmark) using two tungsten wires fixed to mounting jaws. One mounting jaw is attached to a micrometer, allowing control of vessel circumference. The other mounting jaw is attached to a force transducer for measurement of tension development. The whole preparation is kept in a chamber with physiological salt solution at 37° C., bubbled with oxygen. After a 30 min equilibration period, the vessels are stretched to their optimal lumen diameter for active tension development which is determined based on the internal circumference-wall tension ratio. The internal circumference is set to 90% of what the vessels would have if they are exposed to a passive tension equivalent to that produced by a transmural pressure of 100 mmHg.

Afterwards, the vessels are washed three times with Krebs-Henseleit buffer and left to equilibrate for 30 min. The contractility is then tested by a twofold exposure to a high $K^+$ solution (50 mmol/l KCl). After washing with Krebs-Henseleit buffer the vessels are then pre-contracted using 1 nmol/l Arg-vasopressin. After a stable contraction is established, a cumulative dose response curve of the test compound is constructed. The stabilized contraction induced by Arg-vasopressin is defined as 100% tension. The relaxation is expressed as percentage tension.

To verify the conversion of prodrugs into the respective drugs, the prodrugs are incubated with and without alkaline phosphatase. Cleavage of the phosphate moiety by alkaline phosphatase converts the prodrug into the underlying respective drug [Coleman J. E., *Annu. Rev. Biophys. Biomol. Struct.* 1992, 21, 441-483]. As prodrug and underlying respective drug show different $IC_{50}$ values, the value of the prodrug after alkaline phosphatase treatment resembles the $IC_{50}$ of the respective drug.

B-7. In Vivo Assay for Detecting Cardiovascular Effects: Blood Pressure Measurement in Anaesthetized Rats (Vasopressin 'Challenge' Model)

Male Sprague-Dawley rats (250-350 g body weight) are used under ketamine/xylazine/pentobarbital injection anaesthesia. Polyethylene tubes (PE-50, Intramedic®), prefilled with heparin-containing (500 IU/ml) isotonic sodium chloride solution, are introduced into the jugular vein and the femoral vein and then tied in. Arg-vasopressin (SIGMA) is injected via one venous access, with the aid of a syringe; the test substance is administered via the second venous access. For determination of the systolic blood pressure, a pressure catheter (Millar SPR-320 2F) is tied into the carotid artery. The arterial catheter is connected to a pressure transducer which feeds its signals to a recording computer equipped with suitable recording software. In a typical experiment, the experimental animal is administered 3-4 successive bolus injections at intervals of 10-15 min with a defined amount of Arg-vasopressin (30 ng/kg) in isotonic sodium chloride solution. When the blood pressure has reached initial levels again, the test substance is administered as a bolus, with subsequent continuous infusion, in a suitable solvent. After this, at defined intervals (10-15 min), the same amount of Arg-vasopressin as at the start is administered again. On the basis of the blood pressure values, a determination is made of the extent to which the test substance counteracts the hypertensive effect of Arg-vasopressin. Control animals only receive solvent instead of the test substance.

Following intravenous administration, the compounds of the invention, in comparison to the solvent controls, bring about an inhibition of the blood pressure increase caused by Arg-vasopressin.

B-8. In Vivo Assay for Detecting Vasopressin V2 Receptor-Meidated Effects: Diuresis Investigations in Conscious Rats Kept in Metabolism Cages Wistar rats (400-500 g body weight) are kept with free access to feed (Altromin) and drinking water. During the experiment, the animals are kept with free access to drinking water for 7 hours individually in metabolism cages suitable for rats of this weight class (Tecniplast Deutschland GmbH, D-82383 Hohenpeißenberg). At the beginning of the experiment, the animals are administered the test substance in a volume of 1 ml/kg body weight of a suitable solvent (2-Hydroxylpropyl-beta-cyclodextrin) by intravenous application. Control animals only receive solvent. Controls and substance tests are carried out in parallel on the same day. Control groups and substance-dose groups each consist of 6 to 8 animals. During the experiment, the urine excreted by the animals is collected continuously in a receiver at the base of the cage. The volume of urine is determined separately for each animal. Before the beginning of the experiment, the body weight of the individual animals is determined.

Following intravenous administration, in comparison with the solvent control applications, a vasopressin V2 receptor blocking compound would bring about an increased excretion of urine, which is based essentially on an increased excretion of water (aquaresis).

Table 4A below shows observed changes in urinary excretion relative to solvent control (=100%) for exemplary compounds of the invention and comparison compounds at three different dosages:

TABLE 4A

| Example No. | Dosage [mg/kg] | Urinary volume [% vs. control] | Dosage [mg/kg] | Urinary volume [% vs. control] | Dosage [mg/kg] | Urinary volume [% vs. control] |
|---|---|---|---|---|---|---|
| WO2016/071212 (Example 82) | 0.3 | 413 | 1.0 | 848 | 3.0 | 1416 |
| 4A | 0.3 | 95 | 1.0 | 154 | 3.0 | 134 |
| 1 | 0.3 | 127 | 1.0 | 117 | 3.0 | 108 |

The results shown in Table 4A demonstrate that the compounds of the present invention do not possess any significant dose-dependent V2 blocking activity at the indicated doses in vivo. This is in contrast to Example 82 of WO2016/071212 which gave rise to a dose-dependent, up to fourteen-fold increase in urinary volume versus the vehicle control group at a dose of 3 mg/kg i.v.

B-9. In Vivo Assay for Detecting Protective Renal Effects: Acute Ischemia/Reperfusion Injury Model in Rodents Laboratory bred male C57B1/6J mice 6-8 weeks old are obtained from Taconic Biosciences, male 6-8 weeks old Sprague Dawley® rats are obtained from Charles River. Both rats and mice are maintained under standard laboratory conditions, 12 hour light-dark cycles with access to normal chow and drinking water at libitum. For the ischemia reperfusion injury model a total of 10-12 rats or mice is used in each control and experimental group.

Animals are anesthetized with continuous inhaled isoflurane. A right nephrectomy is performed through a right flank incision 7 days before the ischemic procedures in the contralateral kidneys. For renal ischemia a left flank incision is made. Renal vessels are exposed by dissection of the left renal pedicle. Non-traumatic vascular clamps are used to stop blood flow (artery and vein) during 45 min (rats) or 25 min (mice) of ischemia. Reperfusion is established by removing the clamps. The abdominal wall (muscular layer and skin) is closed with 5.0 polypropylene sutures. Temgesic® (Buprenorphin, 0.025 mg/kg s.c.) is applied as an analgesic.

Urine of each animal is collected in metabolic cages over night before sacrifice at 24h post ischemia. Upon sacrifice, blood samples are obtained under terminal anesthesia. After centrifugation of the blood samples, serum is isolated. Both serum creatinine and serum urea are measured via clinical biochemistry analyzer (Pentra 400). For the assessment of serum and urinary kidney injury biomarkers (Neutrophil gelatinase-associated lipocalin [NGAL], kidney injury molecule-1 [KIM-1] and Osteopontin) ELSA's are performed according to the manufacturers protocol. Both urinary creatinine and albumin are measured to determine the albumin/creatinine ratio.

Total RNA is isolated from kidneys. Left kidneys are snap-frozen in liquid nitrogen at sacrifice. Kidney tissue is then homogenized and RNA is obtained. Total RNA is transcribed to cDNA. Using TaqMan real-time PCR renal NGAL, Osteopontin, KIM-1, Nephrin and Podocin mRNA expression is analyzed in whole kidney tissue.

Differences between groups are analyzed by one-way ANOVA with Dunnett's corrections for multiple comparisons. Statistical significance is defined as $p<0.05$. All statistical analyses are done using GraphPad Prism 7.

B-10. In Vivo Assay for Detecting Cardiovascular Effects: Hemodynamic Investigations in Anesthetized Dogs Male beagle dogs (Beagle, Marshall BioResources, USA) with a weight of between 10 and 15 kg are anesthetized with pentobarbital (30 mg/kg iv, Narcoren®, Merial, Germany) for the surgical interventions and the hemodynamic and functional investigation termini. Pancuroniumbromide (Pancuronium Inresa, Inresa, Germany, 2-4 mg/animal i.v.) serves additionally as a muscle relaxant. The dogs are intubated and ventilated with an oxygen/ambient air mixture (30/70%), about 2.5-4 L/min. Ventilation takes place using a ventilator from GE Healthcare (Avance, Germany) and is monitored using a carbon dioxide analyzer (-Datex Ohmeda). The anesthesia is maintained by continual infusion of pentobarbital (50 µg/kg/min); fentanyl is used as an analgesic (10 µg/kg/h).

In preparatory interventions, the dogs are fitted with a cardiac pacemaker. At start of experiment, a cardiac pacemaker from Biotronik (Logos®, Germany) is implanted into a subcutaneous skin pocket and is contacted with the heart via a pacemaker electrode (Siello S60®, Biotronik, Germany) which is advanced through the external jugular vein, with illumination, into the right ventricle.

Thereafter accesses are removed and the dog wakes spontaneously from the anesthesia. After a further 7 days, the above-described pacemaker is activated and the heart is stimulated at a frequency of 220 beats per minute.

The actual drug testing experiments take place 28 days after the beginning of pacemaker stimulation, using the following instrumentation:

Introduction of a bladder catheter for bladder relief and for measuring the flow of urine Attachment of electrocardiography (ECG) leads to the extremities for ECG measurement Introduction of a sheath introducer filled with sodium chloride solution into the femoral artery. This tube is connected to a pressure sensor (Braun Melsungen, Melsungen, Germany) for measuring the systemic blood pressure Introduction of a Millar Tip catheter (type 350 PC, Millar Instruments, Houston, USA) through a port secured in the carotid artery, for measuring cardiac hemodynamics.

Introduction of a Swan-Ganz catheter (CCOmbo 7.5F, Edwards, Irvine, USA) via the jugular vein into the pulmonary artery, for measuring the cardiac output, oxygen saturation, pulmonary arterial pressures and central venous pressure Siting of a venous catheter in the cephalic vein, for infusing pentobarbital, for liquid replacement and for blood sampling (determination of the plasma levels of substance or other clinical blood values)

Siting of a venous catheter in the saphenous vein, for infusing fentanyl and for administration of substance Infusion of vasopressin (Sigma) in increasing dosage, up to a dose of 4 mU/kg/min. The pharmacological substances are then tested with this dosage.

The primary signals are amplified if necessary (ACQ7700, Data Sciences International, USA or Edwards-Vigilance-Monitor, Edwards, Irvine, USA) and subsequently fed into the Ponemah system (Data Sciences International, USA) for evaluation. The signals are recorded continuously throughout the experimental period, and are further processed digitally by said software, and averaged over 30 seconds.

B-11. Acute Effects on Vasopressin-Mediated Changes of Systemic Hemodynamics, Renal Blood Flow and Oxygenation in Anesthetized Rats Experiments are performed on male Sprague Dawley rats (Charles River, Deutschland; 350-450 g body weight). In preparation for surgical procedures rats are anesthetized with isoflurane and placed on a heated table to maintain core body temperature at 37° C., assessed using a rectal thermometer inserted. Inhalation anesthesia with isoflurane is applied using a calibrated vaporizer to induce and maintain anesthesia with 5 vol. % and 2 vol. % isoflurane, respectively. A PE50 cannula is placed in the right arteria femoralis for monitoring mean arterial pressure (MAP). Another PE50 catheter is inserted into the vena femoralis for intravenous infusion. The left kidney is exposed by a flank incision and separated from the perirenal attachments. The kidney capsule remains intact. During surgery and the subsequent equilibration and control periods, the rats receive an intravenous infusion of saline (0.9% NaCl) at rate 100 μL/min. Renal measurements of renal blood flow (RBF) are recorded using a laser Doppler blood flow probe (Oxford Optronix, UK) that is attached and stabilized to the surface of the kidney. The probe is inserted into the renal cortex to a depth of 2 mm and another into the renal medulla at 4 mm. The renal blood flow, oxygen and temperature are measured by combined sensor probe (Oxford Optronix, UK). MAP, heart rate (HR), RBF, temperature and oxygen are continuously recorded. After surgery and equilibration, baseline measurements are determined for 20 minutes. The rats are then intravenously infused with vasopressin atrate 50 ng/kg/min in 100 μL/kg for 20 minutes. In the third period, the effect of combined infusion of vasopressin and adual vasopressin receptor antagonist (Example 82 of WO 2016/071212) or a selective V1a antagonist (Example 1) or vehicle that is applied as a bolus in different concentration is determined.

TABLE 5A

Effects of dual vasopressin receptor antagonist Example 82 of WO2016/071212 on vasopressin (AVP) mediated changes of systemic and renal hemodynamics in rats.

| Example 82 of WO 2016/071212 | Basal Mean ± SD | AVP 50 [ng/kg/min] Mean ± SD | AVP + Vehicle 1 [mL/kg] Mean ± SD | AVP + Example 82 of WO 2016/071212 30 [μg/kg] Mean ± SD |
|---|---|---|---|---|
| MAP [mmHg] | 96.69 ± 1.18 | 135.20 ± 12.87 | 129.90 ± 0.76 | 100.40 ± 3.22 |
| HR [BPM] | 330.4 ± 2.33 | 276.90 ± 18.85 | 263.30 ± 0.27 | 309.60 ± 10.79 |
| RBF [U] | 822.2 ± 14.22 | 668.20 ± 62.58 | 614.50 ± 7.94 | 820.90 ± 20.28 |
| pO$_2$ [mmHg] | 39.05 ± 0.98 | 20.56 ± 10.27 | 7.86 ± 2.21 | 23.71 ± 0.34 | n = 8 animals/group.
Data are mean ± SD.
MAP = mean arterial blood pressure.
HR = Heart rate.
RBF = renal blood flow.
pO$_2$ = partial pressure of renal oxygen

TABLE 6A

Effects of the selective vasopressin V1a receptor antagonist Example 4A on vasopressin (AVP) mediated changes of systemic and renal hemodynamics in rats.

| Example 4A | Basal Mean ± SD | AVP 50 [ng/kg/min] Mean ± SD | AVP + Vehicle 1 [mL/kg] Mean ± SD | AVP + Example 4A 30 [μg/kg] Mean ± SD |
|---|---|---|---|---|
| MAP [mmHg] | 97.44 ± 0.57 | 135.40 ± 12.9 | 130.50 ± 1.09 | 114.80 ± 7.42 |
| HR [BPM] | 334.10 ± 1.12 | 283.40 ± 16.69 | 268.60 ± 2.68 | 270.50 ± 2.89 |
| RBF [U] | 1060.00 ± 8.89 | 758.30 ± 107.40 | 698.60 ± 18.83 | 878.10 ± 96.92 |
| pO$_2$ [mmHg] | 27.86 ± 0.96 | 17.04 ± 4.42 | 11.32 ± 0.87 | 15.86 ± 4.01 | n = 8 animals/group.
Data are mean ± SD.
MAP = mean arterial blood pressure.
HR = Heart rate.
RBF = renal blood flow.
pO$_2$ = partial pressure of renal oxygen

TABLE 7A

Effects of the vasopressin V1a receptor antagonist Example 1 on vasopressin (AVP) mediated changes of systemic and renal hemodynamics in rats.

| Example 1 | Basal Mean ± SD | AVP 50 [ng/kg/min] Mean ± SD | AVP + Vehicle 1 [mL/kg] Mean ± SD | AVP + Example 1 30 [μg/kg] Mean ± SD |
|---|---|---|---|---|
| MAP [mmHg] | 97.93 ± 1.09 | 124.60 ± 10.04 | 117.70 ± 2.27 | 103.50 ± 4.97 |
| HR [BPM] | 371.20 ± 1.73 | 292.30 ± 25.25 | 272.20 ± 1.56 | 276.20 ± 4.46 |
| RBF [U] | 924.60 ± 16.72 | 791.90 ± 46.47 | 780.30 ± 13.35 | 877.00 ± 43.01 |
| pO$_2$ [mmHg] | 20.70 ± 0.39 | 10.54 ± 3.391 | 11.20 ± 0.61 | 14.32 ± 1.13 | n = 8 animals/group.
Data are mean ± SD.
MAP = mean arterial blood pressure.
HR = Heart rate.
RBF = renal blood flow.
pO$_2$ = partial pressure of renal oxygen

B-12. pH Stability 0.15 mg of the test compound is dissolved in 0.1 ml dimethylsulfoxide and 0.4 ml acetonitrile. For complete dissolution the HPLC vial with the sample solution is shaken and treated with ultrasonic irradiation. Then 1.0 ml of the respective buffer solution is added and the sample is vortexed. The sample solution is analyzed by HPLC to determine the amount of the test compound at a particular time over a period of 24 h at 37° C. The peak areas in percentage are used for quantification.

Buffers pH 4.0: Fluka buffer, Order No. 33643 (11.76 g citric acid, 2.57 g sodium chloride and 2.72 g sodium hydroxide).

pH 7.4: 90 g of sodium chloride, 13.61 g of potassium dihydrogen phosphate and 83.35 g of 1 M sodium hydroxide solution are made up to 1 litre with Millipore water and then diluted 1:10. Adjust with phosphoric acid to pH=7.4.

pH 10: Fluka buffer, Order No. 33649 (4.77 g Borax, 0.73 g sodium hydroxide).

15 μl portions of the sample solution are analysed by HPLC at different times (0 h, 1 h, 2 h, 4 h and 24 h) at 37° C. The peak areas in percentage are used for quantification.

HPLC Method

| Eluent: | A = 1 ml trifluoroacetic acid /L in water; B = 1 ml trifluoroacetic acid/L in acetonitrile |
|---|---|
| Column: | Nucleodur 100 C18ec, 3 μm, 50 × 2 mm |
| Temperature: | 37° C. |
| Detection: | 214 nm |
| Injection: | 15 μl |

| Gradient: | Time (mm) | A (%) | B (%) | Flow (ml/min) |
|---|---|---|---|---|
| | 0.0 | 98 | 2 | 0.75 |
| | 1.0 | 98 | 2 | 0.75 |
| | 15.0 | 5 | 95 | 0.75 |
| | 17.5 | 5 | 95 | 0.75 |
| | 17.7 | 98 | 2 | 1.50 |
| | 18.2 | 98 | 2 | 1.50 |
| | 18.5 | 98 | 2 | 1.00 |
| | 19.0 | 98 | 2 | 0.75 |

The ratios of the peak area (F) at different times in relation to the peak area at the starting point are shown in Table 8A for representative examples:

TABLE 8A

| Example No. | Buffer pH | % Test Compound after 4 h [F(t = 4 h) × 100/F(t = 0 h)] | % Test Compound after 24 h [F(t = 24 h) × 100/F(t = 0 h)] |
|---|---|---|---|
| 1 | 4 | 100 | 100 |
| 1 | 7.4 | 99 | 99 |
| 1 | 10 | 99 | 98 |
| 10 | 4 | 100 | 100 |
| 10 | 7.4 | 100 | 100 |
| 17 | 4 | 100 | 100 |
| 17 | 7.4 | 100 | 100 |

B-13. Solubility

Experimental Procedure

For each substance 0.5-0.6 mg are weighed exactly. In each case, sufficient medium is added to the sample in such a way that a concentration of c=500 μg/ml is obtained. This sample solution is shaken for 24 h at room temperature and 1400 rpm.

A further sample weight of 0.5-0.6 mg is required for the DMSO calibration solution. This sample is filled with DMSO to a concentration of c=600 μg/ml. Two calibration solutions are prepared from this stock solution. In a 2 ml HPLC vial, 1000 μl of DMSO are initially introduced and 34.4 μl of the stock solution are pipetted (c=20 g/ml). 71.4 g of this solution (c=20 μg/ml) are placed in a further 2 ml HPLC vial containing 500 μl of DMSO (c=2.5 μg/ml).

After shaking the test solutions, 230 μl of the supernatant are transferred into a centrifuge tube and centrifuged at 42 000 rpm (223 000 g) for 30 min. 180 μl of the supernatant are then taken and each diluted with DMSO (1:5 sample 1; 1:100 sample 2), and transferred to HPLC vials. The two calibration solutions and the dilute sample solutions are analyzed by HPLC. Quantification is performed over the corresponding peak areas.

Solvent

Distilled water; trifluoroacetic acid (Merck; 1.08262.0100); acetonitrile (HPLC grade); DMSO (Merck; 8.02912.2500).

Media

Citrate Buffer pH4:

Fluka buffer, Order No. 33643 (11.76 g citric acid, 2.57 g sodium chloride and 2.72 g sodium hydroxide).

Buffer pH7:

Fluka buffer, Order No. 33646 (3.52 g potassium dihydrogenphosphate, 7.26 g sodium hydrogen phosphate).

PBS-Buffer pH7.4:

Solution of 6.18 g sodium chloride and 3.96 g sodium dihydrogen phosphate in 1 L distilled water, adjust with 1M aqueous sodium hydroxide solution to pH 7.4.

Tris-Buffer pH8.5:

0.6057 g TRIS was dissolved in 95 ml water, adjust to pH 8.5 with aqueous hydrochloric acid, fill with water until 100 ml volume is reached.

HPLC Equipment

Agilent 1100 or comparable apparatus with UV-detection, variable wavelength (z.B. Diode-Array); ultrasonic bath; Vibromix von Janke & Kunkel; Thermomixer from Eppendorf HPLC-Method Eluent A: 1 ml trifluoracetic acid/L water;
Eluent B: 1 ml trifluoracetic acid/L acetonitrile

| Gradient: | Time (min) | A (%) | B (%) | Flow (ml/min) |
|---|---|---|---|---|
| | 0.0 | 98 | 2 | 1.5 |
| | 0.2 | 98 | 2 | 1.5 |
| | 3.3 | 10 | 90 | 1.5 |
| | 4.0 | 10 | 90 | 1.5 |
| | 4.1 | 98 | 2 | 2.5 |
| | 4.7 | 98 | 2 | 2.5 |
| | 5.0 | 98 | 2 | 1.5 |

Column: Zorbax Extend-c18, 50 × 3.0 mm, 3.5 µm;
column temperature: 30° C.; Flow: 1.5 ml/min;
detector: 214/254 nm; injection volume: 20 µl.

The solubility for representative examples is shown in Table 9A.

TABLE 9A

| Example No. | Solubility [mg/l] | | | |
|---|---|---|---|---|
| | pH = 4 | pH = 7.0 | pH = 7.4 | pH = 8.5 |
| 4A | 8.7 | not detectable | — | 6.7 |
| 6A | not detectable | not detectable | — | 4.3 |
| 8A | 5.9 | 2.8 | — | 4.0 |
| 1 | >500 | >500 | — | >500 |
| 4 | >500 | — | >500 | >500 |
| 6 | >500 | — | 464 | 464 |
| 7 | >500 | — | >500 | >500 |
| 9 | >500 | — | >500 | 447 |
| 10 | 454 | >500 | — | 479 |
| 17 | >500 | >500 | — | >500 |
| 20 | >500 | — | >500 | >500 |
| 22 | >500 | — | >500 | >500 |

B-14. Determination of Pharmacokinetic Parameters Following Intravenous and Oral Administration The pharmacokinetic parameters of the compounds according to the invention are determined in male Wistar rats, female Beagle dogs and female Cynomolgus monkeys. Intravenous administration is carried out by means of a suitable formulation vehicle for the respective species, such as a plasma/DMSO formulation or physiological saline (pH4 or above) for rats, or a water/PEG400/ethanol formulation or physiological saline (pH4 or above) for dogs and monkeys. In all species, oral administration of the dissolved substance is performed via gavage, using a suitable formulation vehicle, such as a water/PEG400/ethanol formulation or physiological saline. The taking of blood from rats is simplified by inserting a suitable catheter into the right Vena jugularis externa prior to substance administration. The operation is carried out at least one day prior to the experiment with isofluran anaesthesia and administration of an analgesic (atropin/Rimadyl (3/1) 0.1 ml s.c.). The blood is taken (generally at least 6 time points) within a time window including terminal time points of at least 7 hours to a maximum of 72 hours after substance administration. When the blood is taken, it is passed into tubes containing a suitable anti-coagulant, preferably K-EDTA. Then the blood plasma is obtained by centrifugation and is optionally stored at −20° C. until further processing.

An internal standard (which may also be a chemically unrelated substance) is added to the samples of the compounds according to the invention, calibration samples and qualifiers, and there follows protein precipitation by means of excess acetonitrile. Alternatively, the internal standard is added to acetonitrile and the mixture is then added in excess to samples of the compounds according to the invention, calibration samples and qualifiers for protein precipitation. Addition of a buffer solution matched to the LC conditions, and subsequent vortexing, is followed by centrifugation at 2800 g. The supernatant is analysed by LC-MS/MS using C18 or biphenyl reversed-phase columns and variable mobile phase mixtures. The substances are quantified via the peak heights or areas from extracted ion chromatograms of specific selected ion monitoring experiments.

The plasma concentration/time plots determined are used to calculate the pharmacokinetic parameters such as AUC (area under the curve), Cmax (maximal concentration), t1/2 (terminal half-life), F (bioavailability), MRT (mean residence time) and CL (clearance), using a validated pharmacokinetic calculation program.

Since the substance quantification is carried out in plasma, it is necessary to determine the blood/plasma distribution of the substance in order to be able to adjust the pharmacokinetic parameters correspondingly. For this purpose, a defined amount of substance is incubated in whole blood of the species in question in a rocking roller mixture for 20 min. After centrifugation at 2800 g, the plasma concentration is measured (by means of LC-MS/MS using C18 or biphenyl reversed-phase columns and variable mobile phase mixtures) and determined by calculating the ratio of the whole blood concentration versus plasma concentration (Cblood/Cplasma value).

C) Working Examples of Pharmaceutical Compositions

The substances according to the invention can be converted to pharmaceutical preparations as follows:

Tablet:

Composition:

100 mg of the compound of Example 1, 50 mg of lactose (monohydrate), 50 mg of maize starch, 10 mg of polyvinylpyrrolidone (PVP 25) (from BASF, Germany) and 2 mg of magnesium stearate.

Tablet weight 212 mg. Diameter 8 mm, radius of curvature 12 mm.

Production:

The mixture of the compound of Example 1, lactose and starch is granulated with a 5% strength solution (n/m) of the PVP in water. After drying, the granules are mixed with the magnesium stearate for 5 min. This mixture is compressed in a conventional tabletting press (see above for format of the tablet).

Oral Suspension:

Composition:

1000 mg of the compound of Example 1, 1000 mg of ethanol (96%), 400 mg of Rhodigel (xanthan gum) (from FMC, USA) and 99 g of water. 10 ml of oral suspension correspond to a single dose of 100 mg of the compound of the invention.

Production:

The Rhodigel is suspended in ethanol, and the compound of Example 1 is added to the suspension. The water is added while stirring. The mixture is stirred for about 6 h until swelling of the Rhodigel is complete.

Sterile i.v. Solution:

The compound according to the invention is dissolved at a concentration below saturation solubility in a physiologically acceptable solvent (for example isotonic sodium chloride solution, glucose solution 5% and/or PEG 400 solution 30%). The solution is sterilized by filtration and filled into sterile and pyrogen-free injection containers.

Although the invention has been disclosed with reference to specific embodiments, it is apparent that other embodiments and variations of the invention may be devised by others skilled in the art without departing from the true spirit and scope of the invention. The claims are intended to be construed to include all such embodiments and equivalent variations.

The invention claimed is:

1. A compound of formula (I)

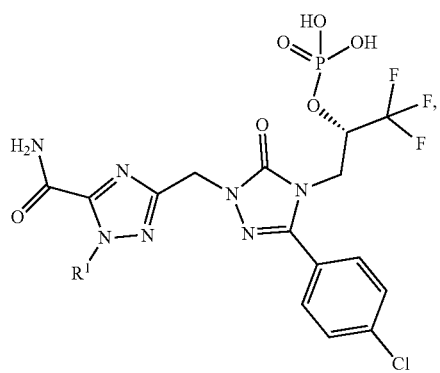

(I)

in which
R¹ represents a group of formula

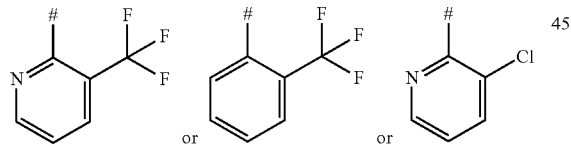

in which
\# represents the point of attachment to the 1,2,4-triazolyl-ring, And/Or a pharmaceutically acceptable salt thereof, solvate thereof and/or solvate of a salt thereof.

2. A compound of formula (I) according to claim 1, wherein
R¹ represents a group of formula

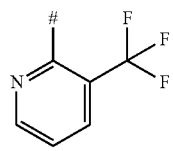

in which
\# represents the point of attachment to the 1,2,4-triazolyl-ring.

3. (2S)-3-[1-({5-Carbamoyl-1-[3-(trifluoromethyl)pyridin-2-yl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate according to claim 1 of a formula below

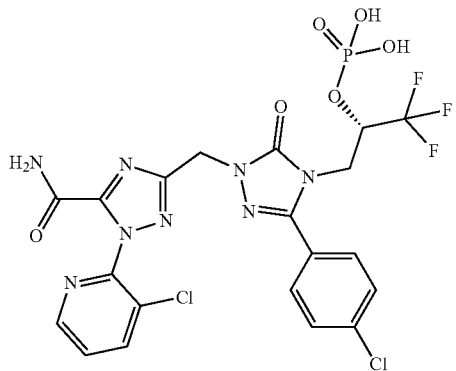 [SMILES: NC(=O)c1nc(Cn2nc(-c3ccc(Cl)cc3)n(C[C@H](OP(=O)(O)O)C(F)(F)F)c2=O)nn1-c1ncccc1Cl]

And/or a pharmaceutically acceptable salt thereof, solvate thereof and/or solvate of a salt thereof.

4. (2S)-3-[1-({5-Carbamoyl-1-[3-(trifluoromethyl)pyridin-2-yl]-1H-1,2,4-triazol-3-yl}methyl)-3-(4-chlorophenyl)-5-oxo-1,5-dihydro-4H-1,2,4-triazol-4-yl]-1,1,1-trifluoropropan-2-yl dihydrogen phosphate according to claim 1 of a formula below

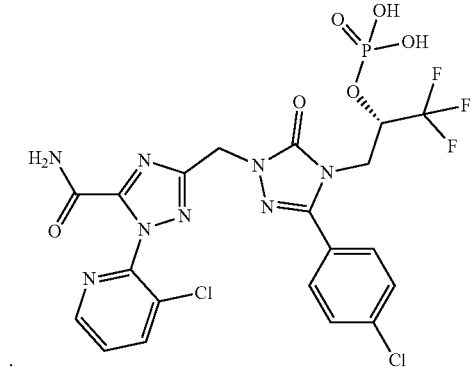

5. Process for preparing a compound of formula (I) and/Or a pharmaceutically acceptable salt thereof, solvate thereof andor solvate of a salt thereof, according to claim 1, wherein a compound of formula

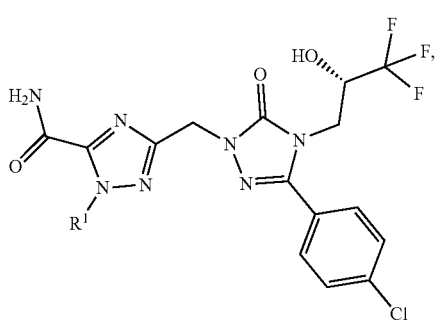

is reacted with phosphorus oxychloride and hydrolysed to give a compound of formula (I),
or
[B] a compound of formula

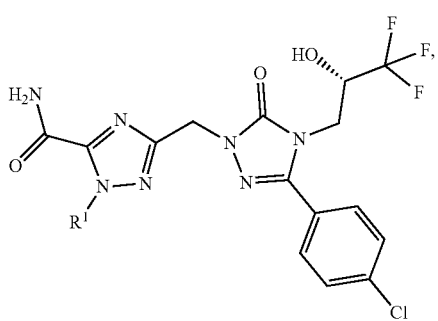

is reacted with tetrabenzyl diphosphate and benzyl groups are removed under reducing conditions to give a compound of formula (I), optionally followed, where appropriate, by converting the compound of formula (I) into respective pharmaceutically acceptable salt thereof, solvate thereof and/or solvate of a salt thereof by treatment with one or more corresponding solvents and/or bases.

6. Compound as defined in claim 1 for treatment and/or prevention of one or more diseases.

7. Compound as defined in claim 1 for treatment and/or prevention of one or more acute and/or chronic kidney diseases including diabetic nephropathy, acute and chronic heart failure, preeclampsia, peripheral arterial disease (PAD), coronary microvascular dysfunction (CMD), Raynaud's syndrome, dysmenorrhea, cardiorenal syndrome, hypervolemic and euvolemic hyponatremia, liver cirrhosis, ascites, edema and the syndrome of inadequate ADH secretion (SIADH).

8. A product comprising a compound as defined in claim 1 or a composition thereof for treatment and/or prevention of one or more acute and chronic kidney diseases including diabetic nephropathy, acute and chronic heart failure, preeclampsia, peripheral arterial disease (PAD), coronary microvascular dysfunction (CMD), Raynaud's syndrome dysmenorrhea, cardiorenal syndrome, hypervolemic and euvolemic hyponatremia, liver cirrhosis, ascites, edema and the syndrome of inadequate ADH secretion (SIADH).

9. Pharmaceutical composition comprising a compound as defined in claim 1 and one or more pharmaceutically acceptable excipients.

10. Pharmaceutical composition of claim 9 comprising one or more first active ingredients, optionally one or more compounds of formula (I), and one or more further active ingredients, optionally one or more additional therapeutic agents selected from the group consisting of diuretics, angiotensin All antagonists, ACE inhibitors, beta-receptor blockers, mineralocorticoid receptor antagonists, organic nitrates, NO donors, activators and stimulators of the soluble guanylate cyclase, and positive-inotropic agents, antiinflammatory agents, immunosuppressive agents, phosphate binders and/or compounds which modulate vitamin D metabolism.

11. The pharmaceutical composition as defined in claim 9 for treatment and/or prevention of one or more acute and chronic kidney diseases including diabetic nephropathy, acute and chronic heart failure, preeclampsia, peripheral arterial disease (PAD), coronary microvascular dysfunction (CMD), Raynaud's syndrome, dysmenorrhea, cardiorenal syndrome, hypervolemic and euvolemic hyponatremia, liver cirrhosis, ascites, edema and the syndrome of inadequate ADH secretion (SIADH).

12. Method for treatment and/or prevention of one or more acute and chronic kidney diseases including diabetic nephropathy, acute and chronic heart failure, preeclampsia, peripheral arterial disease (PAD) and coronary microvascular dysfunction (CMD), Raynaud's syndrome dysmenorrhea, cardiorenal syndrome, hypervolemic and euvolemic hyponatremia, liver cirrhosis, ascites, edema and the syndrome of inadequate ADH secretion (SIADH) in a human or other mammal, comprising administering to a human or other mammal in need thereof a therapeutically effective amount of one or more compounds as defined in claim 1.

* * * * *